United States Patent
Bell et al.

(10) Patent No.: US 8,133,891 B2
(45) Date of Patent: Mar. 13, 2012

(54) TRICYCLIC ANILIDE SPIROLACTAM CGRP RECEPTOR ANTAGONISTS

(75) Inventors: Ian M. Bell, Harleysville, PA (US); Steven N. Gallicchio, Wyndmoor, PA (US); Craig A. Stump, Pottstown, PA (US); Cory R. Theberge, King of Prussia, PA (US); Joseph P. Vacca, Telford, PA (US); C. Blair Zartman, Hatfield, PA (US); Xufang Zhang, Dresher, PA (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 41 days.

(21) Appl. No.: 12/718,386

(22) Filed: Mar. 5, 2010

(65) Prior Publication Data
US 2010/0160334 A1    Jun. 24, 2010

Related U.S. Application Data

(62) Division of application No. 11/662,246, filed as application No. PCT/US2005/031617 on Sep. 6, 2005, now Pat. No. 7,696,192.

(60) Provisional application No. 60/608,294, filed on Sep. 9, 2004.

(51) Int. Cl.
*A01N 43/58* (2006.01)
*A01N 43/60* (2006.01)
*A61K 31/50* (2006.01)
*A61K 31/495* (2006.01)

(52) U.S. Cl. ........................... 514/250; 544/346

(58) Field of Classification Search .............. 514/250; 544/346
See application file for complete search history.

(56) References Cited

U.S. PATENT DOCUMENTS

| | | | |
|---|---|---|---|
| 6,548,505 B1 | 4/2003 | Martin et al. | |
| 7,696,192 B2 * | 4/2010 | Bell et al. ............... | 514/211.12 |

FOREIGN PATENT DOCUMENTS

| | | |
|---|---|---|
| WO | 01/83478 A2 | 11/2001 |
| WO | 2004/083187 A1 | 9/2004 |
| WO | 2006/029153 A2 | 3/2006 |

OTHER PUBLICATIONS

Supplementary EPO Search Report for counterpart European Appl. No. 05798847.1, dated Jun. 25, 2009.

* cited by examiner

*Primary Examiner* — Yong Chu
*Assistant Examiner* — Valerie Rodriguez-Garcia
(74) *Attorney, Agent, or Firm* — Nicole M. Beeler; Gerard M. Devlin

(57) ABSTRACT

The present invention is directed to compounds of Formula I: I (where $A^1, A^2, B^1, B^2, B^3, B^4, D^1, D^2$, J, K, T, U, V, W, X, Y, Z, $R^4, R^{5a}, R^{5b}, R^{5c}$, m and n are defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

(I)

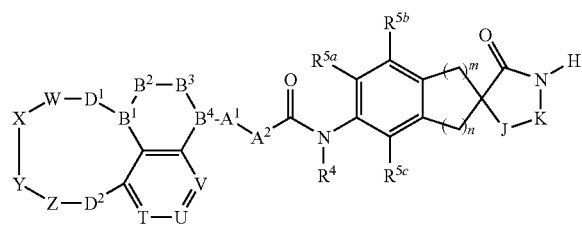

19 Claims, No Drawings

TRICYCLIC ANILIDE SPIROLACTAM CGRP RECEPTOR ANTAGONISTS

CROSS REFERENCE TO RELATED APPLICATIONS

This is a divisional application of U.S. patent application Ser. No. 11/662,246 filed Mar. 8, 2007 now U.S. Pat. No. 7,696,192, which is a national stage filing under 35 USC 371 of PCT/US2005/031617, filed Sep. 6, 2005, which claims priority to U.S. Provisional Application No. 60/608,294, filed Sep. 9, 2004.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human $\alpha$-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache. Compelling evidence of the efficacy of CGRP antagonists for the treatment of migraine has been provided by clinical studies using intravenously administered BIBN4096BS. This CGRP antagonist was found to be a safe and effective acute treatment for migraine (Olesen et al., N. Engl. J. Med., 2004, 350(11), 1104-1110).

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

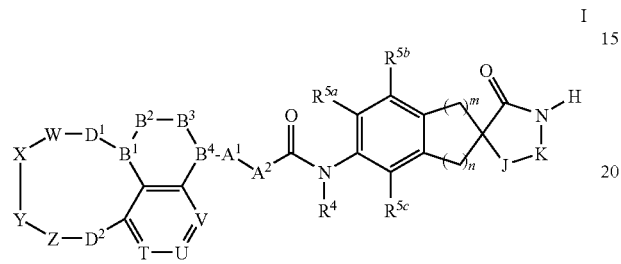

wherein:

$A^1$ and $A^2$ are each independently selected from: a bond and —$CR^{13}R^{14}$—, where one of $A^1$ and $A^2$ is optionally absent;
$B^1$ and $B^4$ are each independently selected from:

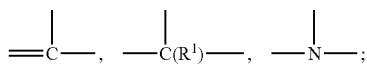

$B^2$ and $B^3$ are each independently selected from: a bond, $=C(R^1)$—, —$CR^1R^2$—, —$C(=O)$—, —$C(=S)$—, —$C(=NR^1)$—, $=N$—, —$N(R^1)$—, —O—, —S—, and —$SO_2$—, where one of $B^2$ and $B^3$ is optionally absent;
$D^1$ and $D^2$ are each independently selected from: $=C(R^1)$—, —$CR^1R^2$—, —$C(=O)$—, —$C(=S)$—, —$C(=NR^1)$—, $=N$—, —$N(R^1)$—, —O—, —S— and —$SO_2$—;
J is selected from: $=C(R^{6a})$—, —$CR^{13}R^{14}$— and —$C(=O)$—;
K is selected from: $=C(R^{6b})$—, —$CR^{13}R^{14}$—, —$C(=O)$—, —$SO_2$—, $=N$— and —$N(R^{6b})$—;
T, U and V are each independently selected from: $=C(R^1)$— and $=N$—, wherein at least one of T, U, and V is $=C(R^1)$—;
W, X, Y, and Z are each independently selected from: a bond, $=C(R^1)$—, —$CR^1R^2$—, —$C(=O)$—, —$C(=S)$—, —$C(=NR^1)$—, $=N$—, —$N(R^1)$—, —O—, —S—, —S(O)— and —$SO_2$—;
$R^1$ and $R^2$ are each independently selected from:
(1) hydrogen;
(2) —$C_{1-6}$alkyl, which is unsubstituted or substituted with 1-7 substituents each independently selected from:
(a) halo,
(b) hydroxy,
(c) —O—$C_{1-6}$alkyl,
(d) —$C_{3-6}$cycloalkyl,
(e) phenyl or heterocycle, wherein heterocycle is selected from: azetidinyl, imidazolyl, oxazolyl, pyridyl, pyrimidinyl, pyrazinyl, pyridazinyl, piperidinyl, azepanyl, piperazinyl, pyrazolyl, pyrrolidinyl, thiazolyl, thienyl, triazolyl, tetrazolyl, tetrahydrofuryl and morpholinyl, which phenyl or heterocycle is unsubstituted or substituted with 1-5 substituents each independently selected from: —$C_{1-6}$alkyl, —O—$C_{1-6}$alkyl, halo, hydroxy, trifluoromethyl, —$OCF_3$ and oxo,
(f) —$CO_2R^9$, wherein $R^9$ is independently selected from: hydrogen, —$C_{3-6}$cycloalkyl, benzyl, phenyl and —$C_{1-6}$alkyl which is unsubstituted or substituted with 1-6 fluoro,
(g) —$NR^{10}R^{11}$, wherein $R^{10}$ and $R^{11}$ are each independently selected from: hydrogen, —$C_{5-6}$cycloalkyl, benzyl, phenyl, —$COR^9$, —$SO_2R^{12}$, and —$C_{1-6}$alkyl which is unsubstituted or substituted with 1-6 fluoro,
(h) —$SO_2R^{12}$ wherein $R^{12}$ is selected from: —$C_{1-6}$alkyl which is unsubstituted or substituted with 1-6 fluoro, —$C_{5-6}$cycloalkyl, benzyl and phenyl,
(i) —$CONR^{10a}R^{11a}$, wherein $R^{10a}$ and $R^{11a}$ are each independently selected from:
hydrogen, —$C_{1-6}$alkyl which is unsubstituted or substituted with 1-6 fluoro, —$C_{5-6}$cycloalkyl, benzyl, phenyl,
or $R^{10a}$ and $R^{11a}$ are joined to form a ring selected from azetidinyl, pyrrolidinyl, piperidinyl, piperazinyl and morpholinyl, which ring is unsubstituted or substituted with 1-5 substituents each independently selected from: —$C_{1-6}$alkyl, —O—$C_{1-6}$alkyl, halo, hydroxyl, phenyl and benzyl,
(j) trifluoromethyl,
(k) —$OCO_2R^9$,
(l) —$(NR^{10a})CO_2R^9$,
(m) —$O(CO)NR^{10a}R^{11a}$, and
(n) —$(NR^9)(CO)NR^{10a}R^{11a}$, and
(o) —O—$C_{3-6}$cycloalkyl,
(3) —$C_{3-6}$cycloalkyl, which is unsubstituted or substituted with 1-7 substituents each independently selected from:
(a) halo,
(b) hydroxy,
(c) —O—$C_{1-6}$alkyl,
(d) trifluoromethyl, and
(e) phenyl, which is unsubstituted or substituted with 1-5 substituents each independently selected from: —$C_{1-6}$alkyl, —O—$C_{1-6}$alkyl, halo, hydroxy and trifluoromethyl,
(4) —$C_{2-6}$alkynyl, which is unsubstituted or substituted with 1-7 substituents each independently selected from:
(a) halo,
(b) hydroxy,
(c) —O—$C_{1-6}$alkyl,
(d) —$C_{3-6}$cycloalkyl,
(d) trifluoromethyl, and
(e) phenyl, which is unsubstituted or substituted with 1-5 substituents each independently selected from: —$C_{1-6}$alkyl, —O—$C_{1-6}$alkyl, halo, hydroxy and trifluoromethyl,
(5) phenyl or heterocycle, wherein heterocycle is selected from: pyridyl, pyrimidinyl, pyrazinyl, thienyl, pyridazinyl, pyrrolidinyl, azepanyl, azetidinyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-dioxolanyl, oxadiazolyl, piperidinyl, tetrahydropyranyl, tetrahydrothienyl, tetrahydrothiopyranyl and morpholinyl, which phenyl or heterocycle is unsubstituted or substituted with 1-5 substituents each independently selected from:
(a) —$C_{1-6}$alkyl which is unsubstituted or substituted with 1-6 fluoro,
(b) halo,
(c) hydroxy,
(d) —O—$C_{1-6}$alkyl which is unsubstituted or substituted with 1-6 fluoro,
(e) —$C_{3-6}$cycloalkyl,
(f) phenyl or heterocycle, wherein heterocycle is selected from: pyridyl, pyrimidinyl, pyrazinyl, thienyl and morpholinyl,
which phenyl or heterocycle is unsubstituted or substituted with 1-5 substituents each independently selected from: —$C_{1-6}$alkyl, —O—$C_{1-6}$alkyl, halo, hydroxy and trifluoromethyl,
(g) —$CO_2R^9$,
(h) —(CO)$R^9$,
(i) —$NR^{10}R^{11}$,
(j) —$CONR^{10}R^{11}$,
(k) oxo
(l) —$SR^{12}$,
(m) —S(O)$R^{12}$,
(n) —$SO_2R^{12}$, and
(o) —CN
(6) halo,
(7) oxo,
(8) hydroxy,
(9) —O—$C_{1-6}$alkyl which is unsubstituted or substituted with 1-5 halo,
(10) —CN,
(11) —$CO_2R^9$,
(12) —$NR^{10}R^{11}$,
(13) —$SO_2R^{12}$,
(14) —$CONR^{10a}R^{11a}$,
(15) —$OCO_2R^9$,
(16) —($NR^{10a}$)$CO_2R^9$,
(17) —O(CO)$NR^{10a}R^{11a}$,
(18) —($NR^9$)(CO)$NR^{10a}R^{11a}$,
(19) —(CO)—(CO)$NR^{10a}R^{11a}$,
(20) —(CO)—(CO)$OR^9$, and
(21) —($NR^{10}$)(CO)$R^9$;
$R^4$ is selected from: hydrogen, $C_{1-6}$ alkyl which is unsubstituted or substituted with 1-6 fluoro, $C_{5-6}$ cycloalkyl, benzyl and phenyl;
$R^{5a}$, $R^{5b}$ and $R^{5c}$ are each independently selected from: hydrogen, $C_{1-6}$ alkyl, —O—$C_{1-6}$alkyl, —$OCF_3$, trifluoromethyl, halo, hydroxy and —CN;
$R^{6a}$ and $R^{6b}$ are each independently selected from:
(1) hydrogen;
(2) —$C_{1-4}$alkyl which is unsubstituted or substituted with 1-5 substituents each independently selected from:
(a) halo,
(b) —O—$C_{1-6}$alkyl,
(c) —$C_{3-6}$cycloalkyl,
(d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl, which phenyl or heterocycle is unsubstituted or substituted with 1-3 substituents each independently selected from: —$C_{1-6}$alkyl, —O—$C_{1-6}$alkyl, halo, hydroxy, trifluoromethyl and —$OCF_3$,
(3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl and morpholinyl, which phenyl or heterocycle is unsubstituted or substituted with 1-3 substituents each independently selected from:
(a) —$C_{1-4}$alkyl which is unsubstituted or substituted with 1-5 fluoro,
(b) halo,
(c) hydroxy,
(d) —O—$C_{1-4}$alkyl which is unsubstituted or substituted with 1-5 fluoro,
(e) —$C_{3-6}$cycloalkyl, and
(f) phenyl,
(4) halo,
(5) hydroxy,
(6) —O—$C_{1-6}$alkyl which is unsubstituted or substituted with 1-5 halo,
(7) —CN,
(8) —$CO_2R^9$,
(9) —$NR^{10}R^{11}$, and
(10) —$CONR^{10a}R^{11a}$;
or $R^{6a}$ and $R^{6b}$ and the atom(s) to which they are attached are joined to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —$C_{1-6}$alkyl which is unsubstituted or substituted with 1-3 substituents each independently selected from:
(i) halo,
(ii) hydroxy,
(iii) —O—$C_{1-6}$alkyl,
(iv) —$C_{3-6}$cycloalkyl,
(v) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —($NR^{10a}$)$CO_2R^9$,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —$C_{3-6}$cycloalkyl, —$C_{1-6}$alkyl which is unsubstituted or substituted with 1-6 fluoro, and —O—$C_{1-6}$alkyl which is unsubstituted or substituted with 1-6 fluoro,
(c) halo,
(d) —$SO_2R^{12}$,
(e) hydroxy,
(f) —O—$C_{1-6}$alkyl which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —($NR^{10a}$)$CO_2R^9$,
(m) —O(CO)$NR^{10a}R^{11a}$,
(n) —($NR^9$)(CO)$NR^{10a}R^{11a}$, and
(o) oxo;

$R^{13}$ and $R^{14}$ are each independently selected from: hydrogen, hydroxyl, halo and $C_{1-6}$ alkyl which is unsubstituted or substituted with 1-6 fluoro;
m is 1 or 2;
n is 1 or 2;
and pharmaceutically acceptable salts thereof and individual enantiomers and diastereomers thereof.

The following examples are presented in order to illustrate some structures that fall within the definition of formula I, but should not be taken as limiting the scope of the invention in any way.

For example, when: $A^1$ is —$CH_2$—; $A^2$ is a bond; $B^1$ is

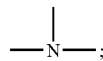

$B^4$ is

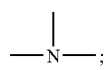

$B^2$ is —C(=O)—; $B^3$ is a bond; $D^1$ is —$CH_2$—; $D^2$ is —N(Me)—; J is =C($R^{6a}$)—; K is =C($R^{6b}$)—; T is =C(H)—; U is =C(Me)—; V is =C(H)—; W is —C(=O)—; X is a bond; Y is a bond; Z is a bond; $R^4$ is hydrogen; $R^{5a}$ is hydrogen; $R^{5b}$ is hydrogen; $R^{5c}$ is hydrogen; $R^{6a}$ and $R^{6b}$ and the carbon atom(s) to which they are attached are joined together to form an unsubstituted pyridyl ring; m is 1; and n is 1; the following structure may be obtained:

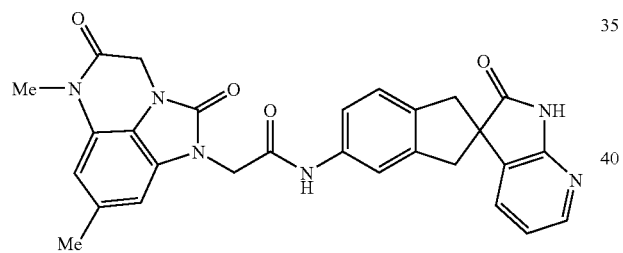

As another example, when: $A^1$ is —$CH_2$—; $A^2$ is a bond; $B^1$ is

$B^4$ is

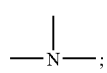

$B^2$ is —C(=O)—; $B^3$ is a bond; $D^1$ is —$CH_2$—; $D^2$ is —N(H)—; J is =C($R^{6a}$)—; K is =C($R^{6b}$)—; T is =N—; U is =C(H)—; V is =C(H)—; W is —C(=O)—; X is a bond; Y is a bond; Z is a bond; $R^4$ is hydrogen; $R^{5a}$ is hydrogen; $R^{5b}$ is hydrogen; $R^{5c}$ is hydrogen; $R^{6a}$ and $R^{6b}$ and the carbon atom(s) to which they are attached are joined together to form an unsubstituted pyridyl ring; m is 1; and n is 1; the following structure may be obtained:

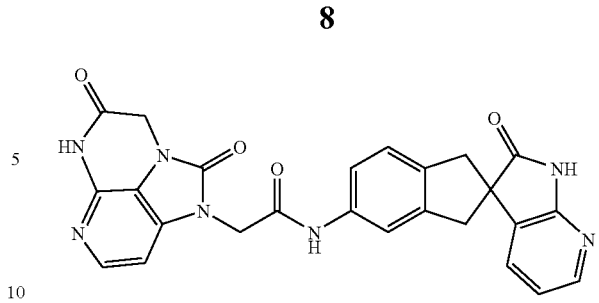

As another example, when: $A^1$ is —$CH_2$—; $A^2$ is a bond; $B^1$ is

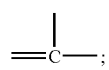

$B^4$ is

$B^2$ is =C(H)—; $B^3$ is a bond; $D^1$ is —N(H)—; $D^2$ is —$CH_2$—; J is =C($R^{6a}$)—; K is =C($R^{6b}$)—; T is =C(H)—; U is =C(H)—; V is =C(H)—; W is —C(=O)—; X is a bond; Y is a bond; Z is a bond; $R^4$ is hydrogen; $R^{5a}$ is hydrogen; $R^{5b}$ is hydrogen; $R^{5c}$ is hydrogen; $R^{6a}$ and $R^{6b}$ and the carbon atom(s) to which they are attached are joined together to form an unsubstituted pyridyl ring; m is 1; and n is 1; the following structure may be obtained:

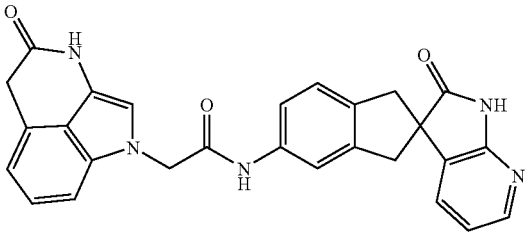

As another example, when: $A^1$ is —$CH_2$—; $A^2$ is a bond; $B^1$ is

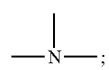

$B^4$ is

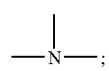

$B^2$ is —C(=O)—; $B^3$ is a bond; $D^1$ is —$CH_2$—; $D^2$ is —N(H)—; J is —$CH_2$—; K is —C(=O)—; T is =C(H)—; U is =C(H)—; V is =C(H)—; W is —C(=O)—; X is a bond; Y is a bond; Z is a bond; $R^4$ is hydrogen; $R^{5a}$ is hydrogen; $R^{5b}$ is hydrogen; $R^{5c}$ is hydrogen; m is 1; and n is 1; the following structure may be obtained:

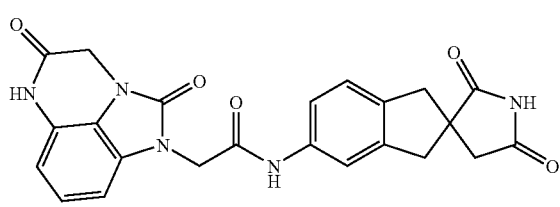

As another example, when: $A^1$ is —$CH_2$—; $A^2$ is a bond; $B^1$ is

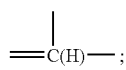

$B^4$ is

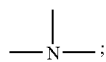

$B^2$ is =C(H)—; $B^3$ is a bond; $D^1$ is —C(=O)—; $D^2$ is —N(H)—; J is =C($R^{6a}$)—; K is =C($R^{6b}$)—; T is =C(Cl)—;
U is =C(H)—; V is =C(H)—; W is —C(=O)—; X is a bond; Y is a bond; Z is a bond; $R^4$ is hydrogen; $R^{5a}$ is hydrogen; $R^{5b}$ is hydrogen; $R^{5c}$ is hydrogen; $R^{6a}$ and $R^{6b}$ and the carbon atom(s) to which they are attached are joined together to form an unsubstituted pyridyl ring; m is 1; and n is 1; the following structure may be obtained:

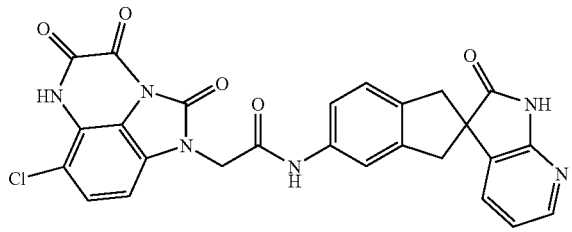

As another example, when: $A^1$ is —$CH_2$—; $A^2$ is a bond; $B^1$ is

$B^4$ is

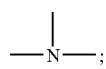

$B^2$ is —$CH_2$—; $B^3$ is a bond; $D^1$ is —$CH_2$—; $D^2$ is —N(Me)—; J is =C($R^{6a}$)—; K is =C($R^{6b}$)—; T is =C(H)—; U is =C(H)—; V is =C(H)—; W is —$CH_2$—; X is —$CH_2$—; Y is —C(=O)—; Z is a bond;
$R^4$ is hydrogen; $R^{5a}$ is hydrogen; $R^{5b}$ is hydrogen; $R^{5c}$ is hydrogen; $R^{6a}$ and $R^{6b}$ and the carbon atom(s) to which they are attached are joined together to form an unsubstituted pyridyl ring; m is 1; and n is 1; the following structure may be obtained:

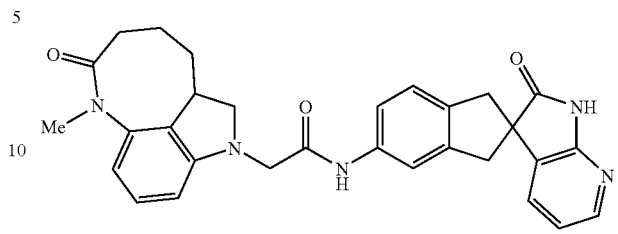

An embodiment of the present invention includes compounds of the formula Ia:

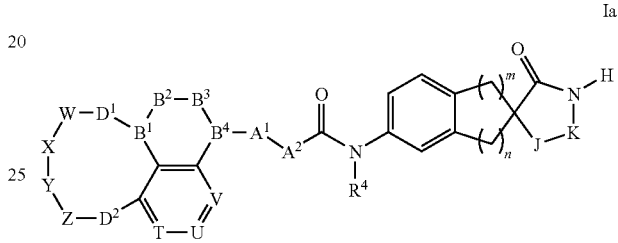

wherein $A^1$, $A^2$, $B^1$, $B^2$, $B^3$, $B^4$, $D^1$, $D^2$, J, K, T, U, V, W, X, Y, Z, $R^4$, m, and n are defined herein; and pharmaceutically acceptable salts thereof and individual enantiomers and diastereomers thereof.

Another embodiment of the present invention includes compounds of the formula Ib:

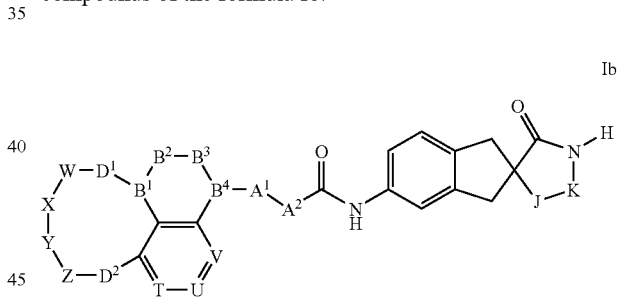

wherein $A^1$, $A^2$, $B^1$, $B^2$, $B^3$, $B^4$, $D^1$, $D^2$, J, K, T, U, V, W, X, Y, and Z are defined herein;
and pharmaceutically acceptable salts thereof and individual enantiomers and diastereomers thereof.

Another embodiment of the present invention includes compounds of the formula Ic:

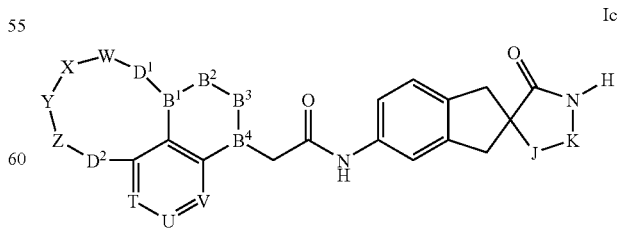

wherein $B^1$, $B^2$, $B^3$, $B^4$, $D^1$, $D^2$, J, K, T, U, V, W, X, Y, and Z are defined herein;
and pharmaceutically acceptable salts thereof and individual enantiomers and diastereomers thereof.

Another embodiment of the present invention includes compounds of the formula Id:

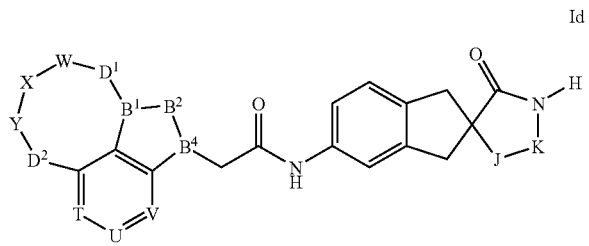

wherein $B^1$, $B^2$, $B^4$, $D^1$, $D^2$, J, K, T, U, V, W, X, and Y are defined herein;
and pharmaceutically acceptable salts thereof and individual enantiomers and diastereomers thereof.

Another embodiment of the present invention includes compounds of the formula Ie:

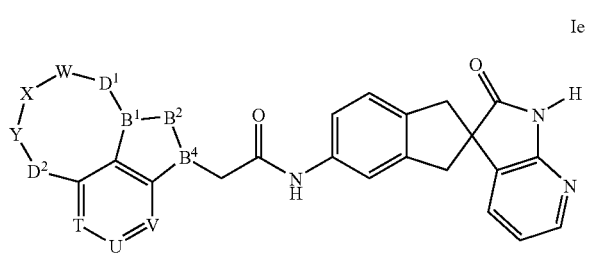

wherein $B^1$, $B^2$, $B^4$, $D^1$, $D^2$, T, U, V, W, X, and Y are defined herein;
and pharmaceutically acceptable salts thereof and individual enantiomers and diastereomers thereof. $B^1$ and $B^4$ are each independently selected from:

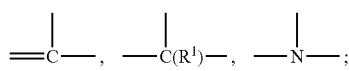

In an embodiment of the present invention $A^1$ is $CH_2$.
In an embodiment of the present invention $A^2$ is a bond.
In an embodiment of the present invention $B^1$ is selected from:

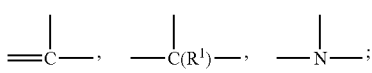

wherein $R^1$ is defined herein. In another embodiment of the present invention $B^1$ is selected from:

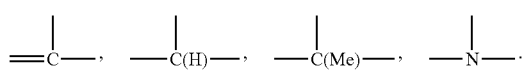

In an embodiment of the present invention $B^4$ is selected from:

In another embodiment of the present invention $B^4$ is

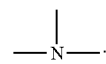

In an embodiment of the present invention $B^2$ is selected from:
$=C(R^1)$—; —$CR^1R^2$—; and —$C(=O)$—; wherein $R^1$ and $R^2$ are defined herein. In another embodiment of the present invention $B^2$ is selected from: $=C(H)$—; —$CH_2$—; and —$C(=O)$—.

In an embodiment of the present invention $B^3$ is a bond.
In an embodiment of the present invention $D^1$ is selected from:
—$CR^1R^2$—; and —$N(R^1)$—; wherein $R^1$ and $R^2$ are defined herein. In another embodiment of the present invention $D^1$ is selected from: —$CH_2$—; and —$N(H)$—. In yet another embodiment of the present invention $D^1$ is —$CH_2$—.

In an embodiment of the present invention $D^2$ is selected from:
—$CR^1R^2$—; and —$N(R^1)$—; wherein $R^1$ and $R^2$ are defined herein. In another embodiment of the present invention $D^2$ is selected from: —$CH_2$—; —$N(H)$—; and —$N(Me)$—. In yet another embodiment of the present invention $D^2$ is —$N(H)$—.

In an embodiment of the present invention T is selected from:
$=C(R^1)$—; and $=N$—; wherein $R^1$ is defined herein. In another embodiment of the present invention T is selected from: $=C(H)$—; and $=N$—.

In an embodiment of the present invention U is selected from:
$=C(R^1)$—; and $=N$—; wherein $R^1$ is defined herein. In another embodiment of the present invention U is selected from: $=C(H)$—; $=C(Me)$—; and $=N$—.

In an embodiment of the present invention V is $=C(H)$—.
In an embodiment of the present invention W is selected from:
a bond; —$CR^1R^2$—; and —$C(=O)$—; wherein $R^1$ and $R^2$ are defined herein. In another embodiment of the present invention W is selected from: a bond; —$CH_2$—; and —$C(=O)$—. In yet another embodiment of the present invention W is —$C(=O)$—.

In an embodiment of the present invention X is selected from:
a bond; —$CR^1R^2$—; and —$C(=O)$—; wherein $R^1$ and $R^2$ are defined herein. In another embodiment of the present invention X is selected from: a bond; —$CH_2$—; and —$C(=O)$—.

In an embodiment of the present invention Y is selected from:
a bond; —$CR^1R^2$—; and —$C(=O)$—; wherein $R^1$ and $R^2$ are defined herein. In another embodiment of the present invention Y is selected from: a bond; —$CH_2$—; and —$C(=O)$—.

In an embodiment of the present invention Z is selected from: a bond; —$CR^1R^2$—; and —$C(=O)$—; wherein $R^1$ and $R^2$ are defined herein. In another embodiment of the present invention Z is a bond.

In an embodiment of the present invention $R^1$ and $R^2$ are independently selected from:
(1) hydrogen; (2) —$C_{1-6}$alkyl, which is unsubstituted or substituted with 1-5 substituents each independently selected from:
(a) halo,
(b) hydroxy,
(c) —O—$C_{1-6}$alkyl,
(d) —$C_{3-6}$cycloalkyl, (e) phenyl or heterocycle, wherein heterocycle is selected from: azetidinyl, imidazolyl, oxazolyl, pyridyl, pyrimidinyl, pyrazinyl, piperidinyl, piperazinyl, pyrrolidinyl, thiazolyl, thienyl, triazolyl, tetrazolyl, tetrahydrofuryl and morpholinyl,
  which is unsubstituted or substituted with 1-3 substituents each independently selected from: —$C_{1-4}$alkyl, —O—$C_{1-4}$alkyl, halo, hydroxy, trifluoromethyl and —$OCF_3$,
(f) —$CO_2R^9$, wherein $R^9$ is independently selected from: hydrogen, and —$C_{1-4}$alkyl,
(g) —$NR^{10}R^{11}$, wherein $R^{10}$ and $R^{11}$ are each independently selected from:
  hydrogen, —$C_{1-4}$alkyl which is unsubstituted or substituted with 1-3 fluoro, —$COR^9$ and —$SO_2R^{12}$,
(h) —$CONR^{10a}R^{11a}$, wherein $R^{10a}$ and $R^{11a}$ are each independently selected from:
  hydrogen, —$C_{1-4}$alkyl which is unsubstituted or substituted with 1-3 fluoro, and —$C_{5-6}$cycloalkyl,
  or where $R^{10a}$ and $R^{11a}$ are joined to form a ring selected from azetidinyl, pyrrolidinyl, piperidinyl, piperazinyl and morpholinyl, which is unsubstituted or substituted with 1-3 substituents each independently selected from: —$C_{1-4}$alkyl, —O—$C_{1-4}$alkyl, halo and hydroxyl,
(i) —$(NR^{10a})CO_2R^9$,
(3) —$C_{3-6}$cycloalkyl, which is unsubstituted or substituted with 1-3 substituents each independently selected from: halo, hydroxy and —O—$C_{1-6}$alkyl,
(4) phenyl or heterocycle, wherein heterocycle is selected from: pyridyl, pyrimidinyl, pyrazinyl, thienyl, pyrrolidinyl, azetidinyl, thiazolyl, oxazolyl, isoxazolyl, imidazolyl, triazolyl, tetrazolyl, benzimidazolyl, benzoxazolyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, quinazolinyl, tetrahydrofuryl, naphthyridinyl, quinoxalinyl, 1,3-dioxolanyl, oxadiazolyl, piperidinyl, tetrahydropyranyl, and morpholinyl, which is unsubstituted or substituted with 1-3 substituents each independently selected from: —$C_{1-4}$alkyl which is unsubstituted or substituted with 1-3 fluoro, —O—$C_{1-4}$alkyl, which is unsubstituted or substituted with 1-6 fluoro, halo, hydroxy, —$C_{3-6}$cycloalkyl, —$CO_2R^9$, —$NR^{10}R^{11}$ and —$CONR^{10}R^{11}$,
(5) halo,
(6) hydroxy,
(7) —O—$C_{1-4}$alkyl, which is unsubstituted or substituted with 1-3 halo,
(8) —CN,
(9) —$CO_2R^9$,
(10) —$NR^{10}R^{11}$,
(11) —$CONR^{10a}R^{11a}$, and
(12) —$(NR^{10a})CO_2R^9$.
In an embodiment of the present invention $R^1$ and $R^2$ are independently selected from:
(1) hydrogen;
(2) —$C_{1-4}$alkyl which is unsubstituted or substituted with 1-3 substituents each independently selected from:
  (a) halo,
  (b) —O—$C_{1-4}$alkyl,
  (c) phenyl or heterocycle, wherein heterocycle is selected from: azetidinyl, oxazolyl, pyridyl, pyrimidinyl, pyrazinyl, piperidinyl, piperazinyl, pyrrolidinyl, tetrahydrofuryl and morpholinyl, which phenyl or heterocycle is unsubstituted or substituted with 1-3 substituents each independently selected from: —$C_{1-4}$alkyl, —O—$C_{1-4}$alkyl, halo and hydroxy,
  (d) —$CO_2R^9$,
  (e) —$NR^{10}R^{11}$,
  (f) —$CONR^{10a}R^{11a}$,
(3) —$C_{3-6}$cycloalkyl,
(4) phenyl or heterocycle, wherein heterocycle is selected from: pyridyl, pyrimidinyl, pyrazinyl, pyrrolidinyl, azetidinyl, oxazolyl, imidazolyl, 2-oxopiperazinyl, 2-oxopiperidinyl, 2-oxopyrrolidinyl, tetrahydrofuryl, oxadiazolyl, piperidinyl and morpholinyl, which phenyl or heterocycle is unsubstituted or substituted with 1-3 substituents each independently selected from: —$C_{1-4}$alkyl which is unsubstituted or substituted with 1-3 fluoro, halo, hydroxy, —O—$C_{1-4}$alkyl, —$C_{3-6}$cycloalkyl, —$NR^{10}R^{11}$ and —$CONR^{10}R^{11}$,
(5) halo,
(6) hydroxy,
(7) —O—$C_{1-4}$ alkyl, which is unsubstituted or substituted with 1-3 halo,
(8) —CN,
(9) —$CO_2R^9$,
(10) —$NR^{10}R^{11}$,
(11) —$CONR^{10a}R^{11a}$, and
(12) —$(NR^{10a})CO_2R^9$;
where $R^9$ is selected from: hydrogen, and —$C_{1-4}$alkyl,
where $R^{10}$ and $R^{11}$ are each independently selected from:
  hydrogen and —$C_{1-4}$alkyl which is unsubstituted or substituted with 1-3 fluoro, and
where $R^{10a}$ and $R^{11a}$ are each independently selected from:
  hydrogen and —$C_{1-4}$alkyl which is unsubstituted or substituted with 1-3 fluoro, or where $R^{10a}$ and $R^{11a}$ are joined to form a ring selected from azetidinyl, pyrrolidinyl, piperidinyl, piperazinyl and morpholinyl, In an embodiment of the present invention J is selected from:
=$C(R^{6a})$—; and —$CH_2$—; wherein $R^{6a}$ is defined herein. In another embodiment of the present invention J is —$CH_2$—. In yet another embodiment of the present invention J is =$C(R^{6a})$—; wherein $R^{6a}$ is defined herein.

In an embodiment of the present invention K is selected from:
=$C(R^{6b})$—; —$CH_2$—; and —$C(=O)$—; wherein $R^{6b}$ is defined herein. In another embodiment of the present invention K is —$CH_2$—. In yet another embodiment of the present invention K is =$C(R^{6b})$— wherein $R^{6b}$ is defined herein.

In an embodiment of the present invention $R^4$ is selected from: hydrogen and —$C_{1-6}$alkyl, which is unsubstituted or substituted with fluoro. In another embodiment of the present invention $R^4$ is hydrogen.

In an embodiment of the present invention $R^{5a}$, $R^{5b}$ and $R^{5c}$ are independently selected from hydrogen, $C_{1-6}$alkyl and halo. In another embodiment of the present invention $R^{5a}$, $R^{5b}$ and $R^{5c}$ are independently selected from hydrogen and halo. In yet another embodiment of the present invention $R^{5a}$, $R^{5b}$ and $R^{5c}$ are hydrogen.

In an embodiment of the present invention $R^{6a}$ and $R^{6b}$ are independently selected from:
(1) hydrogen;
(2) —$C_{1-4}$alkyl which is unsubstituted or substituted with 1-3 substituents each independently selected from: halo, —O—$C_{1-6}$alkyl, —$C_{3-6}$cycloalkyl, and phenyl,
(3) phenyl or heterocycle, wherein heterocycle is selected from: pyridyl, pyrimidinyl, pyrazinyl, thiazolyl, oxazolyl, tetrahydrofuryl, piperidinyl and morpholinyl, which phenyl or heterocycle is unsubstituted or substituted with 1-3 substituents each independently selected from: halo, hydroxy, —C$_{1-4}$alkyl which is unsubstituted or substituted with 1-3 fluoro, and —O—C$_{1-4}$alkyl which is unsubstituted or substituted with 1-3 fluoro, (4) halo, (5) —NR$^{10}$R$^{11}$, (6) hydroxy, (7) —O—C$_{1-4}$alkyl which is unsubstituted or substituted with 1-3 halo.

In another embodiment of the present invention R$^{6a}$ and R$^{6b}$ are each independently selected from: hydrogen, —C$_{1-4}$alkyl which is unsubstituted or substituted with 1-3 fluoro, and phenyl or heterocycle wherein heterocycle is selected from: pyridyl, pyrimidinyl, pyrazinyl, thiazolyl, oxazolyl, tetrahydrofuryl, piperidinyl, and morpholinyl.

In yet another embodiment of the present invention R$^{6a}$ and R$^{6b}$ and the atom(s) to which they are attached are joined to form a ring selected from phenyl, pyridyl, pyrimidinyl, pyrazinyl, pyridazinyl, thiazolyl, oxazolyl, imidazolyl and thienyl, which ring is unsubstituted or substituted with 1-3 substituents each independently selected from:

(a) —C$_{1-4}$alkyl which is unsubstituted or substituted with 1-3 substituents each independently selected from: halo, —O—C$_{1-6}$alkyl, —CO$_2$R$^9$, —NR$^{10}$R$^{11}$ and —CONR$^{10a}$R$^{11a}$, (b) phenyl or heterocycle, wherein heterocycle is selected from: pyridyl, pyrimidinyl, pyrazinyl, pyrrolidinyl, azetidinyl, piperidinyl and morpholinyl, which phenyl or heterocycle is unsubstituted or substituted with 1-3 substituents each independently selected from: —C$_{1-4}$alkyl, which is unsubstituted or substituted with 1-5 fluoro, —O—C$_{1-4}$alkyl, which is unsubstituted or substituted with 1-3 fluoro, halo and hydroxy, (c) halo, (d) hydroxy, (e) —O—C$_{1-6}$alkyl which is unsubstituted or substituted with 1-5 halo, (f) —CN, (g) —NR$^{10}$R$^{11}$, (h) —CONR$^{10a}$R$^{11a}$, and (i) oxo.

In an alternate embodiment of the present invention R$^{6a}$ and R$^{6b}$ and the atom(s) to which they are attached are joined to form a ring selected from phenyl, pyridyl and pyrimidinyl, which ring is unsubstituted or substituted with 1-3 substituents each independently selected from: —C$_{1-4}$alkyl which is unsubstituted or substituted with 1-3 fluoro, halo, hydroxy and —O—C$_{1-4}$alkyl. In certain embodiments of the present invention R$^{6a}$ and R$^{6b}$ and the atom(s) to which they are attached are joined to form a ring selected from pyridyl, and pyrimidinyl.

In an embodiment of the present invention m is 1.

In an embodiment of the present invention n is 1.

In an embodiment of the present invention n is 2.

It is to be understood that where one or more of the above recited structures or substructures recite multiple substituents having the same designation each such variable may be the same or different from each similarly designated variable.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the R$^{10a}$ and R$^{11a}$ substituents, or other substituents which are said to form rings, are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus C$_{1-6}$alkyl is defined to identify the group as having 1, 2, 3, 4, 5 or 6 carbons in a linear or branched arrangement, such that C$_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. C$_0$ or C$_0$alkyl is defined to identify the presence of a direct covalent bond.

The term "alkynyl" means linear or branched structures and combinations thereof, of the indicated number of carbon atoms, having at least one carbon-to-carbon triple bond. Thus C$_{2-6}$alkynyl is defined to identify the group as having 2, 3, 4, 5 or 6 carbons in a linear or branched arrangement, such that C$_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 4- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydropyran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The terms "bond" and "absent" are in certain instances herein used interchangeably to refer to an atom (or chemical moiety) which is not present in a particular embodiment of the invention. In such embodiments, the atoms adjacent the "bond" or "absent" atom are simply bonded to one another. For example, in certain embodiments of the invention described and claimed herein, where $A^2$ is described as "absent". In such a molecule, it is understood that $A^1$ is bonded directly to the —C(=O) moiety, resulting in the sub-structure $B^4$-$A^1$-C(=O). The absence of a specific atom or moiety, particularly an atom or moiety which serves to link or connect other atoms or moieties, does not imply that such other atoms or moieties are not linked.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 μg) were incubated in 1 ml of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 μl) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 μg/ml streptomycin at 37° C., 95% humidity, and 5% CO$_2$. For cAMP assays, cells were plated at 5×10$^5$ cells/well in 96-well poly-D-lysine-coated plates (Becton-Dickinson) and cultured for ~18 h before assay. Cells were washed with phosphate-buffered saline (PBS, Sigma) then pre-incubated with 300 μM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HESS. Stable cell line generation was accomplished by co-transfecting 10 ug of DNA with 30 ug Lipofectamine 2000 (Invitrogen) in 75 cm$^2$ flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HUES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{(Y_{max} - Y_{min}(\% \ I_{max} - \% \ I_{min}/100) + Y_{min} + (Y_{max} - Y_{min})(100 - \% \ I_{max}/100))}{1 + ([Drug]/K_i(1 + [Radiolabel]/K_d)^{nH}}$$

Where Y is observed CPM bound, Y$_{max}$ is total bound counts, Y min is non specific bound counts, (Y max−Y min) is specific bound counts, % I max is the maximum percent inhibition, % I min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 μM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and IC$_{50}$ values determined from a 4-parameter logistic fit as defined by the equation y=((a−d)/(1+(x/c)$^b$)+d, where y=response, x=dose, a=max response, d=min response, c=inflection point and b=slope.

In particular, the compounds of the following examples had activity as antagonists of the CGRP receptor in the aforementioned assays, generally with a K$_i$ or IC$_{50}$ value of less than about 50 μM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of aniline intermediates may be conducted as described in Schemes 1-5. Aniline intermediates bearing $R^{5a}$, $R^{5b}$ and $R^{5c}$ may be prepared by employing appropriately substituted starting materials or by derivatization of any intermediates and/or final products as desired by methods known in the art.

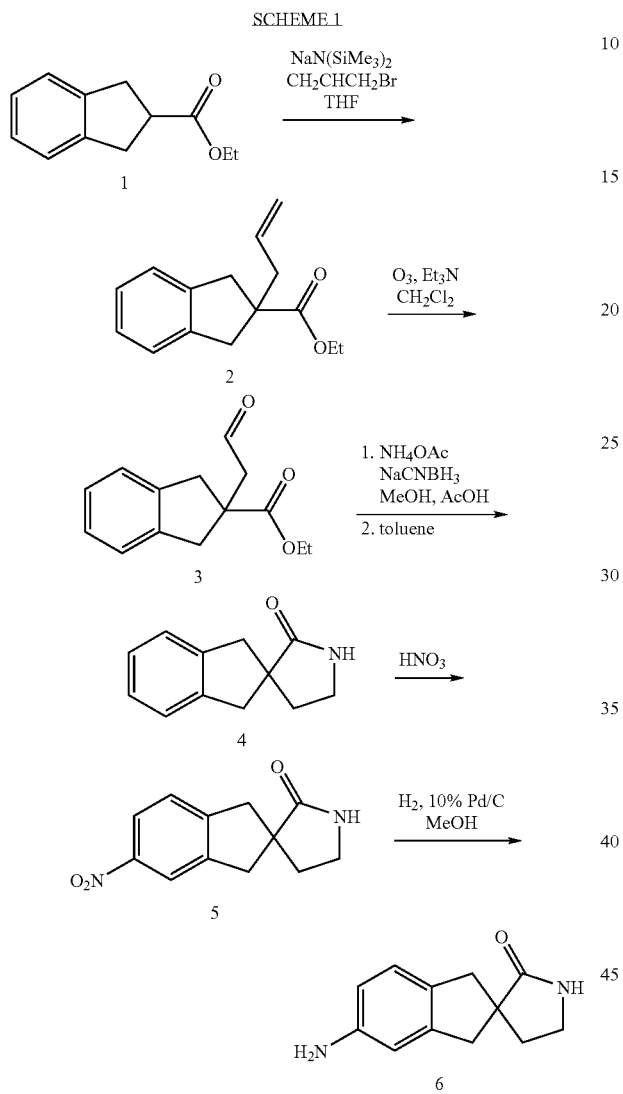

The synthesis of a representative spirolactam aniline (6) is illustrated in Scheme 1. The known ethyl indane-2-carboxylate (1, Schaaf et al., *J. Med. Chem.* 1983, 26, 328-334) may be alkylated using allyl bromide and sodium bis(trimethylsilyl)amide to form 2. Oxidation of the allyl group with ozone can produce the aldehyde 3, which cyclizes to the lactam 4 after treatment with ammonium acetate and sodium cyanoborohydride and heating in toluene. The reductive amination of aldehyde 3 with amines other than ammonia may be used to provide a variety of N-protected analogues of lactam 4, which may facilitate subsequent chemical steps prior to removal of the lactam protecting group. The intermediate lactam may be nitrated, for example using 70% nitric acid, and the resulting nitro compound 5 can be reduced to provide the aniline intermediate 6, using a variety of well known methodologies, such as catalytic hydrogenation. Those skilled in the art of organic synthesis will recognize that straightforward modifications of this methodology may be used to access other spirolactam intermediates, such as those with other lactam ring sizes. Additionally, use of an alternative starting material to the indane 1 may be used to provide different products, such as tetralin-based spirolactams.

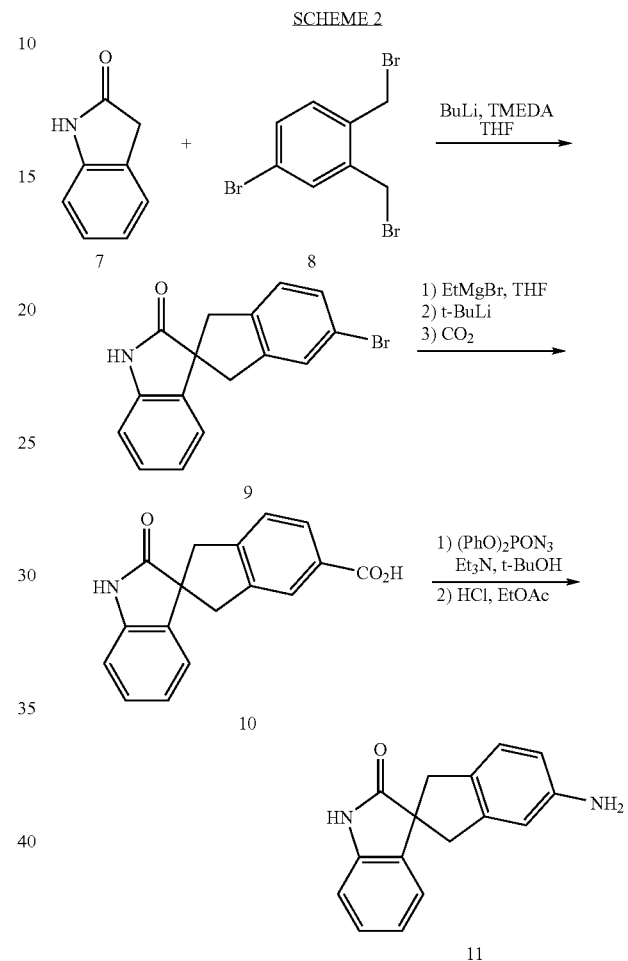

In Scheme 2, an example of the synthesis of a spirooxindole intermediate is shown. Treatment of oxindole (7) with butyllithium and tetramethylethylenediamine, followed by a dihalide or its equivalent, e.g. 4-bromo-1,2-bis(bromomethyl)benzene [Anderson et al., *J. Org. Chem.* 1979, 44(9), 1519-1533], leads to the spirooxindole 9. The bromide may be converted to a carboxylic acid (10) by treatment with ethylmagnesium bromide and tert-butyllithium, and quenching of the resulting organolithium species with carbon dioxide. A Curtius rearrangement using diphenylphosphoryl azide in tert-butanol, followed by deprotection with hydrochloric acid can provide the aniline 11. Alternative conditions, such as treatment of acid 10 with sodium azide in concentrated sulfuric acid, may also be used to provide aniline 11.

Scheme 3 illustrates a route to spiroimide derivative 16, using methodology that is similar to that shown in Scheme 1. Ethyl indane-2-carboxylate (1) may be alkylated with tert-butyl bromoacetate to form the diester 12. Subjection of 12 to basic, then acidic, hydrolysis conditions can provide the diacid 13. Treatment of the diacid 13 with a number of different reagents can provide imide 14 or a derivative thereof. In Scheme 3, heating 13 in the presence of acetyl chloride, followed by reaction with ammonia affords spiroimide 14. Reaction with sodium nitrite in trifluoroacetic acid, followed by hydrogenation over palladium can provide the aniline 16.

Reduction of the nitro compound 22, for example using hydrogenation over palladium, and a two-step deprotection affords the corresponding aniline 24. The methodology shown in Scheme 4 is not limited to azaoxindoles such as 20, but may be applied to a variety of suitably protected heterocyclic systems to give the corresponding spiro compounds.

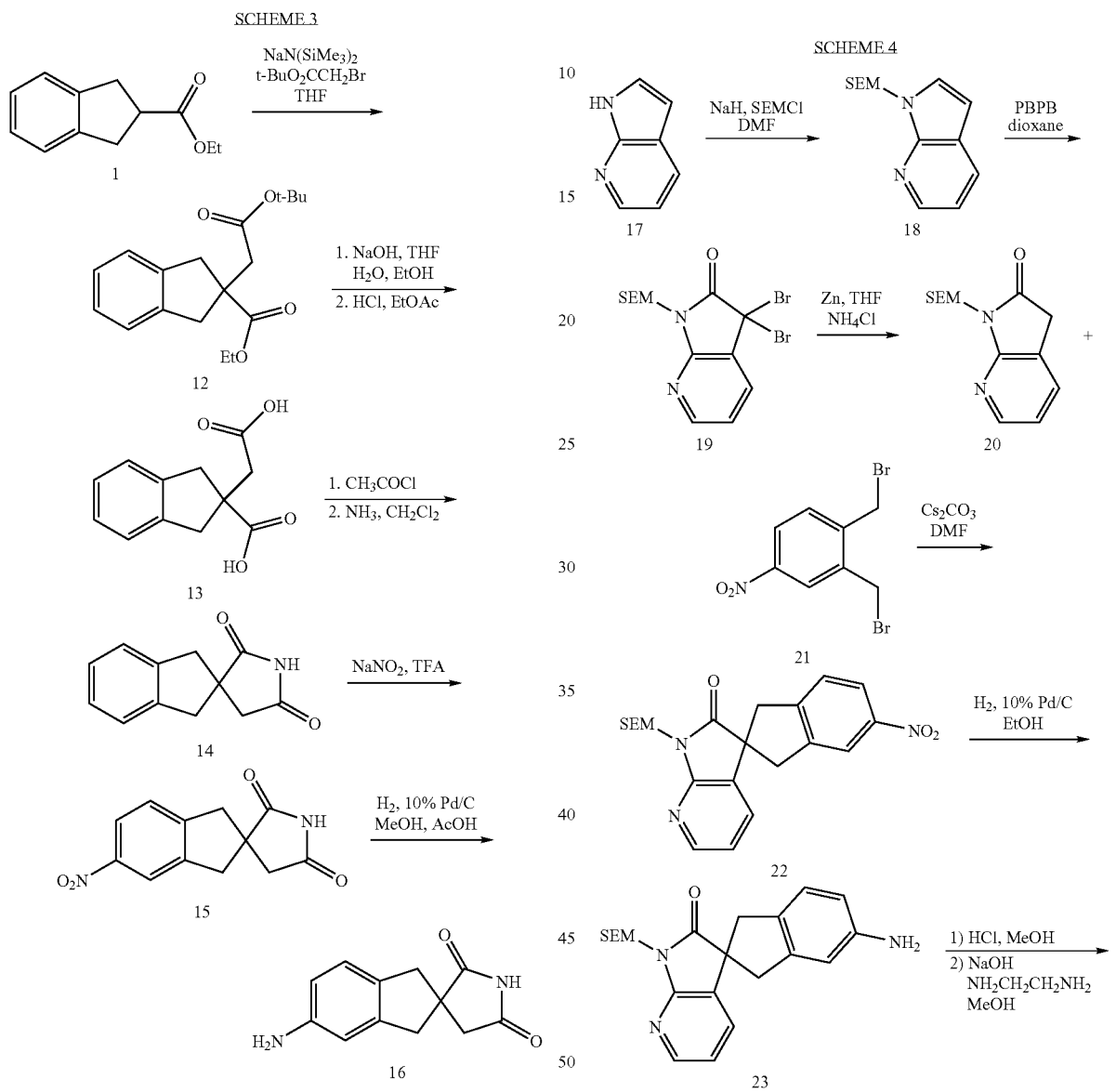

A representative synthesis of a spiroazaoxindole intermediate is shown in Scheme 4. 7-Azaindole (17) may be protected with a variety of protecting groups, such as the (trimethylsilyl)ethoxymethyl group shown in Scheme 4. Following the method of Marfat and Carter (*Tetrahedron Lett.*, 1987, 28, 4027-4030), treatment of 18 with pyridine hydrobromide perbromide provides the dibromoazaoxindole 19, which may be reduced to the corresponding azaoxindole 20 by reaction with zinc. The key alkylation of 20 with 1,2-bis(bromomethyl)-4-nitrobenzene (21, Cava et al., *J. Org. Chem.* 2000, 65, 5413-5415) is carried out using cesium carbonate in DMF to afford the spiroazaoxindole 22. A variety of other bases and solvents may be employed in this alkylation reaction, and use of a different alkylating agent than the dibromide shown here can lead to other products.

Spiroazaoxindole intermediates, such as those illustrated in Scheme 4, may be resolved to give pure enantiomers using techniques familiar to those skilled in the art. For example, chromatography of the protected intermediate 23 on a Chiral-Pak OD column can be used to provide the individual enantiomers (+)-23 and (−)-23, and these enantiomers may be converted to the corresponding anilines [(+)-24 and (−)-24] by the two-step deprotection. In the case of compound 24, the dextro isomer is the (R)-enantiomer and the levo isomer (S)-enantiomer, i.e. (+)-24 is (R)-24 and (−)-24 is (S)-24. Use of standard coupling procedures using enantiomerically pure anilines can provide the individual enantiomers of the final products. Resolution may be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

As an example of related methodology to that described in Scheme 4, using alternative conditions for the alkylation reaction, the synthesis of spirodiazaoxindole compounds is outlined in Scheme 5. Published methodology is used to convert 6-chloro-deazapurine into 4-chloro-diazaoxindole 25, the starting material in Scheme 5 (Sun et al., *Biorg. Med. Chem Lett.* 2002, 12, 2153-2157).

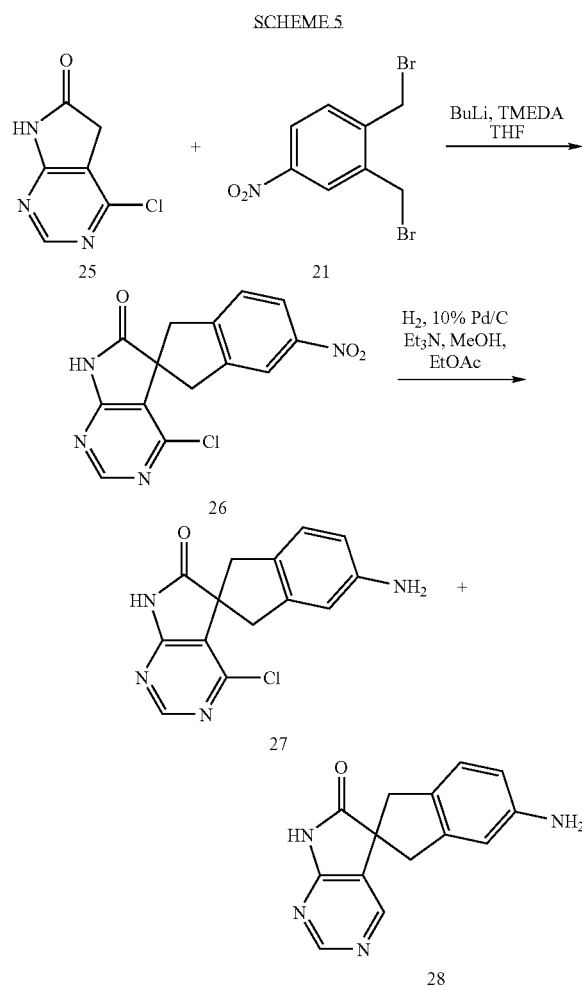

Alkylation with dibromide 21 under similar conditions to that shown in Scheme 2 may provide the spirodiazaoxindole 26. Hydrogenation at 30 psi for two hours can provide the aniline 27, while hydrogenation at higher pressure (55 psi) and longer reaction time (180 hours) can provide the deschloro analogue 28.

Aniline intermediates, such as those described in Schemes 1-5, may be coupled with a variety of carboxylic acids, or carboxylic acid derivatives, to provide amide final products.

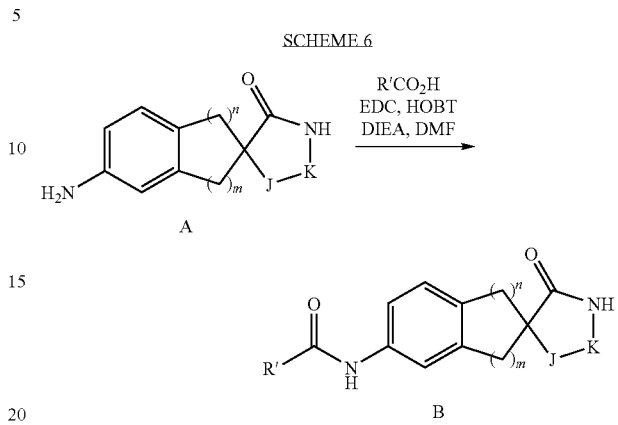

Thus, coupling of amine A with a carboxylic acid, R'CO$_2$H, can be used to give amide B. Other standard coupling conditions may be employed in the synthesis of such amides, such as use of an alternative coupling reagent like PyBOP, or activation of the carboxylic acid as an acid anhydride or acid chloride. Ureas may also be synthesized from aniline A and an appropriate amine by use of phosgene, 1,1'-carbonyldiimidazole, 4-nitrophenyl chloroformate, or a similar reagent.

Most of the acids (R'CO$_2$H), used to make the compounds of the present invention are readily available. They may be obtained from commercial sources or synthesized by methodology familiar to those skilled in the art and as described in the chemical literature. A number of the acids were synthesized using the methodology outlined in Schemes 7-12.

Scheme 7 illustrates a general route to substituted benzimidazolone tricyclic carboxylic acid I. Starting with the appropriately substituted 3-nitro-1,2-phenylenediamine starting material C, which may be obtained from a variety of published routes and known methodologies (*Leibigs Ann. Chem.* 1989, 539-544; *J. Med. Chem.* 1995, 38, 4367-4379), the nitrobenzimidazolone D may be synthesized by treatment with phosgene or one of a number of carbonylation reagents, including carbonyldiimidazole and urea. Alternatively, a substituted benzimidazolone may be nitrated in order to provide D (*J. Org. Chem.* 1995, 60, 1565-1582).

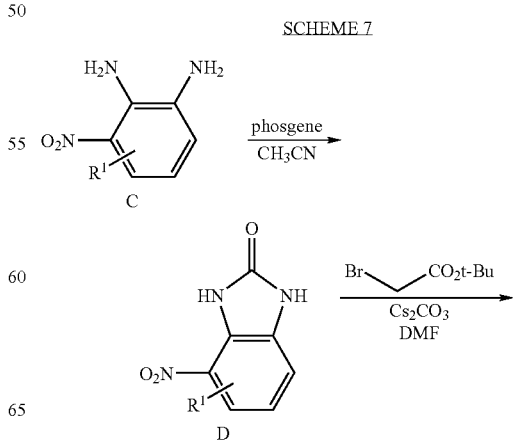

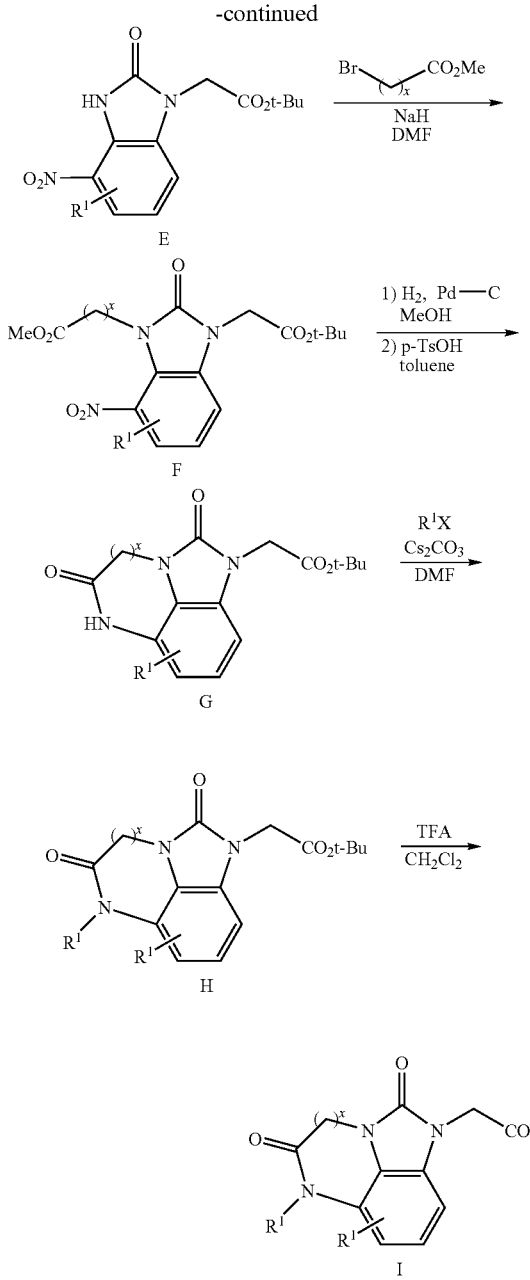

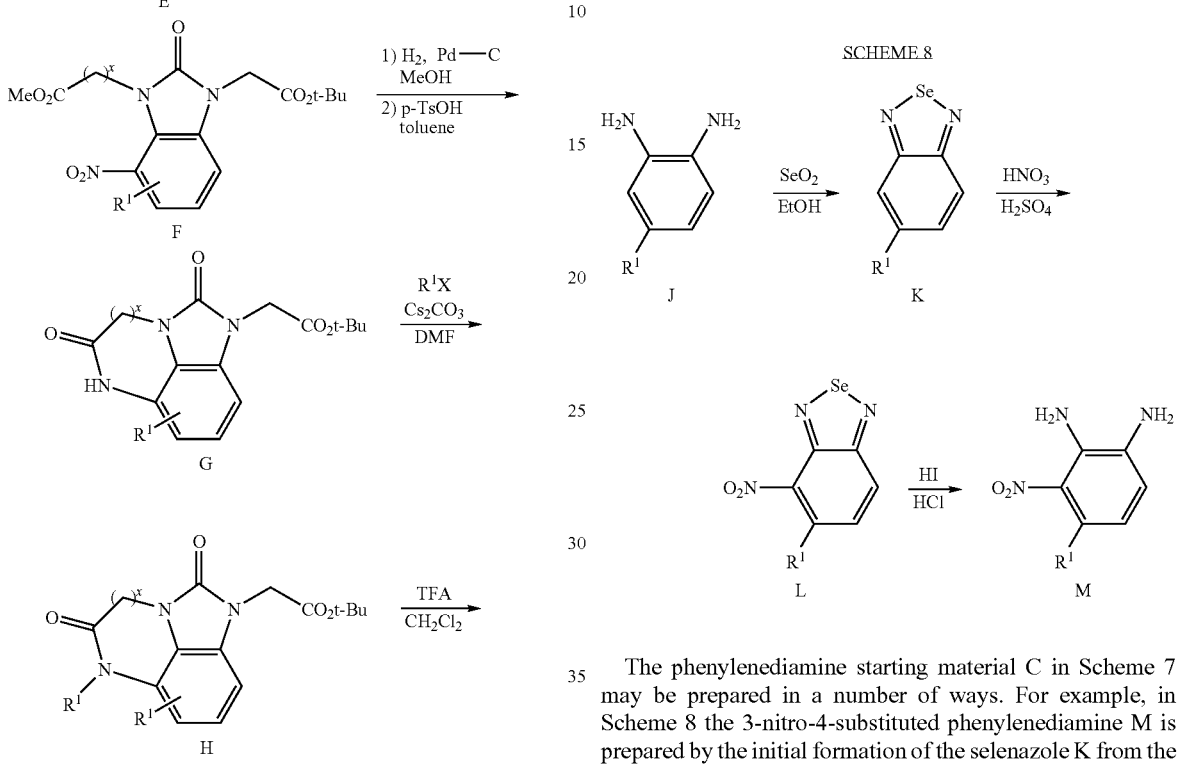

tively, the anilide nitrogen may be arylated using well-precedented methodology, such as treatment with an aryl bromide and a copper or palladium catalyst (*Org. Lett.* 2000, 2, 1101-1104; *J. Am. Chem. Soc.* 2001, 123, 7727-7729). Hydrolysis of the ester to reveal the acid functionality in I can be accomplished using either acidic or basic conditions, depending upon the nature of the ester intermediate H. In Scheme 7, the tert-butyl ester is removed using trifluoroacetic acid.

The phenylenediamine starting material C in Scheme 7 may be prepared in a number of ways. For example, in Scheme 8 the 3-nitro-4-substituted phenylenediamine M is prepared by the initial formation of the selenazole K from the 4-substituted 1,2-phenylenediamine J (*J. Med. Chem.* 1995, 38, 4367-4379). The selenazole undergoes nitration selectively at the 3-position with standard reagents, such as a combination of nitric and sulfuric acid, to give L. Removal of the selenazole using a mixture of hydroiodic and hydrochloric acid yields the phenylenediamines, which may be used as starting materials in the synthesis of tricyclic carboxylic acids I.

Alkylation of the nitrobenzimidazolone D under basic conditions with a suitable bromoacetate, such as tert-butyl bromoacetate, can afford the monoacetyl derivative E. Further alkylation of the benzimidazolone is accomplished using, for example, sodium hydride as base followed by a suitable bromide to give the benzimidazolone F. In the example shown, bromo esters with different chain lengths may be used to provide a number of different products. In some cases, depending upon the selection of $R^1$, these alkylations may result in mixtures of regioisomers, and the mixtures of E or F can be separated by chromatography. Reduction of the nitro compound F to the corresponding aniline may be accomplished via a number of standard methods, such as catalytic hydrogenation, and the aniline may be cyclized to give anilide G under acidic conditions. In Scheme 7, the resultant anilide is N-alkylated to give H. For example, when $R^1X$ is iodomethane, the N-methyl analogue is obtained. Alterna-

SCHEME 9

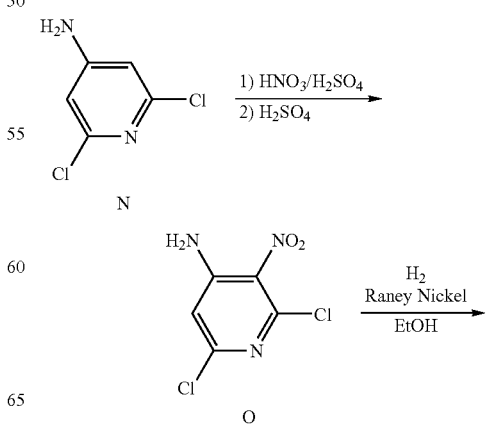

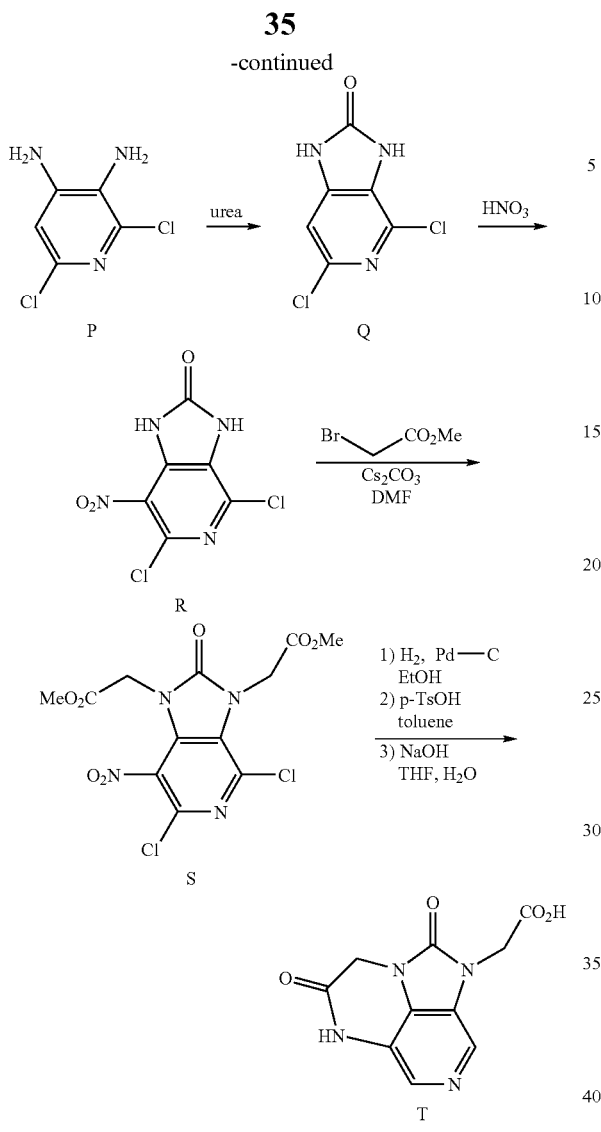

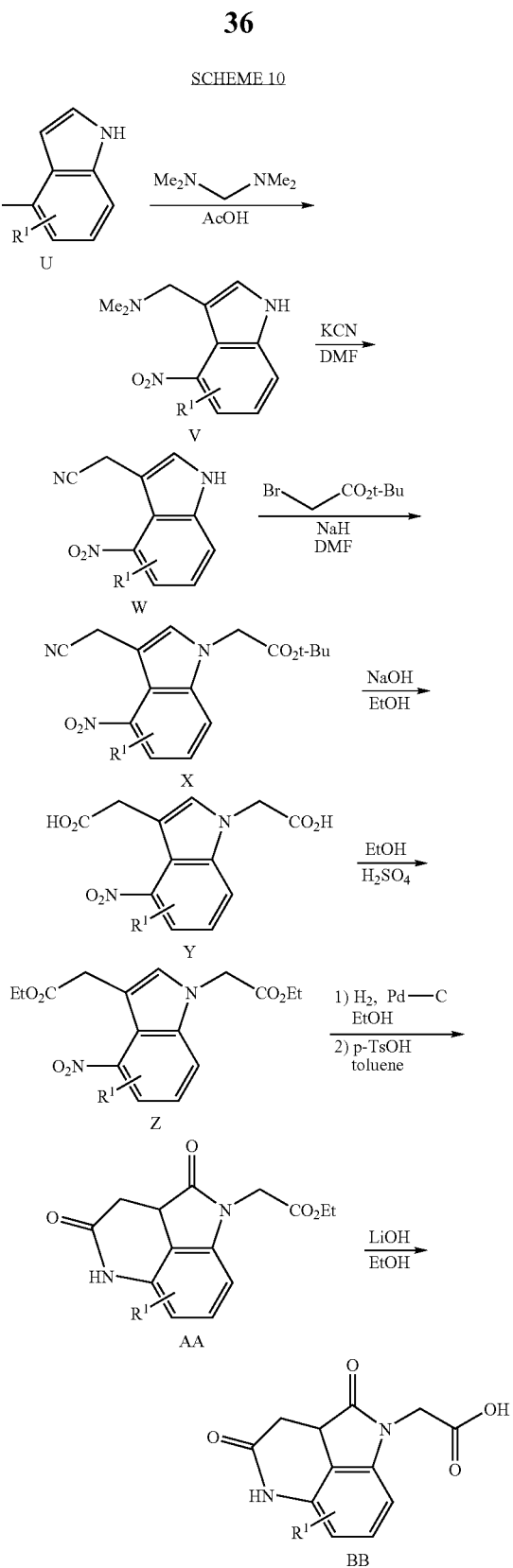

A representative synthesis of an azabenzimidazolone intermediate is illustrated in Scheme 9. Nitration of 4-amino-2,6-dichloropyridine (N) is accomplished by treatment with a mixture of nitric acid and sulfuric acid mixture followed by heating in sulfuric acid (*J. Het. Chem.* 1965, 2, 196). The nitroaniline O is reduced to the 1,2-diamine P, using Raney nickel in order to leave the chloro substituents intact. The benzimidazolone Q is formed by treatment of P with a urea melt at 165° C. Q can be nitrated under standard conditions to give compound R, which may be bis-alkylated using cesium carbonate and a bromoacetate in order to provide the diester S. Simultaneous removal of the aryl chloro substituents and reduction of the nitro group can be achieved by hydrogenation over a palladium catalyst. The synthesis is completed by cyclization of the resulting aminopyridine under acidic conditions, followed by saponification of the methyl ester moiety in order to provide the acid T. Using chemical procedures outlined previously and familiar to those skilled in the art, the chemistry in Scheme 9 may be modified in a number of ways in order to provide isomeric azabenzimidazolone intermediates. For example, when 1,3-dihydro-2H-imidazo[4,5-c]pyridin-2-one is reacted with nitric acid, the major product is 4-nitro-1,3-dihydro-2H-imidazo[4,5-c]pyridin-2-one, which may be chemically modified in the same fusion as R-T above to give another regioisomer of the azabenzimidazolone T.

Scheme 10 illustrates a general route to substituted indole tricyclic derivative BB. The nitroindole U can be converted to the nitrile W via a two-step sequence: a Mannich reaction with N,N,N',N'-tetramethyldiaminomethane followed by treatment with potassium cyanide. Alternatively, the dimethylamine derivative V can be formed by reaction of the nitroindole U with dimethylamine and formaldehyde in a microwave reactor. N-alkylation of W can be accomplished by treatment with an appropriate alkylating agent under basic conditions to give esters of the general form X. Treatment of X with excess sodium hydroxide may be used to hydrolyze both the nitrile and ester groups, to afford the diacid Y. Subjection of this diacid to classical esterification using EtOH and $H_2SO_4$ converts it to the corresponding diester Z. The nitro moiety may be reduced under a variety of conditions, such as catalytic hydrogenation, and the resulting aniline can be heated under acidic conditions to afford the tricyclic indole AA. Saponification of the ester is thereafter accomplished under standard conditions to provide the acid intermediate BB.

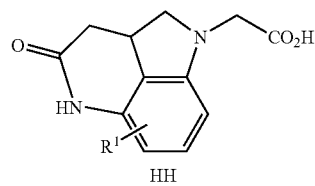

The preparation of substituted indoline tricyclic derivatives is outlined in Scheme 11. Acylation of nitroindole U using Vilsmeier methodology yields the 3-substituted indole CC. Simultaneous reduction of the ketone and the indole may be accomplished using triethylsilane under acidic conditions to afford the indoline DD. N-Alkylation of DD can be achieved by treatment with excess ethyl bromoacetate in the presence of potassium carbonate and potassium iodide to give the ester EE. Further elaboration of EE may be carried out in analogy with previous schemes to provide the indoline acid intermediate HH.

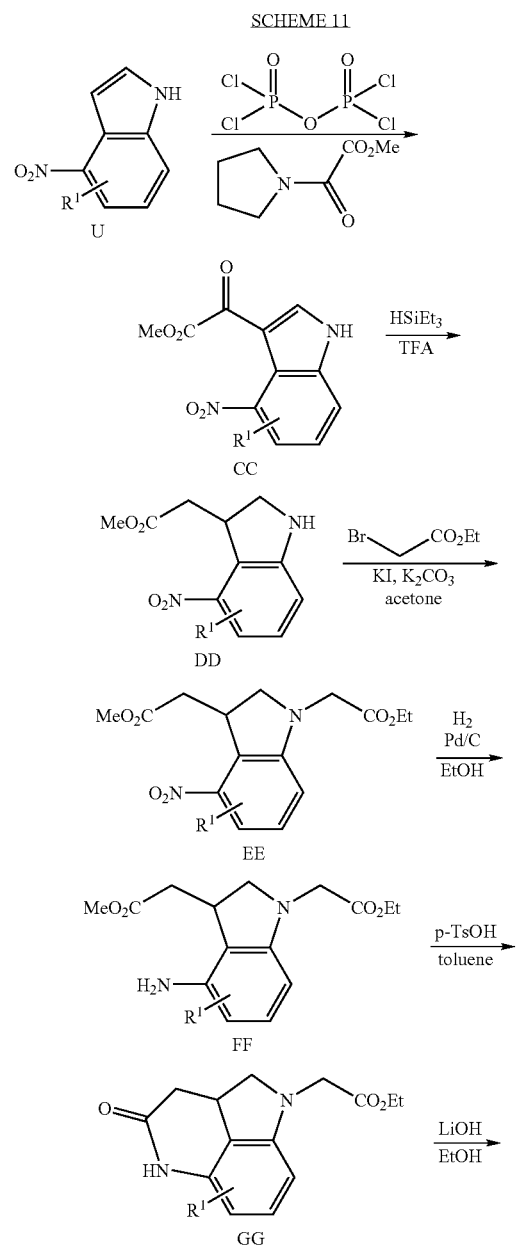

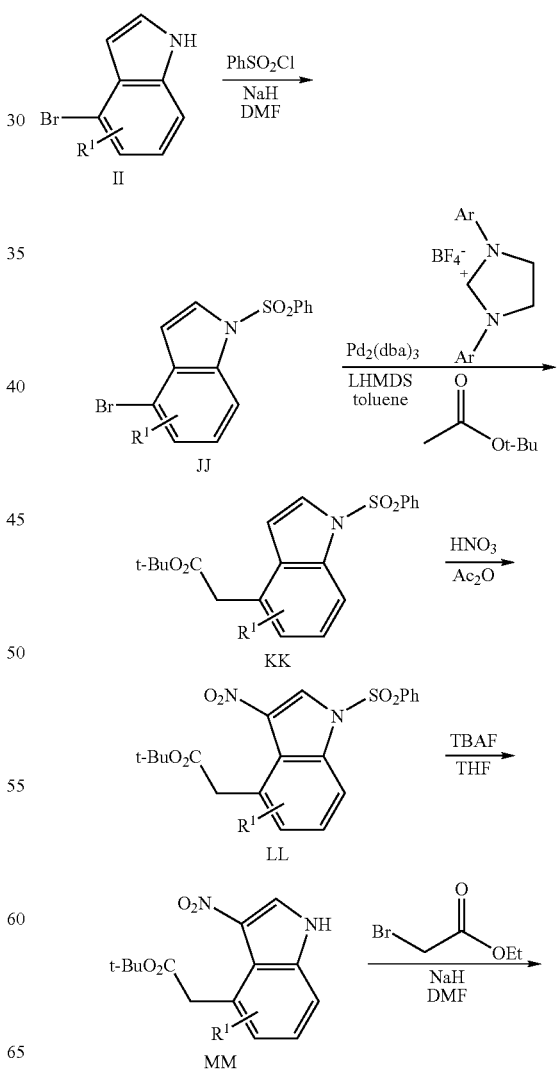

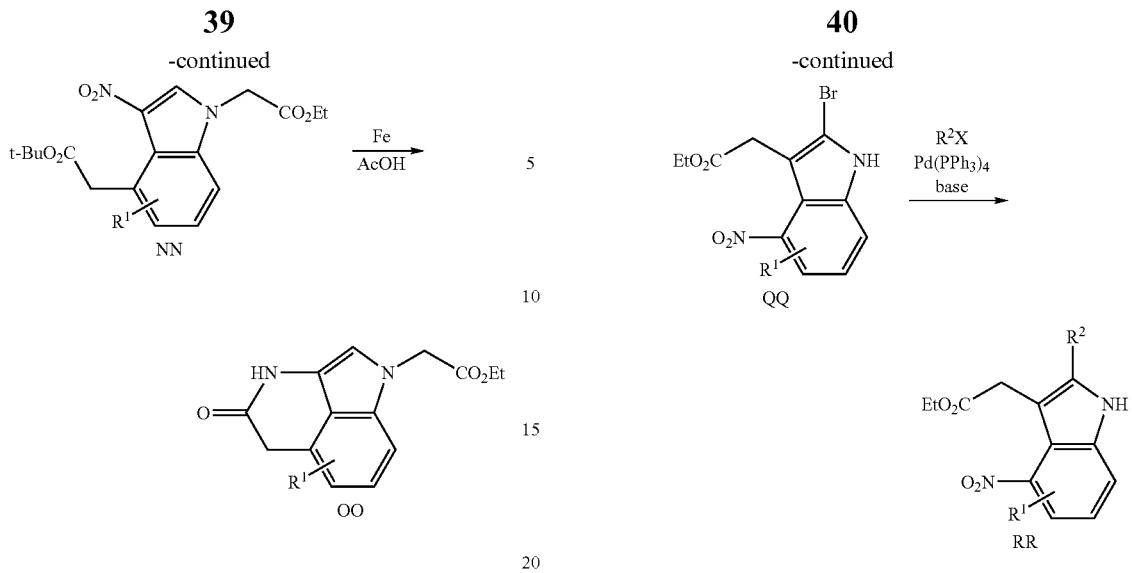

Methodology for the synthesis of indole tricyclic derivatives of the type OO is shown in Scheme 12. The N-protected bromoindole JJ is subjected to a palladium-catalyzed coupling reaction (*J. Am. Chem. Soc.* 2002, 124, 12557-12565) to afford the substituted indole KK. Nitration at the 3-position of the indole is accomplished by treatment with nitric acid in acetic anhydride. The sulfonamide protective group is removed from the indole and a similar alkylation methodology to that described in previous schemes is employed to yield the diester NN. Reduction of the nitro group and cyclization is accomplished in one pot using iron in acetic acid to provide OO, which may be saponified under standard conditions to provide the acid intermediate of interest.

Indole and indoline compounds such as those in Schemes 10-12 may be substituted or derivatized in a variety of ways. For example, classical Fischer indole syntheses, as well as variations familiar to those skilled in the art of organic synthesis, may be used to provide a variety of suitable indole starting materials. Another possible strategy is illustrated in Scheme 13, in which a 2-bromoindole derivative is further modified using a palladium mediated coupling. Hydrolysis of nitrile W followed by esterification provides indole PP, which may be brominated using N-bromosuccinimide. The resulting 2-bromoindole QQ may be useful in a variety of coupling methodologies, such as Suzuki couplings when $R^2X$ is a boronic acid, to provide 2-substituted indoles.

Scheme 14 illustrates a route to the tricyclic indoline WW. The 4-nitroindole U may be oxidized using N-chlorosuccinimide, followed by treatment with phosphoric acid in acetic acid to give the corresponding oxindole SS. A one-pot trialkylation procedure in DMF, using sodium hydride as base, can be used to provide the diester intermediate TT. A variety of $R^2$ substituents may be incorporated using this method. For example, when $R^2X$ is iodomethane the 3-methyloxindole derivative (TT; $R^2$=Me) is obtained. Treatment of oxindole TT with Lawesson's reagent can provide the corresponding thioamide UU, and simultaneous reduction of the nitro group and the thioamide using, for example, activated Raney nickel leads to the aniline VV. Cyclization of VV, usually carried out by heating in xylenes in the presence of acid, followed by saponification of the intermediate ester, affords the tricyclic indoline WW.

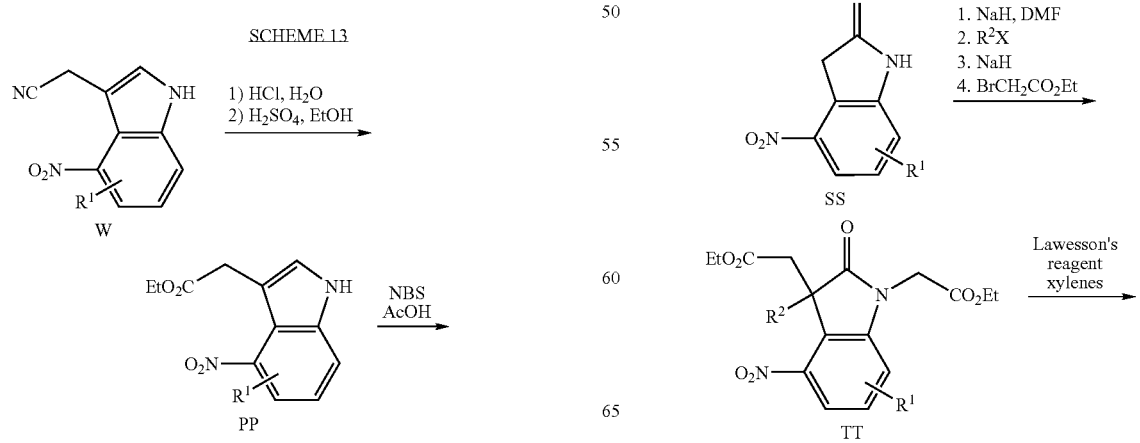

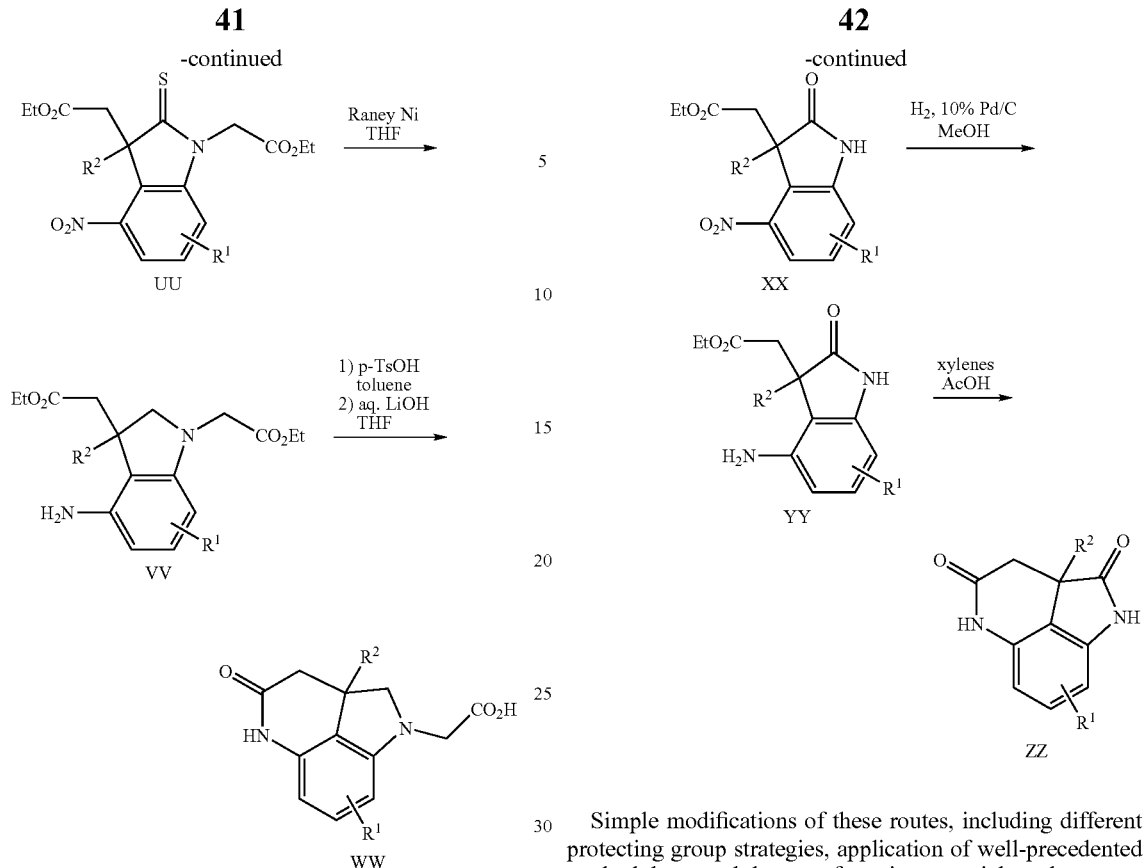

In Scheme 15, chemistry related to that shown in Scheme 14 is utilized to provide analogous tricyclic oxindoles such as ZZ. In a modification of the previous scheme, a one-pot dialkylation procedure may be used to provide the ester intermediate XX. Reduction of the nitro group via catalytic hydrogenation provides the aniline YY. This nitro reduction may also be effected using a wide range of conditions that are well known to those skilled in the art, including use of zinc, iron, or tin under acidic conditions or reduction with Raney nickel. Cyclization of YY, usually carried out by heating in xylenes in the presence of acid, affords the tricyclic oxindole ZZ, which may be elaborated to give compounds of the present invention in analogy with the foregoing schemes.

SCHEME 15

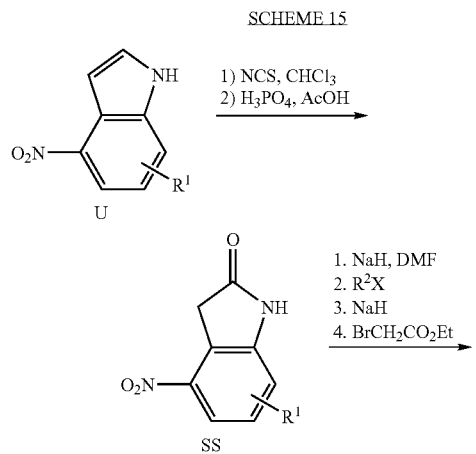

Simple modifications of these routes, including different protecting group strategies, application of well-precedented methodology, and the use of starting materials and reagents other than those described in the foregoing schemes, may be used to provide other acids of interest, such as those detailed in Intermediates 27-41 (vide infra).

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

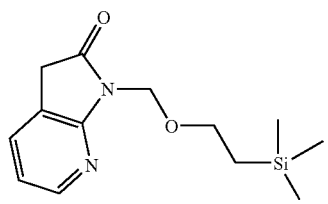

1-{[2-(Trimethylsilyl)ethoxy]methyl}-1,3-dihydro-2H-pyrrolo[2,3-b]pyridin-2-one

Step A. 1-{[2-Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with $H_2O$ (500 mL) and the mixture was extracted with $CH_2Cl_2$ (5×300 mL). The combined organic layers were washed with brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with $H_2O$ (300 mL) and extracted with EtOAc. The aqueous layer was washed with EtOAc (2×300 mL) and the combined organic layers were washed with $H_2O$ (4×300 mL; the final wash was pH 5-6), then brine (300 mL), then dried over $MgSO_4$, filtered and concentrated under reduced pressure. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×) and the combined organic layers were washed with $H_2O$, dried over $MgSO_4$, filtered, and concentrated. The crude product was filtered through a plug of silica gel eluting with $EtOAc:CH_2Cl_2$-1:9 and the eluant was concentrated under reduced pressure to provide the title compound. MS: m/z=265 (M+1).

INTERMEDIATE 2

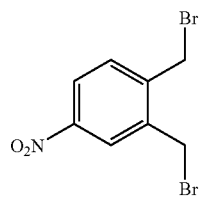

1,2-Bis(bromomethyl)-4-nitrobenzene

Step A. (4-Nitro-1,2-phenylene)dimethanol

4-Nitrophthalic acid (40 g, 189.5 mmol) in tetrahydrofuran (500 mL) was added dropwise over 1.5 h to a solution of borane-THF complex (1 M, 490 mL, 490 mmol), keeping the reaction temperature between 0° C. and 5° C. After the addition, the reaction was allowed to warm slowly to ambient temperature and stirred for 18 h. Methanol (100 mL) was added carefully and the precipitated solid dissolved. The mixture was concentrated in vacuo to about 500 mL, cooled to 0° C., and 10 N sodium hydroxide was added to adjust the pH to 10-11. This mixture was extracted with EtOAc (3×600 mL) and the combined organic layers were washed with brine, dried over $Na_2SO_4$, filtered, and concentrated to give the title compound. MS: m/z=207 (M–OH+$CH_3CN$).

Step B. 1,2-Bis(bromomethyl)-4-nitrobenzene

Phosphorus tribromide (3.9 mL, 41.1 mmol) in ether (50 mL) was added dropwise over 1.5 h to a solution of (4-nitro-1,2-phenylene)dimethanol from Step A (6.85 g, 37.4 mmol) in ether (150 mL). After 18 h, the reaction mixture was cooled to 0° C. and quenched with $H_2O$ (25 mL). The layers were separated and the organic layer was washed with $H_2O$, then saturated aqueous $NaHCO_3$, dried over $Na_2SO_4$, filtered, and concentrated to give the title compound. MS: m/z=309 (M).

INTERMEDIATE 3

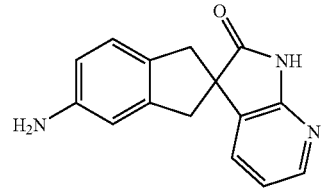

(–)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-nitrobenzene (40.9 g, 132 mmol, described in Intermediate 2) and 1-{[2-(trimethylsilyl)ethoxy]methyl}-1,3-dihydro-2H-pyrrolo[2,3-b]pyridin-2-one (31.5 g, 119 mmol, described in Intermediate 1) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and $H_2O$ (1 L). The organic layer was washed with $H_2O$ (1 L), then brine (500 mL), then dried over $Na_2SO_4$, filtered, and concentrated. The crude product was purified by silica gel chromatography, eluting with a gradient of hexane:EtOAc-100:0 to 0:100, to give the title compound. MS: m/z=412 (M+1).

Step B. (–)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated to give the crude racemic compound. The enantiomers were resolved by HPLC, utilizing a Chiralcel OD column and eluting with MeOH. The first major peak to elute was (−)-5-amino-1'-{[2-(trimethylsilyl)ethoxy]methyl}-1,3-dihydrospiro[indene-2,3'-pyrrolo[2,3-b]pyridin]-2'(1'H)-one, the title compound, and the second major peak to elute was (+)-5-amino-1'-{[2-(trimethylsilyl)ethoxy]methyl}-1,3-dihydrospiro[indene-2,3'-pyrrolo[2,3-b]pyridin]-2'(1'H)-one. MS: m/z=382 (M+1).

Step C. (−)-5-Amino-1,3-dihydrospiro[indene-2,3'-pyrrolo[2,3-b]pyridin]-2'(1'H)-one A solution of (−)-5-amino-1'-{[2-(trimethylsilyl)ethoxy]methyl}-1,3-dihydrospiro[indene-2,3'-pyrrolo[2,3-b]pyridin]-2'(1'H)-one from Step B (13.7 g, 35.9 mmol) in methanol (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (2.4 mL, 35.9 mmol) and 10 N sodium hydroxide (7.2 mL, 72 mmol) to adjust the mixture to pH 10. After 30 min, the mixture was diluted with $H_2O$ (400 mL) and extracted with $CHCl_3$ (2×1 L). The combined organic layers were dried over $Na_2SO_4$, filtered, and concentrated in vacuo. The crude material was triturated with MeOH (50 mL) to give the title compound. MS: m/z=252 (M+1).

INTERMEDIATE 4

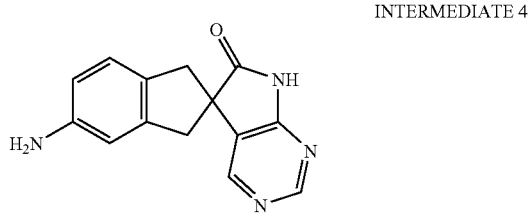

(±)-5-Amino-1,3-dihydrospiro[indene-2,5'-pyrrolo[2,3-d]pyrimidin]-6'(7'H)-one

Step A. 5,5-Dibromo-4-chloro-5,7-dihydro-6H-pyrrolo[2,3-d]pyrimidin-6-one

Pyridine hydrobromide perbromide (15.6 g, 48.8 mmol) was added in three portions to a stirred solution of 6-chloro-7-deazapurine (2.5 g, 16.3 mmol) at 40° C. in tert-butanol (100 mL). After 3 h, an additional amount of pyridine hydrobromide perbromide (5.19 g, 16.3 mmol) was added. After a further 2 h, the reaction mixture was concentrated in vacuo and partitioned between EtOAc and $H_2O$. The aqueous solution was extracted with EtOAc (2×) and the combined organic layers were washed with $H_2O$, dried over $Na_2SO_4$, filtered, and concentrated in vacuo to give the title compound. MS: m/z=328 (M+1).

Step B. 4-Chloro-5,7-dihydro-6H-pyrrolo[2,3-d]pyrimidin-6-one

Zinc (6.05 g, 92.56 mmol) was added to a solution of 5,5-dibromo-4-chloro-5,7-dihydro-6H-pyrrolo[2,3-d]pyrimidin-6-one from Step A (3.03 g, 9.26 mmol) in THF (20 mL) and saturated aqueous ammonium chloride (5 mL). After 3 h, the reaction mixture was concentrated in vacuo and purified by HPLC using a reversed phase C18 column and eluting with a gradient of $H_2O$:$CH_3CN$:$CF_3CO_2H$-90:10:0.1 to 5:95:0.1. Lyophilization provided the title compound. MS: m/z=170 (M+1).

Step C. (±)-4'-Chloro-5-nitro-1,3-dihydrospiro[indene-2,5'-pyrrolo[2,3-d]pyrimidin]-6'(7'H)-one Butyllithium (0.29 ml, 0.74 mmol, 2.5 M) was added to a stirred solution of 4-chloro-5,7-dihydro-6H-pyrrolo[2,3-d]pyrimidin-6-one from Step B (50 mg, 0.295 mmol) at −78° C. in THF (30 mL). After complete addition of butyllithium, N,N,N',N'-tetramethylethane-1,2-diamine (0.31 mL, 0.77 mmol) was added. After 1 h at −78° C., 1,2-bis(bromomethyl)-4-nitrobenzene (91 mg, 0.295 mmol, described in Intermediate 2) was added and the reaction warmed to ambient temperature. After 8 h, the reaction was quenched with $H_2O$ and the mixture was partitioned between EtOAc and $H_2O$. The aqueous solution was extracted with EtOAc (3×20 mL). The combined organic extracts were washed with brine (100 mL), dried over $Na_2SO_4$, filtered, and concentrated in vacuo to give the title compound. MS: m/z=317 (M+1).

Step D. (±)-5-Amino-1,3-dihydrospiro[indene-2,5'-pyrrolo[2,3-d]pyrimidin]-6'(7'H)-one To a solution of (±)-4'-chloro-5-nitro-1,3-dihydrospiro[indene-2,5'-pyrrolo[2,3-d]pyrimidin]-6'(7'H)-one from Step C (400 mg, 1.26 mmol) in EtOAc (40 mL) and MeOH (10 mL) was added triethylamine (0.88 mL, 6.315 mmol). The mixture was hydrogenated at 50 psi hydrogen over 10% Pd/C (100 mg). After 24 h and 90 h, an additional amount of palladium on carbon (100 mg) was added to the reaction mixture and hydrogenation was continued for a total of 180 h. The reaction mixture was filtered through a pad of Celite and concentrated in vacuo. The residue was purified by HPLC using a reversed phase C18 column and eluting with a gradient of $H_2O$:$CH_3CN$:$CF_3CO_2H$—90:10:0.1 to 5:95:0.1. Lyophilization provided the title compound. MS: m/z=253 (M+1).

INTERMEDIATE 5

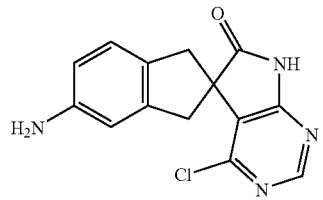

(±)-5-Amino-4'-chloro-1,3-dihydrospiro[indene-2,5'-pyrrolo[2,3-d]pyrimidin]-6'(7'H)-one To a solution of (±)-4'-chloro-5-nitro-1,3-dihydrospiro[indene-2,5'-pyrrolo[2,3-d]pyrimidin]-6'(7'H)-one (40 mg, 0.126 mmol, described in Intermediate 4) in EtOAc (10 mL) was added triethylamine (0.026 mL, 0.189 mmol). The mixture was hydrogenated at 30 psi hydrogen over 10% Pd/C (10 mg). After 2 h, the reaction mixture was filtered through a pad of Celite and concentrated in vacuo. The residue was purified by HPLC using a reversed phase C18 column and eluting with a gradient of $H_2O$:$CH_3CN$:$CF_3CO_2H$—90:10:0.1 to 5:95:0.1. Lyophilization provided the title compound. MS: m/z=287 (M+1).

INTERMEDIATE 6

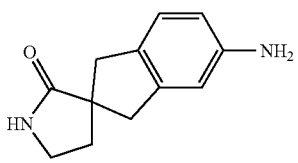

(±)-5-Amino-1,3-dihydro-2'H-spiro[indene-2,3'-pyrrolidin]-2'-one

Step A. Ethyl 2-allylindane-2-carboxylate

To a solution of ethyl indane-2-carboxylate [Schaaf et al., J. Med. Chem. 1983, 26, 328-334] (6.87 g, 36.1 mmol) in THF (100 mL) at −78° C. was added sodium bis(trimethylsilyl)amide (1.0 M in THF, 39.7 mL, 39.7 mmol) dropwise over 20 min. The resulting yellow solution was stirred for 1 h, and then allyl bromide (3.75 mL, 43.3 mmol) was added over 5 min. Stirring was continued for 1.5 h at −78° C., and then the reaction was quenched by the addition of saturated $NH_4Cl$ and warmed to ambient temperature. The reaction mixture was partitioned between saturated $NH_4Cl$ (100 mL) and EtOAc (100 mL). The aqueous phase was further extracted with EtOAc (2×50 mL), and the combined organic layers were dried over $Na_2SO_4$, filtered, and concentrated under reduced pressure. The crude product was purified by silica gel chromatography, eluting with a gradient of hexane:EtOAc—100:0 to 75:25, to give the title compound. MS: m/z=231 (M+1).

Step B. Ethyl 2-(2-oxoethyl)indane-2-carboxylate

Ethyl 2-allylindane-2-carboxylate from Step A (3.00 g, 13.0 mmol) was dissolved in $CH_2Cl_2$ (100 mL) and cooled to −78° C. Ozone was bubbled through the solution for 15 min, at which time a light blue color persisted. Triethylamine (3.63 mL, 26.1 mmol) was added and the reaction mixture was stirred at ambient temperature for 1.5 h. The reaction mixture was partitioned between saturated $NaHCO_3$ (100 mL) and $CH_2Cl_2$ (100 mL). The aqueous phase was further extracted with $CH_2Cl_2$ (2×50 mL), and the combined organic layers were dried over $Na_2SO_4$, filtered, and concentrated under reduced pressure to give the title compound. MS: m/z=233 (M+1).

Step C. 1,3-Dihydro-2'H-spiro[indene-2,3'-pyrrolidin]-2'-one

Ethyl 2-(2-oxoethyl)indane-2-carboxylate from Step B (3.03 g, 13.0 mmol) and ammonium acetate (50.2 g, 651 mmol) were stirred in AcOH (20 mL) and MeOH (20 mL) at ambient temperature for 4 h, then sodium cyanoborohydride (1.29 g, 19.5 mmol) was added and stirring continued for 16 h. The reaction mixture was concentrated in vacuo and partitioned between saturated $NaHCO_3$ (50 mL) and $CH_2Cl_2$ (50 mL). The aqueous phase was further extracted with $CH_2Cl_2$ (2×25 mL), and the combined organic layers were dried over $Na_2SO_4$, filtered, and concentrated under reduced pressure to yield a yellow oil. The crude oil was heated to reflux in toluene (100 mL) for 1.5 h and then concentrated in vacuo. The crude product was purified by silica gel chromatography, eluting with a gradient of $CH_2Cl_2$:MeOH—100:0 to 90:10, to give the title compound. MS: m/z=188 (M+1).

Step D. (±)-5-Nitro-1,3-dihydro-2'H-spiro[indene-2,3'-pyrrolidin]-2'-one

To 1,3-dihydro-2'H-spiro[indene-2,3'-pyrrolidin]-2'-one from Step C (114 mg, 0.609 mmol), cooled in an ice bath, was added 70% $HNO_3$ (5 mL). The reaction mixture was stirred for 45 min, diluted with $H_2O$ (10 mL), and extracted with $CH_2Cl_2$ (3×10 mL). The combined organic layers were dried over $Na_2SO_4$, filtered, and concentrated under reduced pressure. The crude product was purified by silica gel chromatography, eluting with a gradient of $CH_2Cl_2$:EtOAc—100:0 to 50:50, to give the title compound. MS: m/z=233 (M+1).

Step E. (±)-5-Amino-1,3-dihydro-2'H-spiro[indene-2,3'-pyrrolidin]-2'-one

To a solution of (±)-5-nitro-1,3-dihydro-2'H-spiro[indene-2,3'-pyrrolidin]-2'-one from Step D (97.0 mg, 0.418 mmol) in MeOH (5 mL) was added 10% Pd/C (15 mg). The reaction mixture was stirred under a hydrogen atmosphere (ca. 1 atm) for 1.5 h, then filtered through a Celite pad and concentrated under reduced pressure to give the title compound. MS: m/z=203 (M+1).

INTERMEDIATE 7

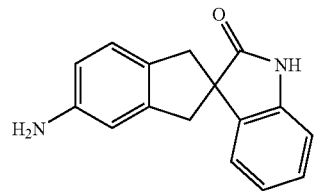

(±)-5-Amino-1,3-dihydrospiro[indene-2,3'-indol]-2'(1'H)-one

Step A. (±)-5-Bromo-1,3-dihydrospiro[indene-2,3'-indol]-2'(1'H)-one

To a solution of oxindole (363 mg, 2.73 mmol) at −78° C. in THF (15 mL) was added butyllithium (2.5 M in hexanes, 2.29 mL, 5.73 mmol) dropwise, followed by the dropwise addition of tetramethylethylenediamine (0.905 mL, 6.00 mmol). The solution was stirred for 1 h at −78° C., then a solution of 4-bromo-1,2-bis(bromomethyl)benzene [Anderson et al., J. Org. Chem. 1979, 44(9), 1519-1533] (1.87 g, 5.45 mmol) in THF (5 mL) was added dropwise. The reaction solution was stirred at −10 to −20° C. for 2 h and at ambient temperature for 16 h. The reaction mixture was partitioned between saturated $NH_4Cl$ (50 mL) and EtOAc (50 mL). The aqueous phase was further extracted with EtOAc (2×50 mL), and the combined organic layers were dried over $Na_2SO_4$, filtered, and concentrated under reduced pressure. The crude product was purified by silica gel chromatography, eluting with a gradient of hexane:EtOAc—100:0 to 50:50, to give the title compound. MS: m/z=315 (M+1).

Step B. (±)-2'-Oxo-1,1',2',3-tetrahydrospiro[indene-2,3'-indole]-5-carboxylic acid To a solution of (±)-5-bromo-1,3-dihydrospiro[indene-2,3'-indol]-2'(1'H)-one from Step A (220 mg, 0.700 mmol) in THF (2 mL) was added ethylmagnesium bromide (3.0 M in ether, 0.467 mL, 1.40 mmol) dropwise, maintaining the reaction temperature <−60° C. Then tert-butyllithium (1.7 M in pentane, 1.65 mL, 2.80 mmol) was added dropwise, maintaining the reaction temperature <−60° C. The reaction solution was stirred for 5 min at −78° C., then CO$_2$(g) was bubbled through the solution for 15 min. Added H$_2$O (5 mL) and warmed to ambient temperature. The reaction mixture was partitioned between EtOAc (20 mL) and saturated NaHCO$_3$ (20 mL). The organic layer was further extracted with saturated NaHCO$_3$ (2×10 mL). The combined aqueous layers were washed with EtOAc (10 mL) and then acidified with 12 M HCl. The combined aqueous layers were extracted with CH$_2$Cl$_2$ (5×10 mL). A white precipitate formed that was insoluble in either layer, and was collected by filtration. The combined CH$_2$Cl$_2$ layers were dried over Na$_2$SO$_4$, filtered, and concentrated under reduced pressure. This crude product was combined with the recovered precipitate to give the title compound. MS: m/z=280 (M+1).

Step C. (±)-tert-Butyl (2'-oxo-1,1',2',3-tetrahydrospiro[indene-2,3'-indol]-5-yl)carbamate A solution of (±)-2'-oxo-1,1',2',3-tetrahydrospiro[indene-2,3'-indole]-5-carboxylic acid from Step B (65.0 mg, 0.233 mmol), diphenylphosphoryl azide (0.060 mL, 0.279 mmol), and triethylamine (0.039 mL, 0.279 mmol) in t-BuOH (5 mL) was heated to reflux for 3 h. The reaction mixture was concentrated in vacuo. The crude product was purified by silica gel chromatography, eluting with a gradient of hexane:EtOAc—100:0 to 50:50, to give the title compound. MS: m/z=295 (M−C$_4$H$_7$).

Step D. (±)-5-Amino-1,3-dihydrospiro[indene-2,3'-indol]-2'(1'H)-one

HCl (g) was bubbled through a solution of (±)-tert-butyl (2'-oxo-1,1',2',3-tetrahydrospiro[indene-2,3'-indol]-5-yl)carbamate from Step C (19.0 mg, 0.054 mmol) in EtOAc (5 mL) for 15 min. The reaction mixture was stirred at ambient temperature for 1 h and then concentrated in vacuo to give the title compound as the hydrochloride salt. MS: m/z=251 (M+1).

INTERMEDIATE 8

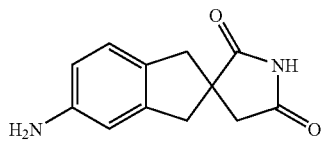

(±)-5-Amino-1,3-dihydro-2'H,5'H-spiro[indene-2,3'-pyrrolidine]-2',5'-dione

Step A. Ethyl 2-(2-tert-butoxy-2-oxoethyl)indane-2-carboxylate

To a solution of ethyl indane-2-carboxylate (Schaaf et al., J. Med. Chem. 1983, 26, 328-334) (2.00 g, 10.5 mmol) in THF at −78° C. was added sodium bis(trimethylsilyl)amide (15.8 mL of a 1.0 M solution in THF, 15.8 mmol) dropwise, over 10 min. The mixture was stirred for 15 min, then tert-butyl bromoacetate (3.08 g, 15.8 mmol) was added dropwise, over 30 min. The resulting mixture was stirred for 30 min at −78° C., then poured into brine (20 mL) and extracted with EtOAc (50 mL). The organic layer was dried over Na$_2$SO$_4$, filtered, and concentrated in vacuo. The crude product was purified by silica gel chromatography, eluting with a gradient of hexane:EtOAc—100:0 to 90:10, to give the title compound. MS: m/z=368 (M+Na+CH$_3$CN).

Step B. 2-(2-tert-Butoxy-2-oxoethyl)indane-2-carboxylic acid

A mixture of ethyl 2-(2-tert-butoxy-2-oxoethyl)indane-2-carboxylate from Step A (2.48 g, 8.15 mmol) and 1.0 N sodium hydroxide (8.96 mL, 8.96 mmol) in THF (50 mL), H$_2$O (10 mL), and EtOH (20 mL) was stirred at ambient temperature for 18 h. The mixture was acidified with hydrochloric acid to about pH 3 and extracted with EtOAc (3×50 mL). The combined organic layers were dried over Na$_2$SO$_4$, filtered, and concentrated in vacuo, to give the title compound. MS: m/z=340 (M+Na+CH$_3$CN).

Step C. 2-(Carboxymethyl)indane-2-carboxylic acid

A solution of 2-(2-tert-butoxy-2-oxoethyl)indane-2-carboxylic acid from Step B (1.50 g, 5.43 mmol) in EtOAc (100 mL) was saturated with HCl (g) and stood at ambient temperature for 1 h, then concentrated to dryness in vacuo, to give the title compound. MS: m/z=284 (M+Na+CH$_3$CN).

Step D. 1,3-Dihydro-2'H,5'H-spiro[indene-2,3'-pyrrolidine]-2',5'-dione

A solution of 2-(carboxymethyl)indane-2-carboxylic acid from Step C (1.10 g, 4.99 mmol) in acetyl chloride (18 mL) was heated at reflux for 18 h, then concentrated in vacuo. The residue was recrystallized from toluene to give 1',3'-dihydrospiro[furan-3,2'-indene]-2,5(4H)-dione as an ivory solid. This solid was dissolved in CH$_2$Cl$_2$ (25 mL) and NH$_3$ (g) was bubbled into the mixture for 20 min. After a further 30 min, the solvent was evaporated under reduced pressure. The resulting solid was dried under high vacuum for 1 h, then resuspended in acetyl chloride (20 mL) and heated to reflux for 18 h. The solvent was removed in vacuo and the crude solid was recrystallized from EtOH:Et$_2$O to afford the title compound. MS: m/z=202 (M+1).

Step E. (±)-5-Amino-1,3-dihydro-2'H,5'H-spiro[indene-2,3'-pyrrolidine]-2',5'-dione To a solution of 1,3-dihydro-2'H,5'H-spiro[indene-2,3'-pyrrolidine]-2',5'-dione from Step D (400 mg, 1.99 mmol) in CF$_3$CO$_2$H (10 mL) was added sodium nitrite (411 mg, 5.96 mmol) and the mixture was heated to 55° C. for 2 h. The mixture was cooled and diluted with H$_2$O (10 mL), then extracted with EtOAc (2×30 mL). The combined organic layers were dried over Na$_2$SO$_4$, filtered, and concentrated in vacuo, to give (±)-5-nitro-1,3-dihydro-2'H,5'H-spiro[indene-2,3'-pyrrolidine]-2',5'-dione, which contained some of the isomeric (±)-4-nitro-1,3-dihydro-2'H,5'H-spiro[indene-2,3'-pyrrolidine]-2',5'-dione. This solid was dissolved in EtOH (30 mL), then AcOH (0.55 mL) and 10% Pd/C (55 mg) were added. The mixture was stirred vigorously under an atmosphere of hydrogen (ca. 1 atm) for 2 h, then filtered through a pad of Celite, and concentrated in vacuo. The crude product was purified by silica gel chromatography, eluting with a gradient of CH$_2$Cl$_2$:EtOAc—95:5 to 10:90, to give the title compound. MS: m/z=217 (M+1).

INTERMEDIATE 9

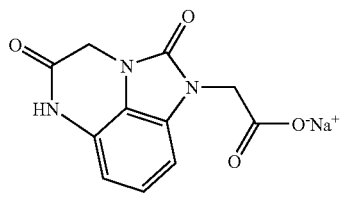

Sodium (2,5-dioxo-5,6-dihydro-4H-imidazo[1,5,4-de]quinoxalin-1(2H)-yl)acetate

Step A. 4-Nitro-1,3-dihydro-2H-benzimidazol-2-one

Triphosgene (56 g, 188.8 mol) was added portionwise over 15 min to a solution of 3-nitro-1,2-phenylenediamine (25.5 g, 167 mol) in CH₃CN (400 mL) at 0° C. and the mixture was allowed to warm to ambient temperature after 30 min. The reaction was concentrated in vacuo, diluted with toluene (100 mL) and the solid precipitate was collected by filtration to give the title compound. MS: m/z=180 (M+1).

Step B. Dimethyl 2,2'-(4-nitro-2-oxo-1H-benzimidazole-1,3-diyl)diacetate

Cesium carbonate (3.6 g, 11.1 mmol) was added to a solution of 4-nitro-1,3-dihydro-2H-benzimidazol-2-one from Step A (990 mg, 5.5 mmol) and methyl bromoacetate (1.05 mL, 11.1 mmol) in DMF (25 mL). After 1.5 h, then reaction was quenched with H₂O and the solid precipitate was collected by filtration to give the title compound. MS: m/z=324 (M+1).

Step C. Methyl (2,5-dioxo-5,6-dihydro-4H-imidazo[1,5,4-de]quinoxalin-1(2H)-yl)acetate A mixture of dimethyl 2,2'-(4-nitro-2-oxo-1H-benzimidazole-1,3-diyl)diacetate from Step B (270 mg, 0.84 mmol) and 10% Pd/C (50 mg) in MeOH (10 mL) was stirred under an atmosphere of hydrogen (ca. 1 atm). After 2 h, the reaction was filtered through a Celite pad and concentrated in vacuo. The crude solid was dissolved in toluene (3 mL) and p-toluenesulfonic acid monohydrate (2 mg, 0.011 mmol) was added. The mixture was heated at reflux for 30 min and then concentrated in vacuo to give the title compound. MS: m/z=262 (M+1).

Step D. Sodium (2,5-dioxo-5,6-dihydro-4H-imidazo[1,5,4-de]quinoxalin-1(2-yl)acetate To a solution of methyl (2,5-dioxo-5,6-dihydro-4H-imidazo[1,5,4-de]quinoxalin-1(2H)-yl)acetate from Step C (367 mg, 1.40 mmol) in MeOH (40 mL) and CH₃CN (5 mL) was added 1.0 N sodium hydroxide (2.82 mL, 2.82 mmol) and the reaction mixture was stirred at room temperature for 18 h. The mixture was neutralized with 1 N aqueous HCl and concentrated in vacuo to give the title compound. MS: m/z=248 (M+1).

INTERMEDIATE 10

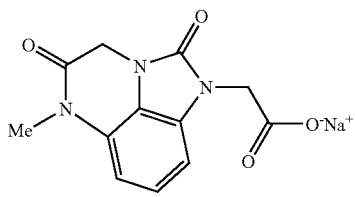

Sodium (6-methyl-2,5-dioxo-5,6-dihydro-4H-imidazo[1,5,4-de]quinoxalin-1(2H)-yl)acetate

Step A. Methyl (6-methyl-2,5-dioxo-5,6-dihydro-4H-imidazo[1,5,4-de]quinoxalin-1(2H)-yl)acetate To a solution of methyl (2,5-dioxo-5,6-dihydro-4H-imidazo[1,5,4-de]quinoxalin-1(2H)-yl)acetate (300 mg, 1.15 mmol, described in Intermediate 9) in DMF (5 mL) were added cesium carbonate (748 mg, 2.3 mmol) and iodomethane (326 mg, 2.3 mmol). After 16 h, the reaction mixture was quenched with brine (20 mL) and extracted with EtOAc (50 mL). The organic layer was dried over Na₂SO₄, filtered, and concentrated in vacuo to give the title compound. MS: m/z=276 (M+1).

Step B. Sodium (6-methyl-2,5-dioxo-5,6-dihydro-4H-imidazo[1,5,4-de]quinoxalin-1(2H)-yl)acetate To a solution of methyl (6-methyl-2,5-dioxo-5,6-dihydro-4H-imidazo[1,5,4-de]quinoxalin-1(2H)-yl)acetate from Step A (225 mg, 0.817 mol) in MeOH (10 mL) was added 1.0 N sodium hydroxide (1.2 mL, 1.2 mmol). After 3 h, the reaction mixture was neutralized with 1 N aqueous HCl and concentrated to give the title compound. MS: m/z=262 (M+1).

INTERMEDIATE 11

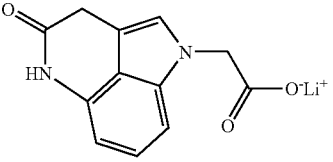

Lithium (4-oxo-4,5-dihydropyrrolo[4,3,2-de]quinolin-1(3H)-yl)acetate

Step A. N,N-Dimethyl-1-(4-nitro-1H-indol-3-yl)methanamine

N,N,N',N'-Tetramethyldiaminomethane (2.2 mL, 15.6 mol) in acetic acid (30 mL) was added dropwise over 60 min to a solution of 4-nitroindole (2.30 g, 14.2 mol) in acetic acid (30 mL). After 3.5 h, the reaction was cooled to 0° C., and 20% aqueous sodium hydroxide was added to adjust the pH to 11. The mixture was extracted with CHCl₃ (3×300 mL) and the combined organic extracts were dried over Na₂SO₄, filtered, and concentrated in vacuo to give the title compound. MS: m/z=220 (M+1).

Step B. (4-Nitro-1H-indol-3-yl)acetonitrile

Potassium cyanide (9.20 g, 141 mmol) in H₂O (80 mL) was added to a solution of N,N-dimethyl-1-(4-nitro-1H-indol-3- yl)methanamine from Step A (3.10 g, 14.1 mmol) in DMF (80 mL) and the mixture was heated at reflux for 1 h, then cooled to ambient temperature and partitioned between H$_2$O (200 mL) and EtOAc (400 mL). The organic layer was dried over Na$_2$SO$_4$, filtered, and concentrated in vacuo. The crude product was purified by silica gel chromatography, eluting with a gradient of hexane:EtOAc—100:0 to 0:100, to give the title compound. MS: m/z=265 (M+Na+CH$_3$CN).

Step C. tert-Butyl [3-(cyanomethyl)-4-nitro-1H-indol-1-yl]acetate

Sodium hydride (198 mg of a 60% dispersion in mineral oil, 5.0 mmol) was added to a solution of (4-nitro-1H-indol-3-yl)acetonitrile from Step B (910 mg, 4.52 mmol) in DMF (15 mL). After 10 min, tert-butyl bromoacetate (0.801 mL, 5.4 mmol) was added dropwise and the reaction mixture was stirred at ambient temperature for 1.5 h. The mixture was partitioned between H$_2$O (50 mL) and EtOAc (100 mL) and the organic extract was washed with brine, dried over Na$_2$SO$_4$, filtered, and concentrated in vacuo. The crude product was purified by silica gel chromatography, eluting with a gradient of hexane:EtOAc—100:0 to 0:100, to give the title compound. MS: m/z=316 (M+1).

Step D. 2,2'-(4-Nitro-1H-indole-1,3-diyl)diacetic acid

To a solution of tert-butyl [3-(cyanomethyl)-4-nitro-1H-indol-1-yl]acetate from Step C (920 mg, 2.92 mol) in ethanol (50 mL) was added 1.0 N aqueous sodium hydroxide (14.6 mL, 14.6 mmol) and the mixture was heated at reflux for 18 h. An additional amount of 1.0 N sodium hydroxide (15 mL, 15 mmol) was added to the reaction, most of the EtOH was distilled out of the flask, and the mixture was heated at reflux for a further 21 h. The reaction mixture was cooled to 0° C. and concentrated HCl was added to adjust the pH to 1-2. The mixture was extracted with EtOAc (2×150 mL) and the combined organic extracts were dried over Na$_2$SO$_4$, filtered, and concentrated in vacuo to give the title compound. MS: m/z=279 (M+1).

Step E. Diethyl 2,2'-(4-nitro-1H-indole-1,3-diyl)diacetate

Concentrated sulfuric acid (0.02 mL) was added to a solution of 2,2'-(4-nitro-1H-indole-1,3-diyl)diacetic acid from Step D (742 mg, 2.67 mol) in EtOH (100 mL) and the mixture was heated at reflux for 9 h. The reaction mixture was allowed to cool to ambient temperature and was concentrated to a volume of 30 mL in vacuo. The solution was partitioned between EtOAc (300 mL) and aqueous NaHCO$_3$ (100 mL) and the organic layer was dried over Na$_2$SO$_4$, filtered, and concentrated in vacuo to give the title compound. MS: m/z=335 (M+1).

Step F. Diethyl 2,2'-(4-amino-1H-indole-1,3-diyl)diacetate

A mixture of diethyl 2,2'-(4-nitro-1H-indole-1,3-diyl)diacetate from Step E (140 mg, 0.419 mmol) and 10% Pd/C (20 mg) in EtOH (20 mL) was stirred under an atmosphere of hydrogen (ca. 1 atm). After 1.5 h, the reaction mixture was filtered through a Celite pad and concentrated in vacuo to give the title compound. MS: m/z=305 (M+1).

Step G. Ethyl (4-oxo-4,5-dihydropyrrolo[4,3,2-de]quinolin-1(3H)-yl)acetate

To a solution of diethyl 2,2'-(4-amino-1H-indole-1,3-diyl) diacetate from Step F (83 mg, 0.273 mmol) in toluene (8 mL) was added p-toluenesulfonic acid monohydrate (5 mg, 0.026 mmol) and the mixture was heated at reflux. After 2 h, the reaction was allowed to cool to ambient temperature and the mixture was partitioned between EtOAc (40 mL) and aqueous NaHCO$_3$ (15 mL). The organic layer was washed with brine, dried over Na$_2$SO$_4$, filtered, and concentrated in vacuo. The crude product was purified by silica gel chromatography, eluting with a gradient of CH$_2$Cl$_2$:MeOH—100:0 to 92:8, to give the title compound. MS: m/z=259 (M+1).

Step H. Lithium (4-oxo-4,5-dihydropyrrolo[4,3,2-de]quinolin-1(3H)-yl)acetate

To a solution of ethyl (4-oxo-4,5-dihydropyrrolo[4,3,2-de]quinolin-1(3H)-yl)acetate from Step G (79 mg, 0.306 mmol) in ethanol (3 mL) and water (0.5 mL) was added dropwise 1.0 N aqueous lithium hydroxide (0.34 mL, 0.34 mmol). After 5 min, 1 N aqueous HCl was added to adjust the mixture to pH 7 and the solution was concentrated in vacuo to give the title compound. MS: m/z=231 (M+1).

INTERMEDIATE 12

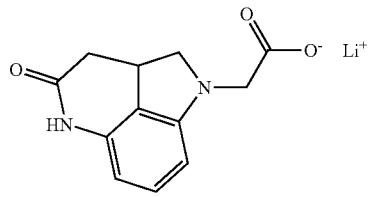

Lithium (4-oxo-2a,3,4,5-tetrahydropyrrolo[4,3,2-de]quinolin-1(2H)-yl)acetate, enantiomer B Step A. Methyl (4-nitro-1H-indol-3-yl)(oxo)acetate Diphosphoryl chloride (0.938 mL, 6.80 mmol) was added dropwise to a solution of 4-nitroindole (1.00 g, 6.17 mmol) and methylpyrrolidinyl glyoxylate (Downie et al., *Tetrahedron*, 1993, 49, 4015-4034) (1.10 g, 6.80 mmol) at 0° C. and the mixture was allowed to warm to ambient temperature over 3 h. MeOH, then saturated aqueous NaHCO$_3$ were added to the reaction at 0° C. and the solution was extracted with CH$_2$Cl$_2$ (3×50 mL). The combined organic extracts were dried over Na$_2$SO$_4$, filtered, and concentrated in vacuo until crystals formed. The crystals were collected by vacuum filtration and two more crops were isolated from the filtrate to give the title compound. MS: m/z=249 (M+1).

Step B. (±)-Methyl (4-nitro-2,3-dihydro-1H-indol-3-yl)acetate

Triethylsilane (13 mL, 80.6 mmol) was added to a solution of methyl (4-nitro-1H-indol-3-yl)(oxo)acetate from Step A (1.00 g, 4.03 mmol) in TFA (15 mL). After 3 h, the reaction mixture was concentrated in vacuo and the residue was purified by silica gel chromatography, eluting with a gradient of CHCl$_3$:MeOH—100:0 to 98:2, to give the title compound. MS: m/z=237 (M+1).

Step C. (±)-Ethyl methyl 2,2'-(4-nitro-2,3-dihydro-1H-indole-1,3-diyl)diacetate To a solution of (±)-methyl (4-nitro-2,3-dihydro-1H-indol-3-yl)acetate from Step B (700 mg, 2.97 mmol), sodium carbonate (471 mg, 4.44 mmol), and potassium iodide (98 mg, 0.59 mmol) in acetone (15 mL) was added ethyl bromoacetate (9.9 mL, 88.9 mmol). The mixture was heated at reflux for 18 h, then cooled to ambient temperature and concentrated in vacuo. The residue was partitioned between H$_2$O (15 mL) and EtOAc (2×40 mL) and the organic extracts were washed with brine, dried over Na$_2$SO$_4$, filtered, and concentrated in vacuo to a volume of 50 mL. Hexane was added to the EtOAc solution and a precipitate formed. The desired crystals were collected by vacuum filtration to give the title compound. MS: m/z=323 (M+1).

Step D. (±)-Ethyl methyl 2,2'-(4-amino-2,3-dihydro-1H-indole-1,3-diyl)diacetate A mixture of (±)-ethyl methyl 2,2'-(4-nitro-2,3-dihydro-1H-indole-1,3-diyl)diacetate from Step C (550 mg, 1.71 mmol) and 10% Pd/C (40 mg) in EtOH (10 mL) was stirred under an atmosphere of hydrogen (ca. 1 atm). After 3 h, the reaction was filtered through a Celite pad and concentrated in vacuo to give the title compound. MS: m/z=293 (M+1).

Step E. Ethyl (4-oxo-2a3,4,5-tetrahydropyrrolo[4,3,2-de]quinolin-1(2H)-yl)acetate, enantiomer B To a solution of (±)-ethyl methyl 2,2'-(4-amino-2,3-dihydro-1H-indole-1,3-diyl)diacetate from Step D (490 mg, 1.70 mmol) in toluene (35 mL) was added p-toluenesulfonic acid monohydrate (5 mg, 0.026 mmol) and the mixture was heated at reflux for 48 h. The mixture was cooled to ambient temperature and was partitioned between saturated aqueous NaHCO$_3$ (5 mL) and EtOAc (40 mL). The organic layer was dried over Na$_2$SO$_4$, filtered, and concentrated in vacuo. The crude product was purified by silica gel chromatography, eluting with a gradient of CHCl$_3$:EtOAc—90:10 to 40:60, to give the racemic product. The enantiomers were resolved by HPLC, utilizing a Chiralpak AS column and eluting with MeOH. The first major peak to elute was ethyl (4-oxo-2a,3,4,5-tetrahydropyrrolo[4,3,2-de]quinolin-1(2H)-yl)acetate, enantiomer A, and the second major peak to elute was ethyl (4-oxo-2a,3,4,5-tetrahydropyrrolo[4,3,2-de]quinolin-1(2H)-yl)acetate, enantiomer B, the title compound. MS: m/z=261 (M+1).

Step F. Lithium (4-oxo-2a,3,4,5-tetrahydropyrrolo[4,3,2-de]quinolin-1(2H)-yl)acetate, enantiomer B To a solution of ethyl (4-oxo-2a,3,4,5-tetrahydropyrrolo[4,3,2-de]quinolin-1(2H)-yl)acetate, enantiomer B, from Step E (55 mg, 0.211 mmol) in THF (1 mL), EtOH (1 mL) and H$_2$O (1 mL) was added 1.0 N lithium hydroxide (0.232 mL, 0.232 mmol). After 15 min, 1 N aqueous HCl was added to adjust the solution to pH 7 and the mixture was concentrated in vacuo to give the title compound. MS: m/z=233 (M+1).

INTERMEDIATE 13

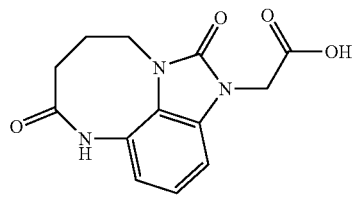

(2,7-Dioxo-5,6,7,8-tetrahydro-4H-imidazo[1,5,4-fg][1,6]-benzodiazocin-1(2H)-yl)acetic acid

Step A. tert-Butyl (4-nitro-2-oxo-2,3-dihydro-1H-benzimidazol-1-yl)acetate

Cesium carbonate (1.75 g, 5.4 mmol) was added to a solution of 4-nitro-1,3-dihydro-2H-benzimidazol-2-one (800 mg, 4.5 mmol, described in Intermediate 9) and tert-butyl bromoacetate (0.791 mL, 5.4 mmol) in DMF (15 mL). After 18 h, the reaction was quenched with H$_2$O (100 mL) and the solid precipitate was collected by filtration. The crude product was purified by silica gel chromatography, eluting with CH$_2$Cl$_2$:MeOH—95:5, to give the title compound. MS: m/z=294 (M+1).

Step B. Methyl 4-[3-(2-tert-butoxy-2-oxoethyl)-7-nitro-2-oxo-2,3-dihydro-1H-benzimidazol-1-yl]butanoate Sodium hydride (26.7 mg of a 60% dispersion in mineral oil, 0.66 mmol) was added to a solution of tert-butyl (4-nitro-2-oxo-2,3-dihydro-1H-benzimidazol-1-yl)acetate from Step A (96 mg, 0.327 mmol) in DMF (5 mL). After 10 min, methyl 4-bromobutyrate (178 mg, 0.98 mmol) was added and the reaction was stirred at room temperature for 18 h. The mixture was quenched with H$_2$O and extracted with EtOAc. The organic extract was washed with brine, dried over Na$_2$SO$_4$, filtered, and concentrated in vacuo. The residue was purified by HPLC using a reversed phase C18 column and eluting with a gradient of H$_2$O:CH$_3$CN:CF$_3$CO$_2$H—90:10:0.1 to 5:95:0.1. Lyophilization provided the title compound. MS: m/z=394 (M+1).

Step C. Methyl 4-[7-amino-3-(2-tert-butoxy-2-oxoethyl)-2-oxo-2,3-dihydro-1H-benzimidazol-1-yl]butanoate A mixture of methyl 4-[3-(2-tert-butoxy-2-oxoethyl)-7-nitro-2-oxo-2,3-dihydro-1H-benzimidazol-1-yl]butanoate from Step B (129 mg, 0.33 mmol) and 10% Pd/C (40 mg) in EtOH (30 mL) and EtOAc (15 mL) was stirred under an atmosphere of hydrogen (ca. 1 atm). After 1 h, the reaction was filtered through a Celite pad and concentrated in vacuo to give the title compound. MS: m/z=364 (M+1).

Step D. tert-Butyl (2,7-dioxo-5,6,7,8-tetrahydro-4H-imidazo[1,5,4-fg][1,6]benzodiazocin-1(2H)-yl)acetate To a solution of methyl 4-[7-amino-3-(2-tert-butoxy-2-oxoethyl)-2-oxo-2,3-dihydro-1H-benzimidazol-1-yl]butanoate from Step C (119 mg, 0.327 mmol) in toluene (5 mL) was added p-toluenesulfonic acid monohydrate (2 mg, 0.011 mmol) and the mixture was heated at reflux. After 3 h, the reaction mixture was allowed to cool to ambient temperature and the mixture was concentrated in vacuo to give the title compound. MS: m/z=332 (M+1).

Step E. (2,7-Dioxo-5,6,7,8-tetrahydro-4H-imidazo[1,5,4-fg][1,6]benzodiazocin-1(2H)-yl)acetic acid To a solution of tert-butyl (2,7-dioxo-5,6,7,8-tetrahydro-4H-imidazo[1,5,4-fg][1,6]benzodiazocin-1(2H)-yl)acetate from Step D (15 mg, 0.045 mmol) in $CH_2Cl_2$ (3 mL) was added TFA (1 mL). After 2 h, the mixture was concentrated under reduced pressure to give the title compound. MS: m/z=276 (M+1).

INTERMEDIATE 14

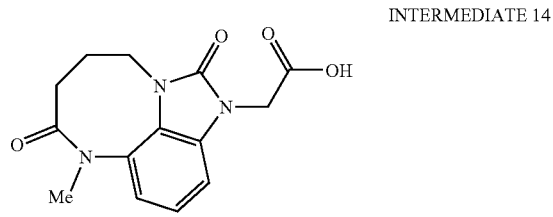

(8-Methyl-2,7-dioxo-5,6,7,8-tetrahydro-4H-imidazo[1,5,4-fg][1,6]benzodiazocin-1(2H)-yl)acetic acid Step A. tert-Butyl (8-methyl-2,7-dioxo-5,6,7,8-tetrahydro-4H-imidazo[1,5,4-fg][1,6]benzodiazocin-1(2H)-yl)acetate Cesium carbonate (214 mg, 0.66 mmol) and iodomethane (93 mg, 0.66 mmol) were added to a solution of tert-butyl (2,7-dioxo-5,6,7,8-tetrahydro-4H-imidazo[1,5,4-fg][1,6]benzodiazocin-1(2H)-yl)acetate (109 mg, 0.33 mmol, described in Intermediate 13) in DMF (5 mL). After 18 h, the mixture was purified directly by HPLC using a reversed phase C18 column and eluting with a gradient of $H_2O:CH_3CN$: $CF_3CO_2H$—90:10:0.1 to 5:95:0.1. Lyophilization provided the title compound. MS: m/z=346 (M+1).

Step B. (8-Methyl-2,7-dioxo-5,6,7,8-tetrahydro-4H-imidazo[1,5,4-fg][1,6]benzodiazocin-1(2H)-yl)acetic acid To a solution of tert-butyl (8-methyl-2,7-dioxo-5,6,7,8-tetrahydro-4H-imidazo[1,5,4-fg][1,6]benzodiazocin-1(2H)-yl)acetate from Step A (45 mg, 0.13 mmol) in $CH_2Cl_2$ (6 mL) was added TFA (2 mL). After 2 h, the mixture was concentrated under reduced pressure to give the title compound. MS: m/z=290 (M+1).

Lithium (7-methyl-4-oxo-4,5-dihydropyrrolo[4,3,2-de]quinolin-1(3H)-yl)acetate

Step A. 2,5-Dimethyl-3-nitroaniline

To a stirred solution of p-xylene (10.4 g, 97.9 mmol) in concentrated sulfuric acid (20 mL), cooled in an ice bath, was added 90% nitric acid (12.4 mL, 264 mmol) dropwise over 50 min. The resulting mixture was heated to 80° C. for 2 h, then poured onto ice and extracted with $CH_2Cl_2$ (2×400 mL). The combined organic extracts were washed with saturated aqueous $NaHCO_3$, then brine, then dried over $Na_2SO_4$, filtered, and concentrated in vacuo. The crude product was partially purified by silica gel chromatography, eluting with a gradient of hexane:EtOAc—90:10 to 60:40. The resulting solid was recrystallized from $CH_2Cl_2$ to yield 2,5-dimethyl-1,3-dinitrobenzene. 2,5-Dimethyl-1,3-dinitrobenzene (3.68 g, 18.8 mmol) was dissolved in AcOH (35 mL) and iron powder (1.95 g, 34.9 mmol) was added. The mixture was heated to 110° C. for 3 h, then filtered through a pad of Celite, washing with EtOAc and $H_2O$. The filtrate was concentrated in vacuo to remove most of the solvent and the residue was partitioned between saturated aqueous $NaHCO_3$ (200 mL) and EtOAc (200 mL). The organic layer was washed with brine, then dried over $Na_2SO_4$, filtered, and concentrated in vacuo. The crude product was purified by silica gel chromatography, eluting with a gradient of hexane:EtOAc—100:0 to 60:40, to give the title compound. MS: m/z=167 (M+1).

Step B. 6-Methyl-4-nitro-1H-indole

A solution of 2,5-dimethyl-3-nitroaniline from Step A (1.21 g, 7.26 mmol) and p-toluenesulfonic acid monohydrate (2 mg, 0.011 mmol) in freshly distilled triethyl orthoformate (1.65 mL, 9.92 mmol) was heated at 120° C. for 45 min in a distillation apparatus, and about 0.4 mL of EtOH distilled over. Vacuum distillation of the residual solution yielded ethyl 2,5-dimethyl-3-nitrophenylimidoformate (b.p.=146° C., ca. 2 mm Hg) as a pale yellow solid. To a solution of diethyl oxalate (868 mg, 5.94 mmol) in DMF (2 mL), at 0° C., was added potassium ethoxide (435 mg, 5.17 mmol) and the resulting solution was added to a solution of ethyl 2,5-dimethyl-3-nitrophenylimidoformate (880 mg, 3.96 mmol) in DMSO (3 mL). The reaction mixture was heated at 40° C. for 1 h than quenched with $H_2O$ (30 mL) and extracted with EtOAc (2×50 mL). The combined organic layers were washed with brine, then dried over $Na_2SO_4$, filtered, and concentrated in vacuo. The crude product was purified by silica gel chromatography, eluting with a gradient of hexane: EtOAc—100:0 to 0:100, to give the title compound. MS: m/z=177 (M+1).

Lithium (7-methyl-4-oxo-4,5-dihydropyrrolo[4,3,2-de]quinolin-1(3H)-yl)acetate

Essentially following the procedures described for Intermediate 11, but using 6-methyl-4-nitro-1H-indole in place of 4-nitroindole, the title compound was prepared. MS: m/z=245 (M+1).

INTERMEDIATE 15

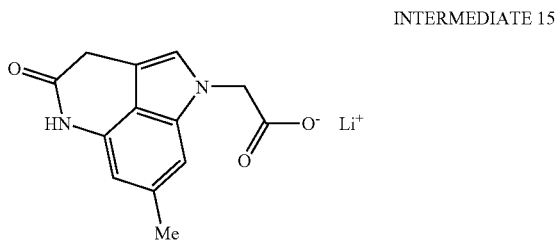

INTERMEDIATE 16

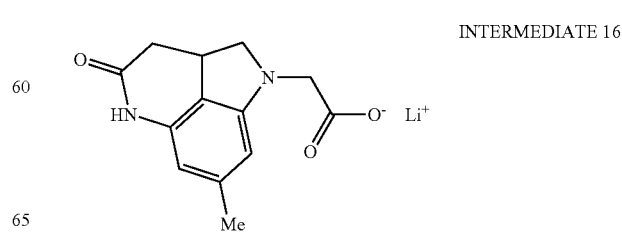

Lithium (7-methyl-4-oxo-2a,3,4,5-tetrahydropyrrolo[4,3,2-de]quinolin-1(2H)-yl)acetate, enantiomer B Essentially following the procedures described for Intermediate 12, but using 6-methyl-4-nitro-1H-indole (described in Intermediate 15) in place of 4-nitroindole, the title compound was prepared. MS: m/z=247 (M+1).

INTERMEDIATE 17

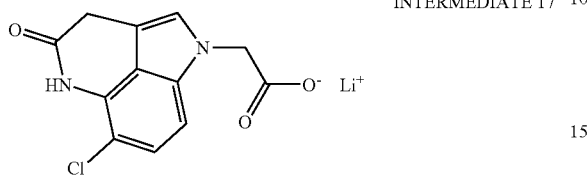

Lithium (6-chloro-4-oxo-4,5-dihydropyrrolo[4,3,2-de]quinolin-1(3H)-yl)acetate

Step A. tert-Butyl [4-amino-3-(cyanomethyl)-1H-indol-1-yl]acetate

A mixture of tert-butyl [3-(cyanomethyl)-4-nitro-1H-indol-1-yl]acetate (700 mg, 2.22 mmol, described in Intermediate 11) and 10% Pd/C (65 mg) in EtOH (20 mL) was stirred under an atmosphere of hydrogen (ca. 1 atm). After 4 h, the reaction was filtered through a Celite pad and concentrated in vacuo to give the title compound. MS: m/z=286 (M+1).

Step B. tert-Butyl [4-amino-5-chloro-3-(cyanomethyl)-1H-indol-1-yl]acetate

To a solution of tert-butyl [4-amino-3-(cyanomethyl)-1H-indol-1-yl]acetate from Step A (150 mg, 0.526 mmol) in CH$_2$Cl$_2$ (5 mL) was added N-chlorosuccinimide (70 mg, 0.526 mmol). The reaction mixture was stirred at ambient temperature for 30 min, then partitioned between saturated aqueous NaHCO$_3$ (5 mL) and CHCl$_3$ (15 mL). The aqueous phase was extracted further with CHCl$_3$ (15 mL) and the combined organic extracts were dried over Na$_2$SO$_4$, filtered, and concentrated in vacuo to give the title compound, which was of sufficient purity for use in the next step. MS: m/z=320 (M+1).

Lithium (6-chloro-4-oxo-4,5-dihydropyrrolo[4,3,2-de]quinolin-1(3H)-yl)acetate

Essentially following the procedures described for Intermediate 11, but using tert-butyl [4-amino-5-chloro-3-(cyanomethyl)-1H-indol-1-yl]acetate in place of tert-butyl [3-(cyanomethyl)-4-nitro-1H-indol-1-yl]acetate, the title compound was prepared. MS: m/z=265 (M+1).

INTERMEDIATE 18

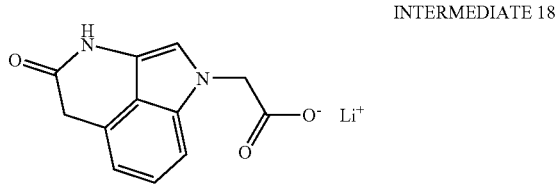

Lithium (4-oxo-4,5-dihydropyrrolo[2,3,4-ij]isoquinolin-1(3H)-yl)acetate

Step A. 4-Bromo-1-(phenylsulfonyl)-1H-indole

To a solution of 4-bromoindole (1.00 g, 5.10 mmol) in DMF (50 mL) at ambient temperature was added sodium hydride (220 mg of a 60% dispersion in mineral oil, 5.50 mmol). The reaction mixture was stirred for 5 min, then benzenesulfonyl chloride (901 mg, 5.10 mmol) was added and stirring was continued for 15 min. The reaction was quenched with saturated aqueous NaHCO$_3$ (50 mL) and extracted with CHCl$_3$ (2×75 mL). The combined organic extracts were dried over Na$_2$SO$_4$, filtered, and concentrated in vacuo. The crude product was purified by silica gel chromatography, eluting with a gradient of hexane:EtOAc—100:0 to 90:10, to give the title compound. MS: n2/z=336 (M+1).

Step B. tert-Butyl [1-(phenylsulfonyl)-1H-indol-4-yl]acetate

To a mixture of 1,3-bis(2,6-diisopropylphenyl)-4,5-dihydroimidazolium tetrafluoroborate (94 mg, 0.196 mmol), tris(dibenzylideneacetone)dipalladium (180 mg, 0.196 mmol), and lithium bis(trimethylsilyl)amide (1.37 M in t-BuOMe, 11.0 mL, 15.1 mmol) were added 4-bromo-1-(phenylsulfonyl)-1H-indole from Step A (2.20 g, 6.54 mmol), tert-butyl acetate (988 mg, 8.51 mmol), and toluene (15 mL). The resulting mixture was stirred at ambient temperature for 18 h then partitioned between Et$_2$O (100 mL) and saturated aqueous NH$_4$Cl (30 mL). The organic layer was washed with brine, then dried over Na$_2$SO$_4$, filtered, and concentrated in vacuo. The crude product was purified by silica gel chromatography, eluting with a gradient of hexane:EtOAc—100:0 to 85:15, to give the title compound. MS: m/z=316 (M–C$_4$H$_7$).

Step C. tert-Butyl [3-nitro-1-(phenylsulfonyl)-1H-indol-4-yl]acetate

To acetic anhydride (5 mL) at 0° C. was added 90% nitric acid (0.183 mL, 3.90 mmol) and the resulting mixture was aged for 10 min, then added dropwise to a solution of tert-butyl [1-(phenylsulfonyl)-1H-indol-4-yl]acetate from Step B (1.00 g, 2.69 mmol) in acetic anhydride (5 mL) at –78° C. The reaction mixture was stirred at –78° C. for 6 h, then aged at –20° C. for 16 h, then quenched with H$_2$O and extracted with EtOAc (2×10 mL). The combined organic extracts were dried over Na$_2$SO$_4$, filtered, and concentrated in vacuo. The crude product was purified by silica gel chromatography, eluting with a gradient of hexane:EtOAc—100:0 to 70:30, to give the title compound. MS: m/z=361 (M–C$_4$H$_7$).

Step D. tert-Butyl [3-nitro-1H-indol-4-yl]acetate

To a solution of tert-butyl [3-nitro-1-(phenylsulfonyl)-1H-indol-4-yl]acetate from Step C (730 mg, 1.75 mmol) in THF (5 mL) was added tetrabutylammonium fluoride (1.0 M in THF, 5.25 mL, 5.25 mmol) and the reaction mixture was stirred at ambient temperature for 10 min, then concentrated in vacuo. The residue was partitioned between saturated aqueous NaHCO$_3$ (5 mL) and extracted with CHCl$_3$ (15 mL). The organic extract was dried over Na$_2$SO$_4$, filtered, and concentrated in vacuo. The crude product was purified by silica gel chromatography, eluting with a gradient of CHCl$_3$:EtOAc—90:10 to 50:50, to give the title compound. MS: m/z=221 (M–C$_4$H$_7$).

Step E. tert-Butyl [1-(2-ethoxy-2-oxoethyl)-3-nitro-1H-indol-4-yl]acetate

To a solution of tert-butyl [3-nitro-1H-indol-4-yl]acetate from Step D (385 mg, 1.39 mmol) in DMF (5 mL) at ambient temperature was added sodium hydride (60 mg of a 60% dispersion in mineral oil, 1.50 mmol). The reaction mixture was stirred for 5 min, then ethyl bromoacetate (256 mg, 1.53 mmol) was added and stirring was continued for 10 min. The reaction was quenched with saturated aqueous NaHCO$_3$ (5 mL) and extracted with CHCl$_3$ (2×25 mL). The combined organic extracts were dried over Na$_2$SO$_4$, filtered, and concentrated in vacuo. The crude product was purified by silica gel chromatography, eluting with a gradient of hexane:EtOAc—90:10 to 40:60, to give the title compound. MS: m/z=307 (M−C$_4$H$_7$).

Step F. [1-(2-Ethoxy-2-oxoethyl)-3-nitro-1H-indol-4-yl]acetic acid

To a solution of tert-butyl [1-(2-ethoxy-2-oxoethyl)-3-nitro-1H-indol-4-yl]acetate from Step E (300 mg, 0.828 mmol) in CH$_2$Cl$_2$ (1 mL) was added TFA (0.63 mL, 8.28 mmol). The mixture was stirred at ambient temperature for 1 h then concentrated in vacuo to give the title compound. MS: m/z=307 (M+1).

Step G. Ethyl (4-oxo-4,5-dihydropyrrolo[2,3,4-ij]isoquinolin-1(3H)-yl)acetate To a solution of [1-(2-ethoxy-2-oxoethyl)-3-nitro-1H-indol-4-yl]acetic acid from Step F (250 mg, 0.816 mmol) in AcOH (18 mL) and H$_2$O (2 mL) was added iron powder (456 mg, 8.16 mmol) and the reaction mixture was heated at 80° C. for 18 h. The mixture was concentrated in vacuo to remove most of the solvent and the residue was partitioned between saturated aqueous NaHCO$_3$ (5 mL) and EtOAc (25 mL). The organic layer was washed with brine, then dried over Na$_2$SO$_4$, filtered, and concentrated in vacuo to give the title compound, which was of sufficient purity for use in the next step. MS: m/z=259 (M+1).

Step H. Lithium (4-oxo-4,5-dihydropyrrolo[2,3,4-ij]isoquinolin-1(3H)-yl)acetate To a solution of ethyl (4-oxo-4,5-dihydropyrrolo[2,3,4-ij]isoquinolin-1(3H)-yl)acetate from Step G (200 mg, 0.77 mmol) in THF (1 mL), EtOH (1 mL) and H$_2$O (1 mL) was added 1.0 N lithium hydroxide (0.85 mL, 0.85 mmol). After 15 min, 1 N aqueous HCl was added to adjust the solution to pH 7 and the mixture was concentrated in vacuo to give the title compound. MS: m/z=231 (M+1).

INTERMEDIATE 19

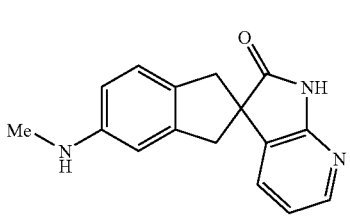

5-(Methylamino)-1,3-dihydrospiro[indene-2,3'-pyrrolo[2,3-b]pyridin]-2'(1'H)-one, enantiomer B A mixture of (−)-5-amino-1,3-dihydrospiro[indene-2,3'-pyrrolo[2,3-b]pyridin]-2'(1'H)-one (154 mg, 0.613 mmol, described in Intermediate 3) and 1-(hydroxymethyl)benzotriazole (93 mg, 0.625 mmol) in EtOH (2 mL) and DMF (0.2 mL) was heated at reflux for 4 h, then concentrated to dryness under reduced pressure. The residue was resuspended in THF (3 mL) and sodium borohydride (40 mg, 1.05 mmol) was added. The resulting mixture was heated to 70° C. for 6 h then quenched with H$_2$O (50 mL) and extracted with EtOAc (50 mL). The organic extract was dried over Na$_2$SO$_4$, filtered, and concentrated in vacuo. The crude product was purified by silica gel chromatography, eluting with a gradient of CH$_2$Cl$_2$:MeOH—100:0 to 80:20, to give the title compound, which was of sufficient purity for use in the next step. MS: m/z=266 (M+1).

INTERMEDIATE 20

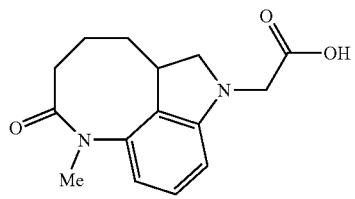

(7-Methyl-6-oxo-2a,3,4,5,6,7-hexahydroazocino[4,3,2-cd]indol-1(2H)-yl)acetic acid, enantiomer A

Step A. Ethyl 4-(4-nitro-1H-indol-3-yl)-4-oxobutanoate

To a stirred solution of 4-nitroindole (2.00 g, 12.3 mmol) in CH$_2$Cl$_2$ (60 mL) at 0° C. was added dimethylaluminum chloride (1 M in hexanes, 14.8 mL, 14.8 mmol) and the mixture was stirred for 30 min. Ethyl 4-chloro-4-oxobutyrate (2.44 g, 14.8 mmol) was added dropwise and the resulting mixture was allowed to warm slowly to ambient temperature and stirred for 18 h. The reaction mixture was carefully quenched with 10% aqueous citric acid (150 mL) and extracted with CH$_2$Cl$_2$ (3×150 mL).

The combined organic extracts were dried over Na$_2$SO$_4$, filtered, and concentrated in vacuo. The residue was partially purified by silica gel chromatography, eluting with a gradient of CH$_2$Cl$_2$:EtOAc—100:0 to 65:35, and the resulting crude product was recrystallized from CH$_2$Cl$_2$:MeOH to give the title compound. MS: m/z=291 (M+1).

Step B. Ethyl 4-(4-nitro-2,3-dihydro-1H-indol-3-yl)butanoate

Triethylsilane (11 mL, 68 mmol) was added to a solution of ethyl 4-(4-nitro-1H-indol-3-yl)-4-oxobutanoate from Step A (960 mg, 3.31 mmol) in TFA (15 mL). After 3 h, the reaction mixture was concentrated in vacuo and the residue was purified by silica gel chromatography, eluting with a gradient of CHCl$_3$:MeOH—100:0 to 94:6, to give the title compound. MS: m/z=279 (M+1).

Step C. Ethyl 4-[1-(2-tert-butoxy-2-oxoethyl)-4-nitro-2,3-dihydro-1H-indol-3-yl]butanoate To a solution of ethyl 4-(4-nitro-2,3-dihydro-1H-indol-3-yl)butanoate from Step B (1.10 g, 3.95 mmol), sodium carbonate (628 mg, 5.93 mmol), and potassium iodide (131 mg, 0.79 mmol) in acetone (10 mL) was added tert-butyl bromoacetate (17.5 mL, 119 mmol). The mixture was heated at reflux for 18 h, then cooled to ambient temperature and concentrated in vacuo. The residue was partitioned between H₂O (30 mL) and EtOAc (2×60 mL) and the organic extracts were dried over Na₂SO₄, filtered, and concentrated in vacuo. The crude product was purified by silica gel chromatography, eluting with a gradient of hexane:EtOAc—90:10 to 65:35, to give the title compound. MS: m/z=393 (M+1).

Step D. Ethyl 4-[4-amino-1-(2-tert-butoxy-2-oxoethyl)-2,3-dihydro-1H-indol-3-yl]butanoate A mixture of ethyl 4-[1-(2-tert-butoxy-2-oxoethyl)-4-nitro-2,3-dihydro-1H-indol-3-yl]butanoate from Step C (1.10 g, 2.80 mmol) and 10% Pd/C (150 mg) in EtOH (50 mL) was stirred under an atmosphere of hydrogen (ca. 1 atm). After 18 h, the reaction was filtered through a Celite pad and concentrated in vacuo to give the title compound. MS: m/z=363 (M+1).

Step E. Lithium 4-[4-amino-1-(2-tert-butoxy-2-oxoethyl)-2,3-dihydro-1H-indol-3-yl]butanoate To a solution of ethyl 4-[4-amino-1-(2-tert-butoxy-2-oxoethyl)-2,3-dihydro-1H-indol-3-yl]butanoate from Step D (1.00 g, 2.76 mmol) in THF (30 mL), EtOH (15 mL) and H₂O (15 mL) was added 1.0 N lithium hydroxide (2.76 mL, 2.76 mmol). After 15 min, 1 N aqueous HCl was added to adjust the solution to pH 7 and the mixture was concentrated in vacuo to give the title compound, which was of sufficient purity for use in the next step. MS: m/z=335 (M+1).

Step F. tert-Butyl (6-oxo-2a,3,4,5,6,7-hexahydroazocino[4,3,2-cd]indol-1(2H)-yl)acetate, enantiomer A A mixture of lithium 4-[4-amino-1-(2-tert-butoxy-2-oxoethyl)-2,3-dihydro-1H-indol-3-yl]butanoate from Step E (900 mg, 2.69 mmol), EDC (1.29 g, 6.73 mmol), HOAT (916 mg, 6.73 mmol), and N,N-diisopropylethylamine (0.94 mL, 5.38 mmol) was stirred in DMF (10 mL) at ambient temperature for 4 h, then concentrated under reduced pressure. The residue was partitioned between saturated aqueous NaHCO₃ (5 mL) and EtOAc (50 mL). The organic layer was washed with H₂O (5 mL), then 10% aqueous citric acid (5 mL), then dried over Na₂SO₄, filtered, and concentrated in vacuo. The crude product was purified by silica gel chromatography, eluting with a gradient of hexane:EtOAc—80:20 to 0:100, to give the racemic product. The enantiomers were resolved by HPLC, utilizing a Chiralpak AS column and eluting with CH₃CN:MeOH—25:75. The first major peak to elute was tert-butyl (6-oxo-2a,3,4,5,6,7-hexahydroazocino[4,3,2-cd]indol-1(2H)-yl)acetate, enantiomer A, the title compound, and the second major peak to elute was tert-butyl (6-oxo-2a,3,4,5,6,7-hexahydroazocino[4,3,2-cd]indol-1(2H)-yl)acetate, enantiomer B. MS: m/z=317 (M+1).

Step G. tert-Butyl (7-methyl-6-oxo-2a,3,4,5,6,7-hexahydroazocino[4,3,2-cd]indol-1(2H)-yl)acetic acid, enantiomer A To a solution of tert-butyl (6-oxo-2a,3,4,5,6,7-hexahydroazocino[4,3,2-cd]indol-1(2H)-yl)acetate, enantiomer A, from Step F (20 mg, 0.063 mmol) in DMF (0.5 mL) at ambient temperature was added sodium hydride (3 mg of a 60% dispersion in mineral oil, 0.075 mmol). The reaction mixture was stirred for 5 min, then iodomethane (10 mg, 0.070 mmol) was added and stirring was continued for 10 min. The reaction was quenched with saturated aqueous NaHCO₃ (1 mL) and extracted with EtOAc (2×3 mL). The combined organic extracts were dried over Na₂SO₄, filtered, and concentrated in vacuo to give the title compound. MS: m/z=331 (M+1).

Step H. (7-Methyl-6-oxo-2a,3,4,5,6,7-hexahydroazocino[4,3,2-cd]indol-1(2H)-yl)acetic acid, enantiomer A A solution of tert-butyl (7-methyl-6-oxo-2a,3,4,5,6,7-hexahydroazocino [4,3,2-cd]indol-1(2H)-yl)acetate, enantiomer A, from Step G (18 mg, 0.057 mmol) in EtOAc (1 mL) was saturated with HCl (g), aged at ambient temperature for 10 min, then resaturated with HCl (g). After a further 10 min, the mixture was concentrated in vacuo to give the title compound. MS: m/z=275 (M+1).

INTERMEDIATE 21

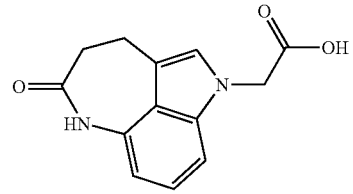

(5-Oxo-3,4,5,6-tetrahydro-1H-azepino[4,3,2-cd]indol-1-yl)acetic acid

Step A. Ethyl 4-(4-nitro-1H-indol-3-yl)propanoate

A mixture of 4-nitroindole (1.00 g, 6.17 mmol), Meldrum's acid (889 mg, 6.17 mmol), proline (36 mg, 0.31 mmol), and formaldehyde (37% in H₂O, 0.50 mL, 6.17 mmol) was stirred in CH₃CN (4 mL) at ambient temperature for 18 h. The reaction mixture was quenched with H₂O (20 mL) and extracted with EtOAc (2×20 mL). The combined organic extracts were dried over Na₂SO₄, filtered, and concentrated in vacuo. After drying under high vacuum, the solid residue was dissolved in pyridine (16 mL) and EtOH (4 mL). To the resulting solution was added copper powder (50 mg, 0.79 mmol) and the mixture was heated at reflux for 2 h then allowed to cool. The solvent was removed in vacuo, and the residue was partitioned between saturated aqueous NaHCO₃ (25 mL) and EtOAc (50 mL). The organic extract was dried over Na₂SO₄, filtered, and concentrated in vacuo. The crude product was purified by silica gel chromatography, eluting with a gradient of hexane:CH₂Cl₂—20:80 to 0:100, to give the title compound. MS: m/z=263 (M+1).

Step B. Ethyl 3-[1-(2-tert-butoxy-2-oxoethyl)-4-nitro-1H-indol-3-yl]propanoate

To a solution of ethyl 4-(4-nitro-1H-indol-3-yl)propanoate from Step A (860 mg, 3.28 mmol) in DMF (15 mL), was added sodium hydride (142 mg of a 60% dispersion in mineral oil, 3.55 mmol). After 5 min, test-butyl bromoacetate (0.581 mL, 3.94 mmol) was added dropwise and the reaction mixture was stirred at room temperature for 10 min then quenched with H₂O and extracted with CHCl₃ (3×35 mL). The combined organic extracts were dried over Na₂SO₄, filtered, and concentrated in vacuo. The crude product was purified by silica gel chromatography, eluting with a gradient of hexane:EtOAc—90:10 to 30:70, to give the title compound. MS: m/z=321 (M−C₄H₇).

Step C. Ethyl 3-[4-amino-1-(2-tert-butoxy-2-oxoethyl)-1H-indol-3-yl]propanoate A mixture of ethyl 3-[1-(2-tert-butoxy-2-oxoethyl)-4-nitro-1H-indol-3-yl]propanoate from Step B (1.20 g, 3.19 mmol) and 10% Pd/C (150 mg) in EtOH (100 mL) was stirred under an atmosphere of hydrogen (ca. 1 atm). After 1 h, the reaction mixture was filtered through a Celite pad and concentrated in vacuo to give the title compound. MS: m/z=347 (M+1).

Step D. tert-Butyl (5-oxo-3,4,5,6-tetrahydro-1H-azepino[4,3,2-cd]indol-1-yl)acetate To a solution of ethyl 3-[4-amino-1-(2-tert-butoxy-2-oxoethyl)-1H-indol-3-yl]propanoate from Step C (1.00 g, 2.89 mmol) in toluene (50 mL) was added p-toluenesulfonic acid monohydrate (5 mg, 0.026 mmol) and the mixture was heated at reflux. After 2 h, the reaction was allowed to cool to ambient temperature and the mixture was washed with saturated aqueous NaHCO$_3$ (10 mL). The organic layer was dried over Na$_2$SO$_4$, filtered, and concentrated in vacuo. The crude product was purified by silica gel chromatography, eluting with a gradient of CH$_2$Cl$_2$:MeOH—100:0 to 92:8, to give the title compound. MS: m/z=301 (M+1).

Step E. (5-Oxo-3,4,5,6-tetrahydro-1H-azepino[4,3,2-cd]indol-1-yl)acetic acid To a solution of tert-butyl (5-oxo-3,4,5,6-tetrahydro-1H-azepino[4,3,2-cd]indol-1-yl)acetate from Step D (100 mg, 0.33 mmol) in (1 mL) was added TFA (0.25 mL, 3.3 mmol) and the resulting mixture was stirred at ambient temperature for 1 h. The mixture was concentrated in vacuo to give the title compound. MS: m/z=245 (M+1).

INTERMEDIATE 22

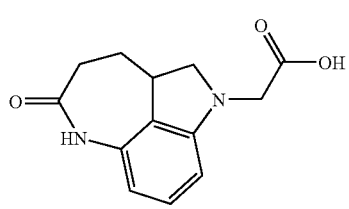

(5-Oxo-2,2a,3,4,5,6-hexahydro-1H-azepino[4,3,2-cd]indol-1-yl)acetic acid, enantiomer A

Step A. (±)-Ethyl 3-(4-nitro-2,3-dihydro-1H-indol-3-yl)propanoate

Triethylsilane (16 mL, 99 mmol) was added to a solution of ethyl 4-(4-nitro-1H-indol-3-yl)propanoate (1.30 g, 4.96 mmol, described in Intermediate 21) in TFA (25 mL). After 1 h, the reaction mixture was concentrated in vacuo and the residue was purified by silica gel chromatography, eluting with a gradient of CHCl$_3$:MeOH—100:0 to 94:6, to give the title compound. MS: m/z=265 (M+1).

Step B. (±)-Ethyl 3-[1(2-tert-butoxy-2-oxoethyl)-4-nitro-2,3-dihydro-1H-indol-3-yl]propanoate To a solution of (±)-ethyl 3-(4-nitro-2,3-dihydro-1H-indol-3-yl)propanoate from Step A (980 mg, 3.71 mmol), sodium carbonate (590 mg, 5.56 mmol), and potassium iodide (123 mg, 0.74 mmol) in acetone (10 mL) was added tert-butyl bromoacetate (16.4 mL, 111 mmol). The mixture was heated at reflux for 18 h, then cooled to ambient temperature and concentrated in vacuo. The residue was partitioned between H$_2$O (30 mL) and EtOAc (2×60 mL) and the organic extracts were dried over Na$_2$SO$_4$, filtered, and concentrated in vacuo. The crude product was purified by silica gel chromatography, eluting with a gradient of hexane:EtOAc—100:0 to 65:35, to give the title compound. MS: m/z=379 (M+1).

(5-Oxo-2,2a,3,4,5,6-hexahydro-1H-azepino[4,3,2-cd]indol-1-yl)acetic acid, enantiomer A Essentially following the procedures described for Intermediate 21, but using (±)-ethyl 3-[1-(2-tert-butoxy-2-oxoethyl)-4-nitro-2,3-dihydro-1H-indol-3-yl]propanoate in place of ethyl 3-[1-(2-tert-butoxy-2-oxoethyl)-4-nitro-1H-indol-3-yl]propanoate, and resolving the racemate into pure enantiomers in analogy with Intermediate 12, the title compound was prepared. MS: m/z=261 (M+1).

INTERMEDIATE 23

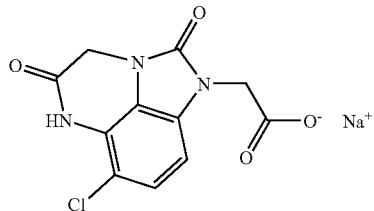

Sodium (7-chloro-2,5-dioxo-5,6-dihydro-4H-imidazo[1,5,4-de]quinoxalin-1(2H)-yl)acetate

Step A. 5-Chloro-2,1,3-benzoselenadiazole

A solution of 4-chlorobenzene-1,2-diamine (1.50 g, 10.5 mmol) in EtOH (15 mL) was heated to reflux and selenium dioxide (1.28 g, 11.5 mmol) was added. The reaction was refluxed for 30 min and cooled to ambient temperature. The precipitated solid was filtered, washed thoroughly with H$_2$O and dried under high vacuum to give the title compound. MS: m/z=219 (M+1).

Step B. 5-Chloro-4-nitro-2,1,3-benzoselenadiazole

A solution of 5-chloro-2,1,3-benzoselenadiazole from Step A (800 mg, 1.80 mmol) in conc. H$_2$SO$_4$ (12 mL) was cooled to 0° C. and 90% HNO$_3$ (0.8 mL) was added. After 30 min the reaction was cooled to 0° C. and diluted with H$_2$O (10 mL). The solid was filtered off and washed with cold H$_2$O to yield the title compound. MS: m/z=264 (M+1).

Step C. 5-Chloro-4-nitro-1,3-dihydro-2H-benzimidazol-2-one

A solution of 5-chloro-4-nitro-2,1,3-benzoselenadiazole from Step B (650 mg, 2.47 mmol) in conc. HCl (4 mL) and 48% aqueous HI (2 mL) was stirred at ambient temperature for 2 h. The reaction was diluted with a 1:1 saturated aqueous solution of NaHSO$_4$ and Na$_2$CO$_3$ (20 mL) and then adjusted to pH 10 using 10 M aqueous NaOH. The mixture was extracted with EtOAc (3×10 mL) and the organic extracts dried over Na$_2$SO$_4$, filtered, and concentrated in vacuo. The resulting dark red solid was dissolved in CH$_3$CN (4 mL) and phosgene was added (20% solution in toluene, 1.5 mL, 3.2 mmol). The reaction mixture was stirred for 1 h, then diluted with toluene. Filtration of the resultant solid gave the title compound. MS: m/z=214 (M+1).

Step D. Dimethyl 2,2'-(5-chloro-4-nitro-2-oxo-1H-benzimidazole-1,3-diyl)diacetate Cesium carbonate (1.16 g, 3.60 mmol) was added to a solution of 5-chloro-4-nitro-1,3-dihydro-2H-benzimidazol-2-one from Step C (255 mg, 1.20 mmol) and methyl bromoacetate (0.23 mL, 2.40 mmol) in DMF (5 mL). After 1.5 h, the reaction was quenched with $H_2O$ (30 mL) and the solid precipitate was collected by filtration to give the title compound. MS: m/z=358 (M+1).

Step E. Methyl (7-chloro-2,5-dioxo-5,6-dihydro-4H-imidazo[1,5,4-de]quinoxalin-1(2H)-yl)acetate To a solution of dimethyl 2,2'-(5-chloro-4-nitro-2-oxo-1H-benzimidazole-1,3-diyl)diacetate (100 mg, 0.28 mmol) from Step D in AcOH (1.0 mL) and water (0.1 mL) was added fine granular iron (78 mg, 1.4 mmol) and the slurry was heated at 70° C. for 1 h. The reaction was cooled, filtered, concentrated and dissolved in DMF (4 mL). The DMF solution was added dropwise to $H_2O$ (30 mL) with stirring and the precipitate was isolated by filtration to give the title compound. MS: m/z=296 (M+1).

Step F. Sodium (7-chloro-2,5-dioxo-5,6-dihydro-4H-imidazo[1,5,4-de]quinoxalin-1(2H)-yl)acetate Essentially following the procedures described for Intermediate 10, but using methyl (7-chloro-2,5-dioxo-5,6-dihydro-4H-imidazo[1,5,4-de]quinoxalin-1(2H)-yl)acetate in place of methyl (6-methyl-2,5-dioxo-5,6-dihydro-4H-imidazo[1,5,4-de]quinoxalin-1(2H)-yl)acetate, the title compound was prepared MS: m/z=282 (M+1).

INTERMEDIATE 24

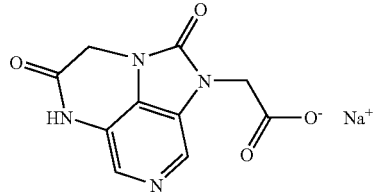

Sodium (2,4-dioxo-4,5-dihydro-3H-1,2a,5,7-tetraazaacenaphthylen-1(2H)-yl)acetate

Step A. 2,6-Dichloro-3-nitro-pyridin-4-amine

To a solution of 2,6-dichloro-4-aminopyridine (5.0 g, 30.6 mmol) in conc. $H_2SO_4$ (25 mL) at 0° C. in an ice-acetone bath was added 90% $HNO_3$ (10 mL) dropwise. The reaction mixture was warmed to ambient temperature and stirred for 1 h then poured onto ice (100 g). The solid precipitate was isolated by filtration, washed with cold $H_2O$ and dried under high vacuum. The resulting solid was dissolved in conc. $H_2SO_4$ (50 mL) and heated at 100° C. for 20 min. The reaction mixture was poured onto ice (150 g) and neutralized with conc. $NH_4OH$ while maintaining the temperature below 20° C. The precipitate was isolated by filtration, washed with cold $H_2O$, and dried to yield the title compound. MS: m/z=208 (M+1).

Step B. 2,6-Dichloro-pyridine-3,4-diamine

To a solution of 2,6-dichloro-3-nitro-pyridin-4-amine (2.6 g, 14.4 mmol) from Step A in MeOH (150 mL) was added Raney Nickel catalyst (2 g) and the reaction agitated under a hydrogen atmosphere in a Parr apparatus (35 p.s.i.) for 2 h. The reaction mixture was filtered through a pad of Celite and concentrated to yield the title compound. MS: m/z=178 (M+1).

Step C. 4,6-Dichloro-1,3-dihydro-2H-imidazo[4,5-c]pyridin-2-one

A mixture of 2,6-dichloro-3,4-dihydropyridine-3,4-diamine (500 mg, 2.8 mmol) from Step B and urea (1.0 g, 16.8 mmol) was stirred as a melt at 165° C. for 4 h, then cooled and $H_2O$ (100 mL) was added. The aqueous mixture was heated at reflux until all solid dissolved and the solution was allowed to cool and aged for 18 h. The precipitate was isolated by filtration to give the title compound. MS: m/z=204 (M+1).

Step D. 4,6-Dichloro-7-nitro-1,3-dihydro-2H-imidazo[4,5-c]pyridin-2-one

To a solution of 4,6-dichloro-1,3-dihydro-2H-imidazo[4,5-c]pyridin-2-one (0.6 g, 2.94 mmol) from Step C in conc. $H_2SO_4$ (15 mL) was added $KNO_3$ (2.97 g, 29.4 mmol) and the reaction mixture was heated at 125° C. for 2 h. After cooling, the reaction was mixed with ice and the solid precipitate was isolated by filtration and washed with cold $H_2O$ to give the title compound. MS: m/z 290 (M+1+$CH_3CN$).

Step E. Dimethyl 2,2'-(4,6-dichloro-7-nitro-2-oxo-1H-imidazo[4,5-c]pyridine-1,3-diyl)diacetate Cesium carbonate (2.39 g, 7.33 mmol) was added to a solution of 4,6-dichloro-7-nitro-1,3-dihydro-2H-imidazo[4,5-c]pyridin-2-one from Step D (610 mg, 2.45 mmol) and methyl bromoacetate (0.47 mL, 5.02 mmol) in DMF (5 mL). After 1.5 h, the reaction was quenched with $H_2O$ (30 mL) and the solid precipitate was collected by filtration to give the title compound. MS: m/z=392 (M+1).

Step F. Methyl (2,4-dioxo-4,5-dihydro-3H-1,2a,5,7-tetraazaacenaphthylen-1(2H)-yl)acetate A mixture of dimethyl 2,2'-(4,6-dichloro-7-nitro-2-oxo-1H-imidazo[4,5-c]pyridine-1,3-diyl)diacetate (40 mg, 0.10 mmol) from Step E and 10% Pd/C (12 mg) in MeOH (2 mL) was stirred under an atmosphere of hydrogen (ca. 1 atm) for 6 h. The reaction mixture was filtered through a pad of Celite and concentrated in vacuo. The crude material was heated at 80° C. for 2 h in toluene (2 mL) and AcOH (2 mL) then concentrated to give the title compound. MS: m/z=263 (M+1).

Step G. Sodium (2,4-dioxo-4,5-dihydro-3H-1,2a,5,7-tetraazaacenaphthylen-1(2H)-yl)acetate Essentially following the same procedures described for Intermediate 9, but using methyl (6,8-dichloro-2,4-dioxo-4,5-dihydro-3H-1,2a,5,7-tetraazaacenaphthylen-1(2H)-yl)acetate in place of methyl (2,5-dioxo-5,6-dihydro-4H-imidazo[1,5,4-de]quinoxalin-1(2H)-yl)acetate, the title compound was prepared. MS: m/z=249 (M+1).

INTERMEDIATE 25

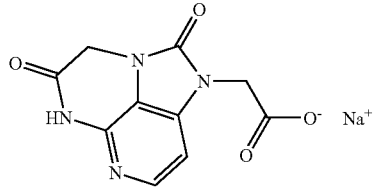

Sodium (2,4-dioxo-4,5-dihydro-3H-1,2a,5,6-tetraazaacenaphthylen-1(2H)-yl)acetate Step A.
1,3-Dihydro-2H-imidazo[4,5-c]pyridin-2-one A combination of pyridine-3,4-diamine (1.0 g, 9.16 mmol) and urea (3.3 g, 54.9 mmol) were stirred as a melt at 165° C. for 4 h, then cooled and H$_2$O (100 mL) was added. The aqueous mixture was heated at reflux until all solid dissolved and the solution was allowed to cool and aged for 18 h. The precipitate was isolated by filtration to give the title compound. MS: m/z=136 (M+1).

Step B. Sodium (2,4-dioxo-4,5-dihydro-3H-1,2a,5,6-tetraazaacenaphthylen-1(2H)-yl)acetate Essentially following the procedures described for Intermediate 24, but using 1,3-dihydro-2H-imidazo[4,5-c]pyridin-2-one in place of 4,6-dichloro-1,3-dihydro-2H-imidazo[4,5-c]pyridin-2-one, the title compound was prepared. MS: m/z=249 (M+1).

INTERMEDIATE 26

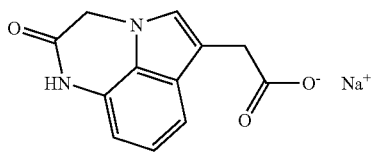

Sodium (2-oxo-2,3-dihydro-1H-pyrrolo[1,2,3-de]quinoxalin-6-yl)acetate

Step A.
N,N-Dimethyl-1-(7-nitro-1H-indol-3-yl)methanamine

A mixture of 7-nitro-1H-indole (3 g, 18.5 mmol), 40% aqueous dimethylamine (3.12 mL, 27.7 mmol) and 37% aqueous formaldehyde (1.57 mL, 19.3 mmol) was stirred for three days at ambient temperature. The reaction mixture was diluted with H$_2$O (20 mL) followed 15% aqueous NaOH (200 mL) and extracted with CHCl$_3$ (3×200 mL). The combined organic extracts were dried over Na$_2$SO$_4$, filtered, and concentrated in vacuo to give the title compound in sufficient purity for use in the next step. MS: m/z=181 (M+1).

Step B. Methyl (7-nitro-1H-indol-3-yl)acetate

A solution of N,N-dimethyl-1-(7-nitro-1H-indol-3-yl)methanamine from Step A (3.3 g, 18.5 mmol) in DMF (3 mL), H$_2$O (3 mL), THF (150 mL) and iodomethane (2.85 mL, 45.7 mmol) was heated at reflux for 15 min as a white precipitate formed. Potassium cyanide (6.0 g, 92.1 mmol) was added and reflux was continued for 2 h. The cooled solution was filtered and concentrated under reduced pressure and the residue was triturated with MeOH to give (7-nitro-1H-indol-3-yl)acetonitrile as a yellow solid. A suspension of this solid in MeOH (10 mL) was cooled to 0° C. and HCl (g) was bubbled in slowly for 30 min. The reaction mixture was aged for 1 h, then concentrated in vacuo. To the residue was added 6 M aqueous HCl (20 mL) and the mixture was extracted with EtOAc (3×20 mL). The combined organic extracts were washed with saturated aqueous NaHCO$_3$ (50 mL), then brine (20 mL), dried over Na$_2$SO$_4$, filtered, and concentrated to give the title compound. MS: m/z=235 (M+1).

Step C. Dimethyl 2,2'-(7-nitro-1H-indole-1,3-diyl)diacetate

To a solution of methyl (7-nitro-1H-indol-3-yl)acetate from Step B (545 mg, 2.71 mmol) was added cesium carbonate (927 mg, 2.85 mmol) and methyl bromoacetate (0.26 mL, 2.84 mmol) in DMF (10 mL). The reaction mixture was stirred at ambient temperature for 18 h, then quenched with H$_2$O (50 mL). The solid precipitate was collected by filtration to give the title compound. MS: m/z=308 (M+1).

Step D. Sodium (2-oxo-2,3-dihydro-1H-pyrrolo[1,2,3-de]quinoxalin-6-yl)acetate

Essentially following the procedures described for Intermediate 9, but using dimethyl 2,2'-(7-nitro-1H-indole-1,3-diyl)diacetate in place of dimethyl 2,2'-(4-nitro-2-oxo-1H-benzimidazole-1,3-diyl)diacetate, the title compound was prepared. MS: m/z=231 (M+1).

Intermediates 27-41

Essentially following analogous procedures to those outlined for Intermediates 9-26, the compounds listed in Table 1 were prepared. The most relevant analogous procedure for each intermediate is listed in the Table. The requisite starting materials were commercially available, described in the literature, or readily synthesized by one skilled in the art of organic synthesis. In some cases, straightforward protecting group strategies were applied. The references detailed in the Table are provided as a guide to relevant synthetic methodology.

TABLE 1

R$^a$ ─ CH$_2$ ─ C(O) ─ OH

| Intermediate | R$^a$ | MS (M + 1) | Relevant Intermediate(s) | Literature Reference |
| --- | --- | --- | --- | --- |
| 27 |  | 230 | 11 | Teranishi et al., Syntheisis, 1995, 506-508 |

TABLE 1-continued $$R^a\text{—CH}_2\text{—COOH}$$

| Intermediate | $R^a$ | MS (M + 1) | Relevant Intermediate(s) | Literature Reference |
| --- | --- | --- | --- | --- |
| 28 | | 247 | 12, 21 | |
| 29 | | 245 | 11, 21 | |
| 30 | | 261 | 20 | |
| 31 | | 259 | 26 | |
| 32 | | 330 | 10 | |
| 33 | | 326 | 23 | |
| 34 | | 278 | 23 | |

TABLE 1-continued

| Intermediate | R$^a$ | MS (M + 1) | Relevant Intermediate(s) | Literature Reference |
|---|---|---|---|---|
| 35 | | 296 | 23 | |
| 36 | | 296 | 23 | |
| 37 | | 262 | 9 | Lyle & LaMattina J. Org. Chem. 1975, 40, 438-441. |
| 38 | | 276 | 10 | Lyle & LaMattina J. Org. Chem. 1975, 40, 438-441. |
| 39 | | 263 | 10, 25 | |
| 40 | | 263 | 10, 24 | |

TABLE 1-continued

| Intermediate | $R^a$ | MS (M + 1) | Relevant Intermediate(s) | Literature Reference |
|---|---|---|---|---|
| 41 | (2-isopropyl-4-oxo-4,5-dihydropyrrolo[4,3,2-de]quinolin-1(3H)-yl structure with N-Me lactam fused to pyrrole) | 273 | 10, 26 | |

INTERMEDIATE 42

Lithium (2-isopropyl-4-oxo-4,5-dihydropyrrolo[4,3,2-de]quinolin-1(3H)-yl)acetate

Step A. (2E)-3-Methylbutan-2-one (3-nitrophenyl)hydrazone

A mixture of isopropyl methyl ketone (2.5 g, 29 mol), 3-nitrophenylhydrazine hydrochloride (6.1 g, 32 mmol) and sodium acetate trihydrate (4.8 g, 35 mmol) in H₂O (50 mL) and EtOH (50 mL) was stirred at 80° C. for 1 h. The reaction mixture was cooled and then concentrated under reduced pressure. The residue was partitioned between saturated aqueous NaHCO3 (100 mL) and CHCl₃ (150 mL). The organic layer was removed and the aqueous phase was further extracted with CHCl₃ (100 mL). The combined organic extracts were dried over Na₂SO₄, filtered, and concentrated in vacuo to give the title compound. MS: m/z=222 (M+1).

Step B. 2-Isopropyl-4-nitro-1H-indole

A mixture of (2E)-3-methylbutan-2-one (3-nitrophenyl) hydrazone from Step A (6.0 g, 27 mmol) and polyphosphoric acid (25 mL) was heated at 90° C. for 2 h with mechanical stirring. The reaction mixture was poured into ice water and extracted with EtOAc (750 mL). The organic layer was washed with dilute aqueous NaOH, then dried over Na₂SO₄, filtered, and concentrated in vacuo to give the title compound in sufficient purity for use in the next step. MS: m/z=205 (M+1).

Step C. (2-Isopropyl-4-nitro-1H-indol-3-yl)acetonitrile

Essentially following the procedures described for Intermediate 11, but using 2-isopropyl-4-nitro-1H-indole from Step B in place of 4-nitroindole, the title compound was prepared. MS: m/z=244 (M+1).

Step D. (2-Isopropyl-4-nitro-1H-indol-3-yl)acetic acid

A solution of (2-isopropyl-4-nitro-1H-indol-3-yl)acetonitrile from Step C (1.20 g, 4.93 mmol) in 3 N aqueous HCl (200 mL) was heated to 95° C. for 72 h. The cooled mixture was made basic by addition of 10 N aqueous NaOH and washed with EtOAc (2×100 mL). The aqueous layer was adjusted to pH 2 with 1 N aqueous HCl and extracted with EtOAc (3×200 mL). The combined organic extracts were dried over Na₂SO₄, filtered, and concentrated in vacuo to give the title compound, which was of sufficient purity for use in the next step. MS: m/z=263 (M+1).

Step E. Ethyl (2-isopropyl-4-nitro-1H-indol-3-yl)acetate

A solution of (2-isopropyl-4-nitro-1H-indol-3-yl)acetic acid from Step D (500 mg, 1.91 mmol) and conc. H₂SO₄ (0.5 mL) in EtOH (100 mL) was heated at reflux for 1 h. The cooled mixture was partially concentrated in vacuo, made basic by addition of saturated aqueous NaHCO₃ and washed with CHCl₃ (4×30 mL). The combined organic extracts were dried over Na₂SO₄, filtered, and concentrated in vacuo to give the title compound, which was of sufficient purity for use in the next step. MS: m/z=291 (M+1).

Step F. Diethyl 2,2'-(2-isopropyl-4-nitro-1H-indole-1,3-diyl)diacetate

Sodium hydride (45 mg of a 60% dispersion in mineral oil, 1.13 mmol) was added to a solution of ethyl (2-isopropyl-4-nitro-1H-indol-3-yl)acetate from Step E (300 mg, 1.03 mmol) in DMF (10 mL). After 5 min, ethyl bromoacetate (0.126 mL, 1.13 mmol) was added dropwise and the reaction mixture was stirred at ambient temperature for 30 min. The reaction mixture was quenched with saturated aqueous NaHCO₃ (10 mL) and extracted with CHCl₃ (3×25 mL). The combined organic extracts were washed with brine, dried over Na₂SO₄, filtered, and concentrated in vacuo. The crude product was purified by silica gel chromatography, eluting with a gradient of CHCl₃:MeOH—100:0 to 95:5, to give the title compound. MS: m/z=377 (M+1).

Lithium (2-isopropyl-4-oxo-4,5-dihydropyrrolo[4,3,2-de]quinolin-1(3H)-yl)acetate Essentially following the procedures described for Intermediate 11, but using diethyl 2,2'-(2-isopropyl-4-nitro-1H- indole-1,3-diyl)diacetate from Step F in place of diethyl 2,2'-(4-nitro-1H-indole-1,3-diyl)diacetate, the title compound was prepared. MS: m/z=273 (M+1).

INTERMEDIATE 43

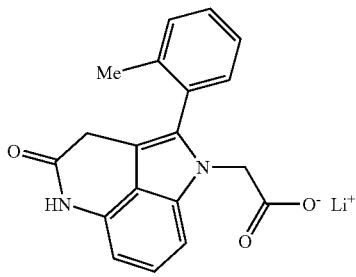

Lithium [2-(2-methylphenyl)-4-oxo-4,5-dihydropyrrolo[4,3,2-de]quinolin-1(3H)-yl]acetate Step A. Ethyl (4-nitro-1H-indol-3-yl)acetate Essentially following the procedures described for Intermediate 42, but using (4-nitro-1H-indol-3-yl)acetonitrile (described in Intermediate 11) in place of (2-isopropyl-4-nitro-1H-indol-3-yl)acetonitrile, the title compound was prepared. MS: m/z=249 (M+1).

Step B. Ethyl (2-bromo-4-nitro-1H-indol-3-yl)acetate

To a solution of ethyl (4-nitro-1H-indol-3-yl)acetate from Step A (1.00 g, 4.03 mmol) in AcOH (40 mL) was added N-bromosuccinimide (789 mg, 4.43 mmol) in AcOH (40 mL) dropwise over 30 min. The resulting mixture was stirred at ambient temperature for 1 h, then concentrated to dryness under reduced pressure. The crude product was purified by silica gel chromatography, eluting with a gradient of $CHCl_3$:EtOAc—100:0 to 80:20, to give the title compound. MS: m/z=327 (M+1).

Step C. Ethyl [2-(2-methylphenyl)-4-nitro-1H-indol-3-yl]acetate

To a deoxygenated solution of ethyl (2-bromo-4-nitro-1H-indol-3-yl)acetate from Step B (250 mg, 0.76 mmol), 2-methylphenylboronic acid (156 mg, 1.15 mmol), and $Na_2CO_3$ (202 mg, 1.91 mmol) in EtOH (10 mL), toluene (10 mL) and $H_2O$ (0.5 mL) was added tetrakis(triphenylphosphine)palladium (44 mg, 0.038 mmol) and the resulting mixture was heated at reflux for 18 h. The cooled mixture was diluted with $H_2O$ (20 mL) and extracted with EtOAc (2×50 mL), and the combined organic extracts were dried over $Na_2SO_4$, filtered, and concentrated in vacuo. The crude product was purified by silica gel chromatography, eluting with a gradient of $CHCl_3$:EtOAc—100:0 to 80:20, to give the title compound. MS: m/z=339 (M+1).

Lithium [2-(2-methylphenyl)-4-oxo-4,5-dihydropyrrolo[4,3,2-de]quinolin-1(3H)-yl]acetate Essentially following the procedures described for Intermediate 42, but using ethyl [2-(2-methylphenyl)-4-nitro-1H-indol-3-yl]acetate from Step C in place of ethyl (2-isopropyl-4-nitro-1H-indol-3-yl)acetate, the title compound was prepared. MS: m/z=321 (M+1).

INTERMEDIATE 44

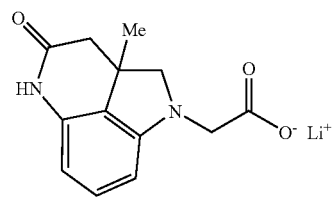

Lithium (2a-methyl-4-oxo-2a,3,4,5-tetrahydropyrrolo[4,3,2-de]quinolin-1(2H)-yl)acetate, enantiomer A Step A. 4-Nitro-1,3-dihydro-2H-indol-2-one A mixture of 4-nitroindole (12.2 g, 75.2 mmol) and N-chlorosuccinimide (6.07 g, 30.1 mmol) in $CHCl_3$ (500 mL) was heated at reflux for 30 h, then concentrated under reduced pressure to give an orange solid. The solid was dissolved in AcOH (200 mL) and the resulting solution was warmed to 70° C., then 85% $H_3PO_4$ (80 mL) was added over 2 min. The mixture was heated to reflux for 90 min then cooled on ice. The cooled mixture was adjusted to pH 6 by addition of 10 N NaOH (450 mL), followed by aqueous $NaHCO_3$, keeping the temperature below 30° C. The mixture was extracted with EtOAc (3×1 L) and the combined organic extracts were dried over $Na_2SO_4$, filtered, and concentrated in vacuo. The crude product was partially purified by silica gel chromatography, eluting with a gradient of hexane:EtOAc-100:0 to 0:100, and then triturated with MeOH to give the title compound. MS: m/z=179 (M+1).

Step B. (±)-Diethyl 2,2'-(3-methyl-4-nitro-2-oxo-2,3-dihydro-1H-indole-1,3-diyl)diacetate To a stirred solution of 4-nitro-1,3-dihydro-2H-indol-2-one from Step A (3.83 g, 21.5 mmol) in DMF (150 mL) at 0° C. was added sodium hydride (60% dispersion in mineral oil; 903 mg, 22.6 mmol) and the resulting mixture was stirred for 20 min. Iodomethane (1.34 mL, 21.5 mmol) was added dropwise, and the mixture was stirred at 0° C. for 1 h. Sodium hydride (60% dispersion in mineral oil; 1.80 g, 45.0 mmol) was added and the mixture was allowed to warm to ambient temperature for 20 min, then recooled to 0° C. Ethyl bromoacetate (5.23 mL, 47.3 mmol) was added dropwise over 5 min. The reaction mixture was stirred at 0° C. for 1 h, then quenched with saturated aqueous $NH_4Cl$ (200 mL). The mixture was extracted with EtOAc (500 mL) and the organic extract was washed with $H_2O$ (100 mL), brine (100 mL), then dried over $Na_2SO_4$, filtered, and concentrated in vacuo. The crude product was purified by silica gel chromatography, eluting with a gradient of hexane:EtOAc—100:0 to 0:100, to give the title compound. MS: m/z=365 (M+1).

Step C. (±)-Diethyl 2,2'-(3-methyl-4-nitro-2-thioxo-2,3-dihydro-1H-indole-1,3-diyl)diacetate A mixture of (±)-diethyl 2,2'-(3-methyl-4-nitro-2-oxo-2,3-dihydro-1H-indole-1,3-diyl)diacetate from Step B (2.30 g, 6.31 mmol) and Lawesson's reagent (1.53 g, 3.79 mmol) was heated at 150° C. in xylenes (120 mL) for 18 h. The reaction mixture was concentrated in vacuo and the residue was purified by silica gel chromatography, eluting with a gradient of hexane:EtOAc—100:0 to 0:100, to give the title compound. MS: m/z=381 (M+1).

Step D. (±)-Diethyl 2,2'-(4-amino-3-methyl-2,3-dihydro-1H-indole-1,3-diyl)diacetate To a solution of (±)-diethyl 2,2'-(3-methyl-4-nitro-2-thioxo-2,3-dihydro-1H-indole-1,3-diyl)diacetate from Step C (900 mg, 6.31 mmol) in THF (40 mL) was added activated Raney nickel (ca. 4 g) and the reaction mixture was stirred at ambient temperature for 10 min. The reaction mixture was filtered through a pad of Celite, washing with THF. EtOAc (100 mL) was added to the filtrate and the mixture was concentrated under reduced pressure to a volume of about 100 mL. This mixture was diluted with EtOAc (300 mL) and washed with saturated aqueous NaHCO$_3$ (100 mL), brine (100 mL), then dried over Na$_2$SO$_4$, filtered, and concentrated in vacuo. The crude product was purified by silica gel chromatography, eluting with a gradient of hexane:EtOAc— 100:0 to 50:50, to give the title compound. MS: m/z=321 (M+1).

Step E. Ethyl (2a-methyl-4-oxo-2a,3,4,5-tetrahydropyrrolo[4,3,2-de]quinolin-1(2H)-yl)acetate, enantiomer A To a solution of diethyl 2,2'-(4-amino-3-methyl-2,3-dihydro-1H-indole-1,3-diyl)diacetate from Step D (410 mg, 1.28 mmol) in toluene (100 mL) was added p-toluenesulfonic acid monohydrate (10 mg, 0.052 mmol) and the mixture was heated at reflux. After 20 min, the reaction was allowed to cool to ambient temperature and the mixture was partitioned between EtOAc (300 mL) and aqueous NaHCO$_3$ (50 mL). The organic layer was washed with brine, dried over Na$_2$SO$_4$, filtered, and concentrated in vacuo. The crude product was purified by silica gel chromatography, eluting with a gradient of CH$_2$Cl$_2$:EtOAc—100:0 to 0:100, to give the racemic product. The enantiomers were resolved by HPLC, utilizing a Chiralpak AS column and eluting with hexane:EtOH 40:60. The first major peak to elute was ethyl (2a-methyl-4-oxo-2a,3,4,5-tetrahydropyrrolo[4,3,2-de]quinolin-1(2H)-yl)acetate, enantiomer A, the title compound, and the second major peak to elute was ethyl (2a-methyl-4-oxo-2a,3,4,5-tetrahydropyrrolo[4,3,2-de]quinolin-1(2H)-yl)acetate, enantiomer B. MS: m/z=275 (M+1).

Step F. Lithium (2a-methyl-4-oxo-2a,3,4,5-tetrahydropyrrolo[4,3,2-de]quinolin-1(2H)-yl)acetate, enantiomer A Essentially following the procedures described for Intermediate 12, but using ethyl (2a-methyl-4-oxo-2a,3,4,5-tetrahydropyrrolo[4,3,2-de]quinolin-1(2H)-yl)acetate, enantiomer A, from Step E in place of ethyl (4-oxo-2a,3,4,5-tetrahydropyrrolo[4,3,2-de]quinolin-1(2H)-yl)acetate, enantiomer B, the title compound was prepared. MS: m/z=247 (M+1).

INTERMEDIATE 45

Lithium [2-(3-pyridyl)-4-oxo-4,5-dihydropyrrolo[4,3,2-de]quinolin-1(3H)-yl]acetate Essentially following the procedures described for Intermediate 43, but using 3-pyridineboronic acid in place of 2-methylphenylboronic acid, the title compound was prepared. MS: m/z=308 (M+1).

INTERMEDIATE 46

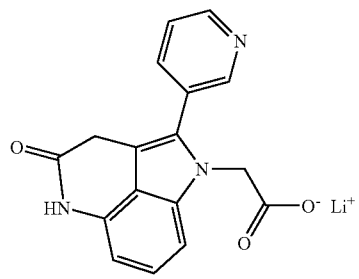

(±)-(2a-Methyl-2,4-dioxo-2a,3,4,5-tetrahydropyrrolo[4,3,2-de]quinolin-1(2H)-yl)acetic acid

Step A. (±)-Ethyl (3-methyl-4-nitro-2-oxo-2,3-dihydro-1H-indol-3-yl)acetate

To a stirred solution of 4-nitro-1,3-dihydro-2H-indol-2-one (6.95 g, 39.0 mmol, described in Intermediate 44) in DMF (180 mL) at 0° C. was added sodium hydride (60% dispersion in mineral oil; 1.72 g, 42.9 mmol) and the resulting mixture was stirred for 30 min. Iodomethane (2.43 mL, 39.0 mmol) in DMF (20 mL) was added dropwise over 20 min, and the mixture was stirred at 0° C. for 1 h. A further equivalent of sodium hydride (60% dispersion in mineral oil; 1.56 g, 39.0 mmol) was added and stirring was continued for 1 h. Ethyl bromoacetate (3.46 mL, 31.2 mmol) in DMF (20 mL) was added dropwise over 20 min The reaction mixture was stirred at 0° C. for 1 h, then quenched with saturated aqueous NH$_4$Cl (500 mL). The mixture was extracted with EtOAc (3×500 mL) and the combined organic extracts were washed with brine (100 mL), then dried over Na$_2$SO$_4$, filtered, and concentrated in vacuo. The crude product was purified by silica gel chromatography, eluting with a gradient of hexane: EtOAc—100:0 to 0:100, to give the title compound. MS: n2/z=279 (M+1).

Step B. (±)-Ethyl (4-amino-3-methyl-2-oxo-2,3-dihydro-1H-indol-3-yl)acetate

A mixture of (±)-ethyl (3-methyl-4-nitro-2-oxo-2,3-dihydro-1H-indol-3-yl)acetate from Step A (2.66 g, 9.56 mmol) and 10% Pd/C (500 mg) was stirred vigorously in MeOH (50 mL) under an atmosphere of hydrogen (ca. 1 atm). After 3 h, the mixture was filtered through a pad of Celite, washing with MeOH, and the filtrate was concentrated in vacuo to give the title compound. MS: m/z=249 (M+1).

Step C. (±)-2a-Methyl-2a,5-dihydropyrrolo[4,3,2-de]quinoline-2,4(1H,3H)-dione A mixture of (±)-ethyl (4-amino-3-methyl-2-oxo-2,3-dihydro-1H-indol-3-yl)acetate from Step B (2.37 g, 9.56 mmol) and AcOH (1 mL) was heated in xylenes (10 mL) at reflux for 24 h, then concentrated to dryness under reduced pressure. The crude product was partially purified by silica gel chromatography, eluting with a gradient of CH$_2$Cl$_2$: MeOH:NH$_4$OH—100:0:0 to 90:9:1, to give a crude sample of the title compound. Further purification by silica gel chromatography, eluting with a gradient of CH$_2$Cl$_2$:EtOAc-100:0 to 0:100, gave the title compound. MS: m/z=203 (M+1).

Step D. (±)-tert-Butyl (2a-methyl-2,4-dioxo-2a,3,4,5-tetrahydropyrrolo[4,3,2-de]quinolin-1(2H)-yl)acetate Sodium hydride (71 mg of a 60% dispersion in mineral oil, 1.78 mmol) was added to a solution of (±)-2a-methyl-2a,5-dihydropyrrolo[4,3,2-de]quinoline-2,4(1H,3H)-dione from Step C (298 mg, 1.47 mmol) in DMF (3 mL) at 0° C. After 1 h, tert-butyl bromoacetate (0.219 mL, 1.48 mmol) was added dropwise and the reaction mixture was stirred at ambient temperature for 3 h. The reaction mixture was quenched with H$_2$O (5 mL) and extracted with CH$_2$Cl$_2$ (3×10 mL) then EtOAc (3×10 mL). The combined organic extracts were dried over Na$_2$SO$_4$, filtered, and concentrated in vacuo. The crude product was purified by silica gel chromatography, eluting with a gradient of CH$_2$Cl$_2$:EtOAc—100:0 to 50:50, to give the title compound. MS: m/z=317 (M+1).

Step. E. (±)-(2a-Methyl-2,4-dioxo-2a,3,4,5-tetrahydropyrrolo[4,3,2-de]quinolin-1(2H)-yl)acetic acid Essentially following the procedures described for Intermediate 20, but using (±)-tert-butyl (2a-methyl-2,4-dioxo-2a,3,4,5-tetrahydropyrrolo[4,3,2-de]quinolin-1(2H)-yl)acetate from Step E in place of tert-butyl (7-methyl-6-oxo-2a,3,4,5,6,7-hexahydroazocino[4,3,2-cd]indol-1(2H)-yl)acetate, enantiomer A, the title compound was prepared. MS: m/z=261 (M+1).

Example 1

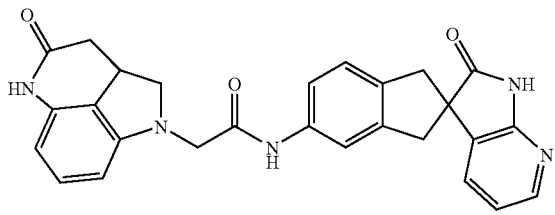

2-(4-Oxo-2a,3,4,5-tetrahydropyrrolo[4,3,2-de]quinolin-1(2H)-yl)-N-(2'-oxo-1,1',2',3-tetrahydrospiro[indene-2,3'-pyrrolo[2,3-b]pyridin]-5-yl)acetamide, diastereomer B A mixture of (−)-5-amino-1,3-dihydrospiro [indene-2,3'-pyrrolo[2,3-b]pyridin]-2'(1'H)-one (108 mg, 0.431 mmol, described in Intermediate 3), lithium (4-oxo-2a,3,4,5-tetrahydropyrrolo[4,3,2-de]quinolin-1(2H)-yl)acetate, enantiomer B (100 mg, 0.431 mmol, described in Intermediate 12), EDC (107 mg, 0.560 mmol), HOBT (86 mg, 0.560 mmol), and N,N-diisopropylethylamine (0.113 mL, 0.646 mmol) was stirred in DMF (3 mL) at ambient temperature for 18 h. The reaction mixture was purified directly by HPLC using a reversed phase C18 column and eluting with a gradient of H$_2$O:CH$_3$CN:CF$_3$CO$_2$H—90:10:0.1 to 5:95:0.1. The pure, product-containing fractions were combined and concentrated in vacuo. The residue was added to saturated aqueous NaHCO$_3$ (10 mL) and extracted with EtOAc (3×20 mL). The combined organic extract was dried over Na$_2$SO$_4$, filtered, and concentrated in vacuo to give the title compound. MS: m/z=466 (M+1). HRMS: m/z=466.1913; calculated m/z=466.1874 for C$_{27}$H$_{24}$N$_5$O$_3$.

Example 2

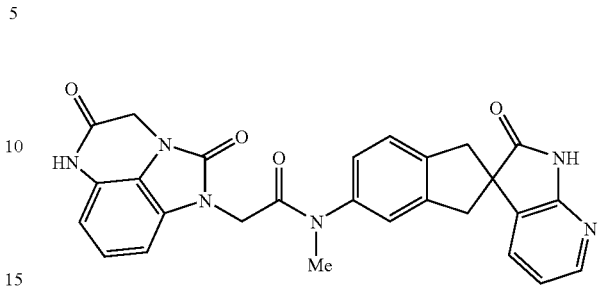

2-(2,5-Dioxo-5,6-dihydro-4H-imidazo[1,5,4-de]quinoxalin-1(2H)-yl)-N-methyl-N-(2'-oxo-1,1',2'3-tetrahydrospiro[indene-2,3'-pyrrolo[2,3-b]pyridin]-5-yl)acetamide, enantiomer B A mixture of 5-(methylamino)-1,3-dihydrospiro[indene-2,3'-pyrrolo[2,3-b]pyridin]-2'(1'H)-one, enantiomer B (14 mg, 0.053 mmol, described in Intermediate 19), (2,5-dioxo-5,6-dihydro-4H-imidazo[1,5,4-de]quinoxalin-1(2H)-yl)acetic acid (14 mg, 0.058 mmol, described in Intermediate 9), PyBOP (41 mg, 0.079 mmol), and N,N-diisopropylethylamine (0.028 mL, 0.158 mmol) was stirred in DMF (1 mL) at 50° C. for 20 h. The reaction mixture was purified directly by HPLC using a reversed phase C18 column and eluting with a gradient of H$_2$O:CH$_3$CN:CF$_3$CO$_2$H—90:10:0.1 to 5:95:0.1. The pure, product-containing fractions were combined and lyophilized to give the title compound. MS: m/z=495 (M+1). HRMS: m/z=495.1778; calculated m/z=495.1776 for C$_{27}$H$_{23}$N$_5$O$_4$.

Example 3

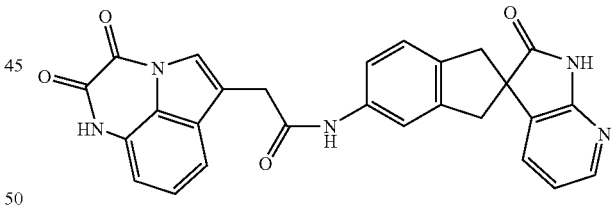

2-(2,3-Dioxo-2,3-dihydro-1H-pyrrolo[1,2,3-de]quinoxalin-6-yl)-N-(2'-oxo-1,1',2'3-tetrahydrospiro[indene-2,3'-pyrrolo[2,3-b]pyridin]-5-yl)acetamide A solution of sodium (2-oxo-2,3-dihydro-1H-pyrrolo[1,2,3-de]quinoxalin-6-yl)acetate (45 mg, 0.195 mmol, described in Intermediate 26), (−)-5-amino-1,3-dihydrospiro[indene-2,3'-pyrrolo[2,3-b]pyridin]-2'(1 H)-one (59 mg, 0.235 mmol, described in Intermediate 3), EDC (75 mg, 0.391 mmol), and HOBT (60 mg, 0.391 mmol) in DMF (12 mL) and TFA (0.1 mL) was stirred for 18 h. The reaction mixture was purified directly by reversed phase C18 column and eluting with a gradient of H$_2$O:CH$_3$CN:CF$_3$CO$_2$H—90:10:0.1 to 5:95:0.1. The pure, product-containing fractions were combined and lyophilized to give the title compound. MS:

m/z=478 (M+1). HRMS: m/z=478.1524; calculated m/z=478.1510 for $C_{27}H_{20}N_5O_4$.

Example 4

Essentially following the procedures outlined for Example 1, but using Intermediate 8 in place of Intermediate 3, the compounds listed in Table 2 were prepared. The requisite carboxylic acids were commercially available, described in the literature, synthesized according to methodology described herein (vide supra), or readily synthesized by one skilled in the art of organic synthesis. In some cases, straightforward protecting group strategies were applied.

TABLE 2

| Example | $R^b$ | MS (M + 1) |
|---|---|---|
| 4 | | 446 |

Examples 5-6

Essentially following the procedures outlined for Example 1, but using Intermediate 4 in place of Intermediate 3, the compounds listed in Table 3 were prepared. The requisite carboxylic acids were commercially available, described in the literature, synthesized according to methodology described herein (vide supra), or readily synthesized by one skilled in the art of organic synthesis. In some cases, straightforward protecting group strategies were applied.

TABLE 3

| Example | $R^b$ | MS (M + 1) |
|---|---|---|
| 5 | | 482 |
| 6 | | 496 |

Example 7-37

Essentially following the procedures outlined for Example 1 the compounds listed in Table 4 were prepared. The requisite carboxylic acids were commercially available, described in the literature, synthesized according to methodology described herein (vide supra), or readily synthesized by one skilled in the art of organic synthesis. In some cases, straightforward protecting group strategies were applied.

TABLE 4

| Example | $R^b$ | MS (M + 1) |
|---|---|---|
| 7 | | 481 |
| 8 | | 495 |
| 9 | | 464 |
| 10 | | 463 |

TABLE 4-continued
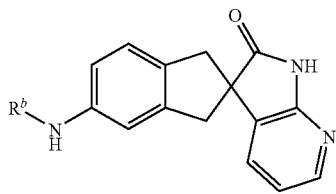
| Example | $R^b$ | MS (M + 1) |
|---|---|---|
| 11 | | 478 |
| 12 | | 464 |
| 13 | | 495 |
| 14 | | 509 |
| 15 | | 530 |
| 16 | | 482 |
TABLE 4-continued
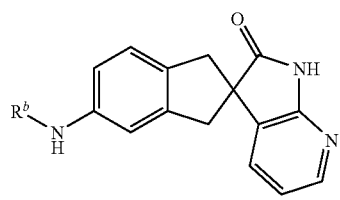
| Example | $R^b$ | MS (M + 1) |
|---|---|---|
| 17 | | 496 |
| 18 | | 482 |
| 19 | | 496 |
| 20 | | 563 |
| 21 | | 530 |
| 22 | | 516 |

TABLE 4-continued
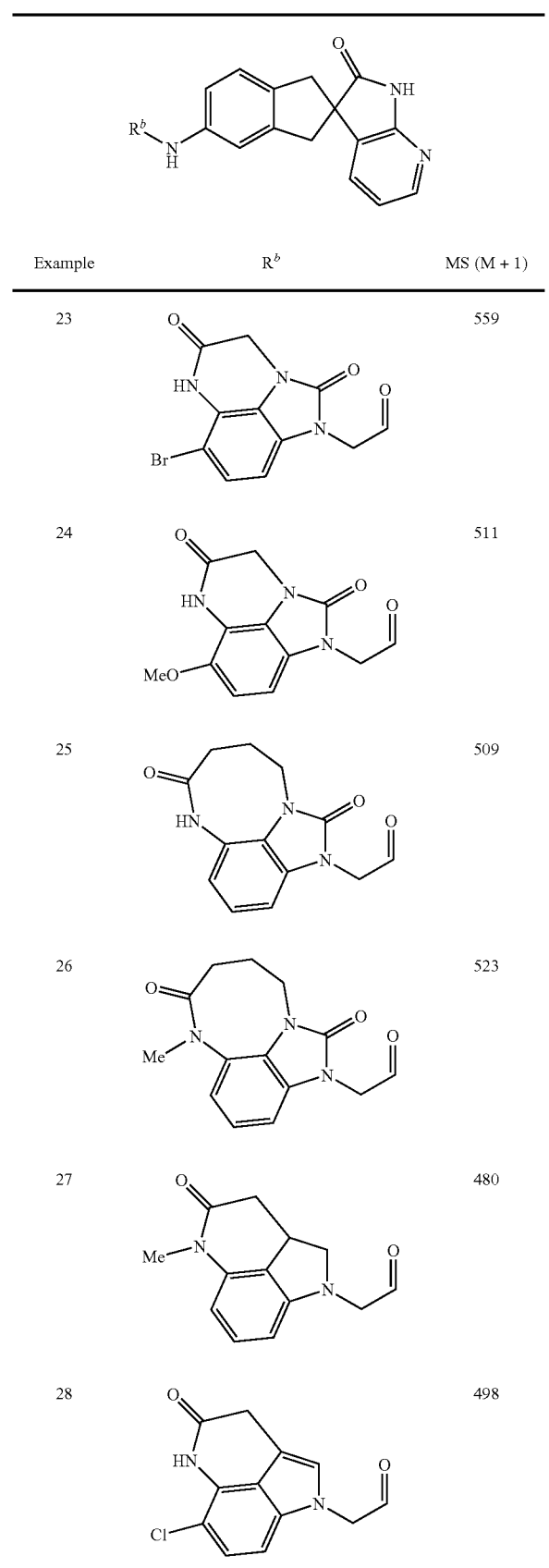
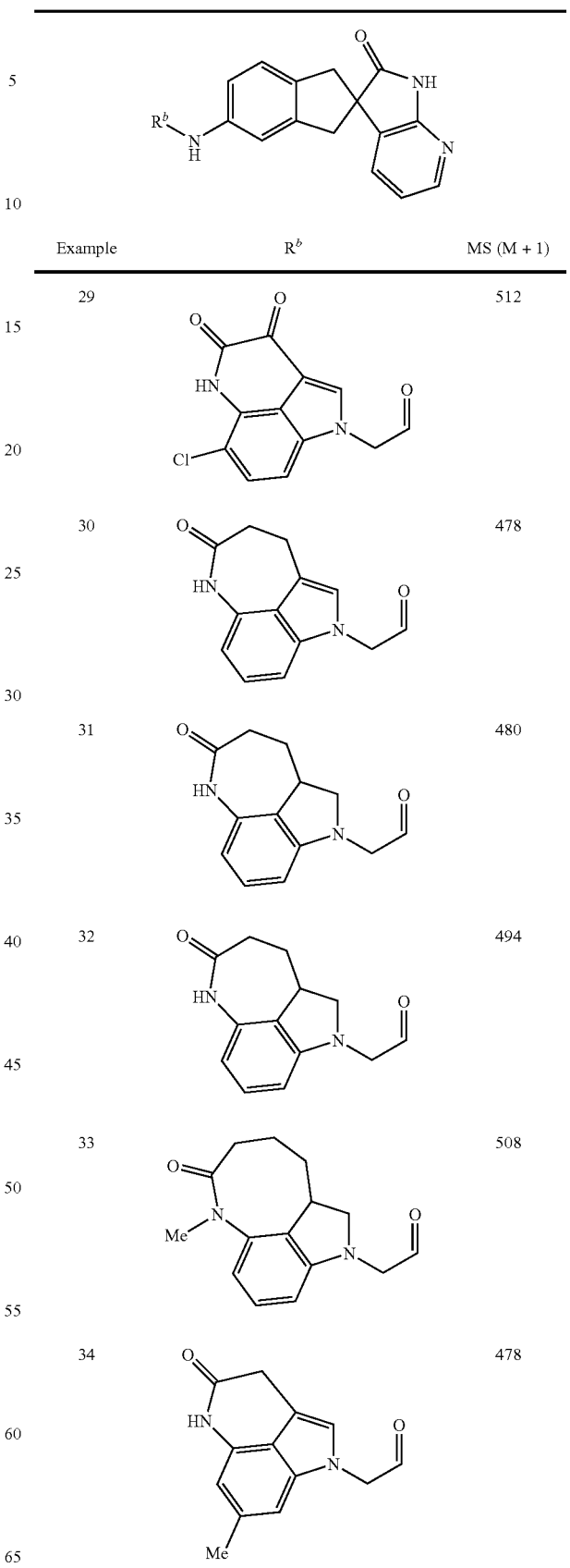

TABLE 4-continued

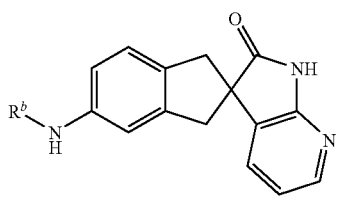

| Example | R<sup>b</sup> | MS (M + 1) |
|---|---|---|
| 35 | 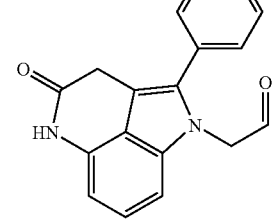 | 480 |
| 36 | 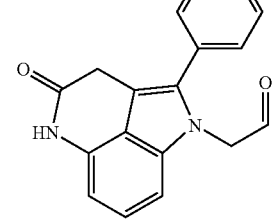 | 492 |
| 37 | 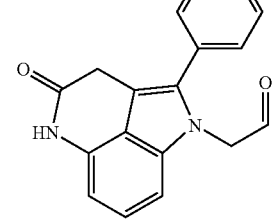 | 506 |
| 38 | 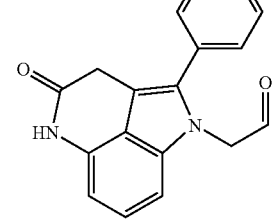 | 506 |
| 39 | 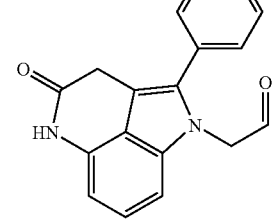 | 554 |

TABLE 4-continued

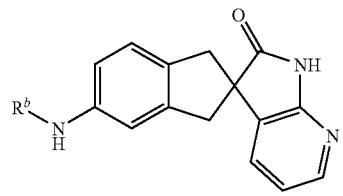

| Example | R$^b$ | MS (M + 1) |
|---|---|---|
| 40 | 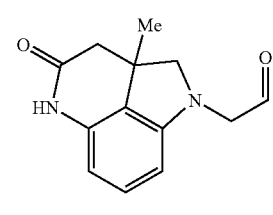 | 541 |
| 41 | 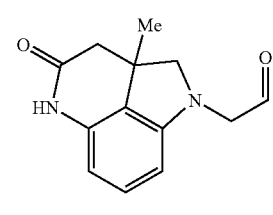 | 480 |
| 42 | 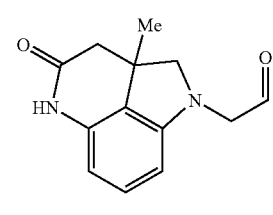 | 494 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of formula I:

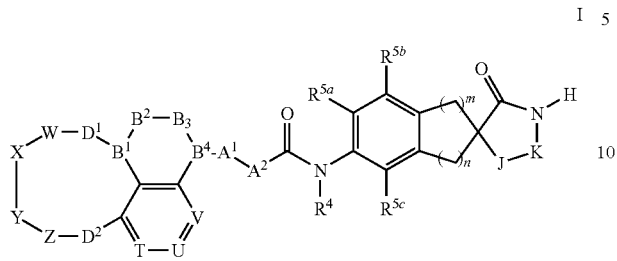

wherein:
one of $A^1$ and $A^2$ is —$CR^{13}R^{14}$— and the other is a bond;
$B^1$ and $B^4$ are each independently selected from:

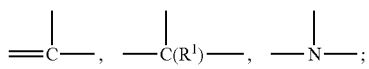

$B^2$ and $B^3$ are each independently selected from: a bond, =$C(R^1)$—, —$C(R^1R^2)$—, —$C(=O)$—, —$C(=S)$— and —$C(=NR^1)$—;

$D^1$ and $D^2$ are each independently selected from: =$C(R^1)$—, —$C(R^1R^2)$—, —$C(=O)$—, —$C(=S)$—, —$C(=NR^1)$—, =N— and —$N(R^1)$—;

J is selected from: =$C(R^{6a})$—, —$C(R^{13}R^{14})$— and —$C(=O)$—;

K is selected from: =$C(R^{6b})$—, —$C(R^{13}R^{14})$— and —$C(=O)$—;

T, U and V are each independently selected from: =$C(R^1)$— and =N—, wherein at least one but no more than two of T, U, and V is =N—;

W, X, Y, and Z are each independently selected from: a bond, =$C(R^1)$—, —$C(R^1R^2)$—, —$C(=O)$—, —$C(=S)$— and —$C(=NR^1)$—;

$R^1$ and $R^2$ are each independently selected from:
(1) hydrogen;
(2) —$C_{1-6}$alkyl, which is unsubstituted or substituted with 1-7 substituents each independently selected from:
(a) halo,
(b) hydroxy,
(c) —O—$C_{1-6}$alkyl,
(d) —$C_{3-6}$cycloalkyl,
(e) phenyl or heterocycle, wherein heterocycle is selected from: azetidinyl, imidazolyl, oxazolyl, pyridyl, pyrimidinyl, pyrazinyl, pyridazinyl, piperidinyl, azepanyl, piperazinyl, pyrazolyl, pyrrolidinyl, thiazolyl, thienyl, triazolyl, tetrazolyl, tetrahydrofuryl and morpholinyl, which phenyl or heterocycle is unsubstituted or substituted with 1-5 substituents each independently selected from: —$C_{1-6}$alkyl, —O—$C_{1-6}$alkyl, halo, hydroxy, trifluoromethyl, —$OCF_3$ and oxo,
(f) —$CO_2R^9$, wherein $R^9$ is independently selected from: hydrogen, —$C_{3-6}$cycloalkyl, benzyl, phenyl and —$C_{1-6}$alkyl which is unsubstituted or substituted with 1-6 fluoro,
(g) —$NR^{10}R^{11}$ wherein $R^{10}$ and $R^{11}$ are each independently selected from: hydrogen, —$C_{5-6}$ cycloalkyl, benzyl, phenyl, —$COR^9$, —$SO_2R^{12}$, and —$C_{1-6}$alkyl which is unsubstituted or substituted with 1-6 fluoro,
(h) —$SO_2R^{12}$ wherein $R^{12}$ is selected from: —$C_{1-6}$alkyl which is unsubstituted or substituted with 1-6 fluoro, —$C_{5-6}$cycloalkyl, benzyl and phenyl,
(i) —$CONR^{10a}R^{11a}$, wherein $R^{10a}$ and $R^{11a}$ are each independently selected from: hydrogen, —$C_{1-6}$alkyl which is unsubstituted or substituted with 1-6 fluoro, —$C_{5-6}$cycloalkyl, benzyl and phenyl,
or $R^{10a}$ and $R^{11a}$ are joined to form a ring selected from azetidinyl, pyrrolidinyl, piperidinyl, piperazinyl and morpholinyl, which ring is unsubstituted or substituted with 1-5 substituents each independently selected from: —$C_{1-6}$alkyl, —O—$C_{1-6}$alkyl, halo, hydroxyl, phenyl and benzyl,
(j) trifluoromethyl,
(k) —$OCO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) —O—$C_{3-6}$cycloalkyl,
(3) —$C_{3-6}$cycloalkyl, which is unsubstituted or substituted with 1-7 substituents each independently selected from:
(a) halo,
(b) hydroxy,
(c) —O—$C_{1-6}$ alkyl,
(d) trifluoromethyl, and
(e) phenyl, which is unsubstituted or substituted with 1-5 substituents each independently selected from: —$C_{1-6}$alkyl, —O—$C_{1-6}$alkyl, halo, hydroxy and trifluoromethyl,
(4) —$C_{2-6}$alkynyl, which is unsubstituted or substituted with 1-7 substituents each independently selected from:
(a) halo,
(b) hydroxy,
(c) —O—$C_{1-6}$ alkyl,
(d) —$C_{3-6}$cycloalkyl,
(d) trifluoromethyl, and
(e) phenyl, which is unsubstituted or substituted with 1-5 substituents each independently selected from: —$C_{1-6}$alkyl, —O—$C_{1-6}$alkyl, halo, hydroxy and trifluoromethyl,
(5) phenyl or heterocycle, wherein heterocycle is selected from: pyridyl, pyrimidinyl, pyrazinyl, thienyl, pyridazinyl, pyrrolidinyl, azepanyl, azetidinyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-dioxolanyl, oxadiazolyl, piperidinyl, tetrahydropyranyl, tetrahydrothienyl, tetrahydrothiopyranyl and morpholinyl, which phenyl or heterocycle is unsubstituted or substituted with 1-5 substituents each independently selected from:
(a) —$C_{1-6}$alkyl which is unsubstituted or substituted with 1-6 fluoro,
(b) halo,
(c) hydroxy, (d) —O—$C_{1-6}$alkyl which is unsubstituted or substituted with 1-6 fluoro,
(e) —$C_{3-6}$cycloalkyl,
(f) phenyl or heterocycle, wherein heterocycle is selected from: pyridyl, pyrimidinyl, pyrazinyl, thienyl and morpholinyl,
  which phenyl or heterocycle is unsubstituted or substituted with 1-5 substituents each independently selected from: —$C_{1-6}$alkyl, —O—$C_{1-6}$alkyl, halo, hydroxy and trifluoromethyl,
(g) —$CO_2R^9$,
(h) —$(CO)R^9$,
(i) —$NR^{10}R^{11}$,
(j) —$CONR^{10}R^{11}$,
(k) oxo
(l) —$SR^{12}$,
(m) —$S(O)R^{12}$,
(n) —$SO_2R^{12}$, and
(o) —CN
(6) halo,
(7) oxo,
(8) hydroxy,
(9) —O—$C_{1-6}$alkyl which is unsubstituted or substituted with 1-5 halo,
(10) —CN,
(11) —$CO_2R^9$,
(12) —$NR^{10}R^{11}$,
(13) —$SO_2R^{12}$,
(14) —$CONR^{10a}R^{11a}$,
(15) —$OCO_2R^9$,
(16) —$(NR^{10a})CO_2R^9$,
(17) —$O(CO)NR^{10a}R^{11a}$,
(18) —$(NR^9)(CO)NR^{10a}R^{11a}$,
(19) —$(CO)-(CO)NR^{10a}R^{11a}$,
(20) —$(CO)-(CO)OR^9$, and
(21) —$(NR^{10})(CO)R^9$;
$R^4$ is selected from: hydrogen, $C_{1-6}$ alkyl which is unsubstituted or substituted with 1-6 fluoro, $C_{5-6}$ cycloalkyl, benzyl and phenyl;
$R^{5a}$, $R^{5b}$ and $R^{5c}$ are each independently selected from: hydrogen, $C_{1-6}$ alkyl, —O—$C_{1-6}$alkyl, —$OCF_3$, trifluoromethyl, halo, hydroxy and —CN;
$R^{6a}$ and $R^{6b}$ are each independently selected from:
(1) hydrogen;
(2) —$C_{1-4}$alkyl which is unsubstituted or substituted with 1-5 substituents each independently selected from:
  (a) halo,
  (b) —O—$C_{1-6}$alkyl,
  (c) —$C_{3-6}$cycloalkyl,
  (d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl, which phenyl or heterocycle is unsubstituted or substituted with 1-3 substituents each independently selected from: —$C_{1-6}$alkyl, —O—$C_{1-6}$alkyl, halo, hydroxy, trifluoromethyl and —$OCF_3$,
(3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl and morpholinyl, which phenyl or heterocycle is unsubstituted or substituted with 1-3 substituents each independently selected from:
  (a) —$C_{1-4}$alkyl which is unsubstituted or substituted with 1-5 fluoro,
  (b) halo,
  (c) hydroxy,
  (d) —O—$C_{1-4}$alkyl which is unsubstituted or substituted with 1-5 fluoro,
  (e) —$C_{3-6}$cycloalkyl, and
  (f) phenyl,
(4) halo,
(5) hydroxy,
(6) —O—$C_{1-6}$alkyl which is unsubstituted or substituted with 1-5 halo,
(7) —CN,
(8) —$CO_2R^9$,
(9) —$NR^{10}R^{11}$, and
(10) —$CONR^{10a}R^{11a}$;
or $R^{6a}$ and $R^{6b}$ and the atom(s) to which they are attached are joined to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —$C_{1-6}$alkyl which is unsubstituted or substituted with 1-3 substituents each independently selected from:
  (i) halo,
  (ii) hydroxy,
  (iii) —O—$C_{1-6}$alkyl,
  (iv) —$C_{3-6}$cycloalkyl,
  (v) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
  (vi) —$CO_2R^9$,
  (vii) —$NR^{10}R^{11}$,
  (viii) —$SO_2R^{12}$,
  (ix) —$CONR^{10a}R^{11a}$, and
  (x) —$(NR^{10a})CO_2R^9$,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —$C_{3-6}$cycloalkyl, —$C_{1-6}$alkyl which is unsubstituted or substituted with 1-6 fluoro, and —O—$C_{1-6}$alkyl which is unsubstituted or substituted with 1-6 fluoro,
(c) halo,
(d) —$SO_2R^{12}$,
(e) hydroxy,
(f) —O—$C_{1-6}$alkyl which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;

$R^{13}$ and $R^{14}$ are each independently selected from: hydrogen, hydroxyl, halo and $C_{1-6}$ alkyl which is unsubstituted or substituted with 1-6 fluoro;

m is 1;

n is 1;

or a pharmaceutically acceptable salt, individual enantiomer or individual diastereomer thereof.

2. The compound of claim 1 having the formula Ia:

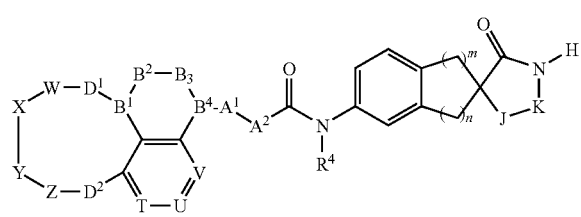

Ia or a pharmaceutically acceptable salt, individual enantiomer or individual diastereomer thereof.

3. The compound of claim 1 having the formula Ib:

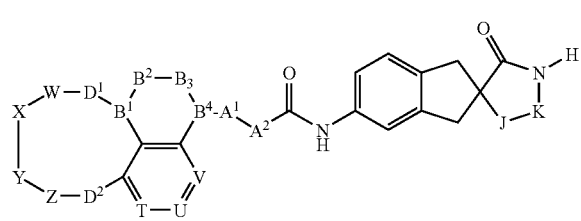

Ib or a pharmaceutically acceptable salt, individual enantiomer or individual diastereomer thereof.

4. The compound of claim 1 having the formula Ic:

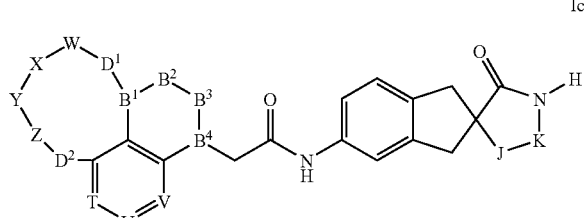

Ic or a pharmaceutically acceptable salt, individual enantiomer or individual diastereomer thereof.

5. The compound of claim 1 having the formula Id:

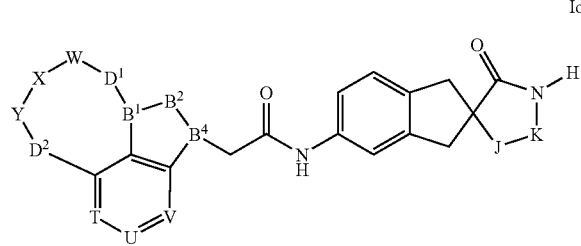

Id or a pharmaceutically acceptable salt, individual enantiomer or individual diastereomer thereof.

6. The compound of claim 1 having the formula Ie:

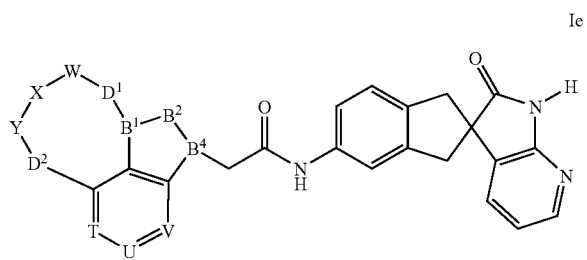

Ie or a pharmaceutically acceptable salt, individual enantiomer or individual diastereomer thereof.

7. The compound of claim 1, wherein $A^1$ is $CH_2$ and $A^2$ is a bond.

8. The compound of claim 1, wherein $B^3$ is a bond.

9. The compound of claim 1, wherein $D^1$ is selected from: —C($R^1R^2$)— and —N($R^1$)—.

10. The compound of claim 1, wherein $D^2$ is selected from: —C($R^1R^2$)— and —N($R^1$)—.

11. The compound of claim 1, wherein T is selected from: =C($R^1$)— and =N—; U is selected from: =C($R^1$)— and =N—; V is =C(H)—; and W is selected from: a bond, —C($R^1R^2$)— and —C(=O)—.

12. The compound of claim 1, wherein $R^1$ and $R^2$ are independently selected from:

(1) hydrogen;

(2) —$C_{1-6}$alkyl, which is unsubstituted or substituted with 1-5 substituents each independently selected from:

(a) halo, (b) hydroxy, (c) —O—$C_{1-6}$alkyl, (d) —$C_{3-6}$cycloalkyl, (e) phenyl or heterocycle, wherein heterocycle is selected from: azetidinyl, imidazolyl, oxazolyl, pyridyl, pyrimidinyl, pyrazinyl, piperidinyl, piperazinyl, pyrrolidinyl, thiazolyl, thienyl, triazolyl, tetrazolyl, tetrahydrofuryl and morpholinyl, which is unsubstituted or substituted with 1-3 substituents each independently selected from: —$C_{1-4}$alkyl, —O—$C_{1-4}$alkyl, halo, hydroxy, trifluoromethyl and —$OCF_3$, (f) —$CO_2R^9$, wherein $R^9$ is independently selected from: hydrogen, and —$C_{1-4}$alkyl, (g) —$NR^{10}R^{11}$, wherein $R^{10}$ and $R^{11}$ are each independently selected from: hydrogen, —$COR^9$, —$SO_2R^{12}$, and —$C_{1-4}$alkyl which is unsubstituted or substituted with 1-3 fluoro, (h) —$CONR^{10a}R^{11a}$, wherein $R^{10a}$ and $R^{11a}$ are each independently selected from: hydrogen, —$C_{1-4}$alkyl which is unsubstituted or substituted with 1-3 fluoro, and —$C_{5-6}$cycloalkyl, or where $R^{10a}$ and $R^{11a}$ are joined to form a ring selected from azetidinyl, pyrrolidinyl, piperidinyl, piperazinyl and morpholinyl, which is unsubstituted or substituted with 1-3 substituents each independently selected from: —$C_{1-4}$alkyl, —O—$C_{1-4}$alkyl, halo and hydroxyl, (i) —($NR^{10a}$)$CO_2R^9$, (3) —$C_{3-6}$cycloalkyl, which is unsubstituted or substituted with 1-3 substituents each independently selected from: halo, hydroxy and —O—$C_{1-6}$alkyl, (4) phenyl or heterocycle, wherein heterocycle is selected from: pyridyl, pyrimidinyl, pyrazinyl, thienyl, pyrrolidinyl, azetidinyl, thiazolyl, oxazolyl, isoxazolyl, imidazolyl, triazolyl, tetrazolyl, benzimidazolyl, benzoxazolyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, quinazolinyl, tetrahydrofuryl, naphthyridinyl, quinoxalinyl, 1,3-dioxolanyl, oxadiazolyl, piperidinyl, tetrahydropyranyl, and morpholinyl, which is unsubstituted or substituted with 1-3 substituents each independently selected from: —$C_{1-4}$alkyl which is unsubstituted or substituted with 1-3 fluoro, —O—$C_{1-4}$-alkyl, which is unsubstituted or substituted with 1-6 fluoro, halo, hydroxy, —$C_{3-6}$cycloalkyl, —$CO_2R^9$, —$NR^{10}R^{11}$ and —$CONR^1OR^{11}$, (5) halo,
(6) hydroxy,
(7) —O—$C_{1-4}$alkyl, which is unsubstituted or substituted with 1-3 halo,
(8) —CN,
(9) —$CO_2R^9$,
(10) —$NR^{10}R^{11}$,
(11) —$CONR^{10a}R^{11a}$, and
(12) —$(NR^{10a})CO_2R^9$.

13. The compound of claim 1, wherein $R^4$ is selected from: hydrogen and —$C_{1-6}$alkyl, which is unsubstituted or substituted with fluoro.

14. The compound of claim 1, wherein $R^{5a}$, $R^{5b}$ and $R^{5c}$ are independently selected from hydrogen, $C_{1-6}$alkyl and halo.

15. The compound of claim 1, wherein $R^{6a}$ and $R^{6b}$ are independently selected from:
   (1) hydrogen;
   (2) —$C_{1-4}$-alkyl which is unsubstituted or substituted with 1-3 substituents each independently selected from: halo, —O—$C_{1-6}$alkyl, —$C_{3-6}$cycloalkyl, and phenyl,
   (3) phenyl or heterocycle, wherein heterocycle is selected from: pyridyl, pyrimidinyl, pyrazinyl, thiazolyl, oxazolyl, tetrahydrofuryl, piperidinyl and morpholinyl, which phenyl or heterocycle is unsubstituted or substituted with 1-3 substituents each independently selected from: halo, hydroxy, —$C_{1-4}$-alkyl which is unsubstituted or substituted with 1-3 fluoro, and —O—$C_{1-4}$alkyl which is unsubstituted or substituted with 1-3 fluoro,
   (4) halo,
   (5) —$NR^{10}R^{11}$,
   (6) hydroxy,
   (7) —O—$C_{1-4}$alkyl which is unsubstituted or substituted with 1-3 halo.

16. The compound of claim 1, wherein $R^{6a}$ and $R^{6b}$ and the atom(s) to which they are attached are joined to form a ring selected from phenyl, pyridyl, pyrimidinyl, pyrazinyl, pyridazinyl, thiazolyl, oxazolyl, imidazolyl and thienyl, which ring is unsubstituted or substituted with 1-3 substituents each independently selected from:
   (a) —$C_{1-4}$alkyl which is unsubstituted or substituted with 1-3 substituents each independently selected from: halo, —O—$C_{1-6}$alkyl, —$CO_2R^9$, —$NR^{10}R^{11}$ and —$CONR^{10a}R^{11a}$,
   (b) phenyl or heterocycle, wherein heterocycle is selected from: pyridyl, pyrimidinyl, pyrazinyl, pyrrolidinyl, azetidinyl, piperidinyl and morpholinyl, which phenyl or heterocycle is unsubstituted or substituted with 1-3 substituents each independently selected from: —$C_{1-4}$alkyl, which is unsubstituted or substituted with 1-5 fluoro, —O—$C_{1-4}$alkyl, which is unsubstituted or substituted with 1-3 fluoro, halo and hydroxy,
   (c) halo,
   (d) hydroxy,
   (e) —O—$C_{1-6}$alkyl which is unsubstituted or substituted with 1-5 halo,
   (f) —CN,
   (g) —$NR^{10}R^{11}$,
   (h) —$CONR^{10a}R^{11a}$, and
   (i) oxo.

17. A compound according to claim 1 selected from:

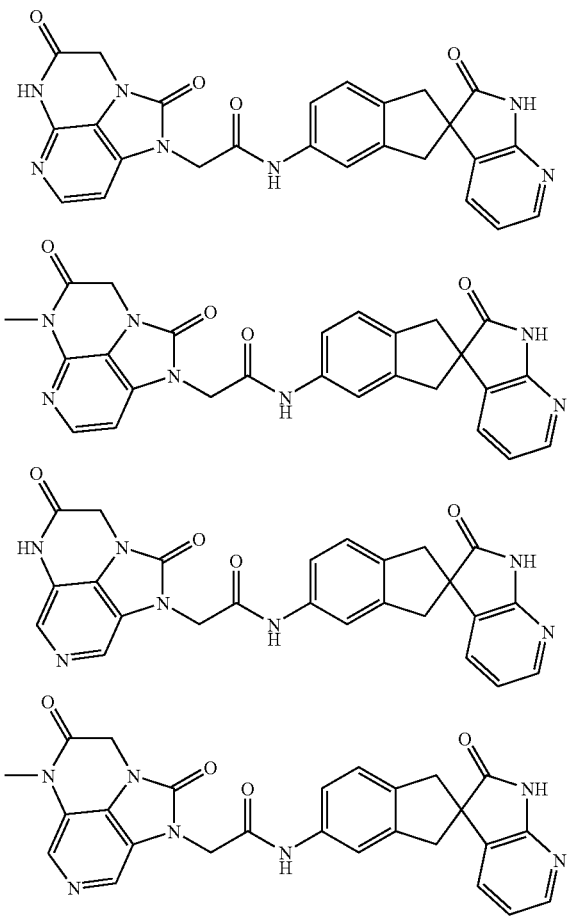

or a pharmaceutically acceptable salt, individual enantiomer or individual diastereomer thereof.

18. A pharmaceutical composition which comprises an inert carrier and the compound of claim 1, or a pharmaceutically acceptable salt thereof.

19. A method for treating, controlling, ameliorating or reducing the risk of headache, migraine or cluster headache in a mammalian patient in need of such which comprises administering to the patient a therapeutically effective amount of the compound of claim 1, or a pharmaceutically acceptable salt thereof.

* * * * *